United States Patent [19]

Taylor et al.

[11] Patent Number: 4,859,057
[45] Date of Patent: Aug. 22, 1989

[54] OXIMETER APPARATUS

[75] Inventors: Steve Taylor; Dale Nelson, both of Camarillo; Don Gorney, Simi Valley, all of Calif.

[73] Assignee: Lawrence Medical Systems, Inc., Camarillo, Calif.

[21] Appl. No.: 108,164

[22] Filed: Oct. 13, 1987

[51] Int. Cl.⁴ .................. A61B 5/00; G01N 33/16
[52] U.S. Cl. ................................. 356/41; 128/633
[58] Field of Search .............. 356/41; 728/633, 664, 728/665

[56] References Cited

U.S. PATENT DOCUMENTS

| | | | |
|---|---|---|---|
| 4,086,915 | 5/1978 | Kofsky et al. | 356/41 |
| 4,407,290 | 10/1983 | Wilber | 356/41 |
| 4,447,150 | 5/1984 | Heinemann | 356/41 |
| 4,700,708 | 10/1987 | New et al. | 356/41 |
| 4,714,080 | 12/1987 | Edgar et al. | 128/633 |
| 4,714,341 | 12/1987 | Hamaguri et al. | 351/41 |
| 4,759,369 | 7/1988 | Taylor | 128/633 |

FOREIGN PATENT DOCUMENTS

| | | |
|---|---|---|
| 0102816 | 3/1984 | European Pat. Off. . |
| 0194105 | 9/1986 | European Pat. Off. . |
| 0221642 | 5/1987 | European Pat. Off. . |
| 3629447 | 4/1987 | Fed. Rep. of Germany . |
| 86/05674 | 10/1986 | PCT Int'l Appl. ............ 128/633 |

Primary Examiner—Richard A. Rosenberger
Attorney, Agent, or Firm—Rosen, Dainow & Jacobs

[57] ABSTRACT

An oximeter apparatus especially adapted to reflectance oximetry includes a sensor having a red LED, an infrared LED and a photosensor resiliently mounted in a carrier to provide constant linear pressure characteristics. The LED's and photodetector are fixed to a flexible circuit board. The d.c. components of the reflectance signals are fed back to control the brightness of the LED's A.c. component signals from the photodetector are rejected in the determination of oxygen saturation when the red and infrared a.c. components differ by more than a determined amount. The difference between the maximum and minimum values of each pulse is employed in the determination of oxygen saturation, with two measurements being taken for each pulse.

8 Claims, 52 Drawing Sheets

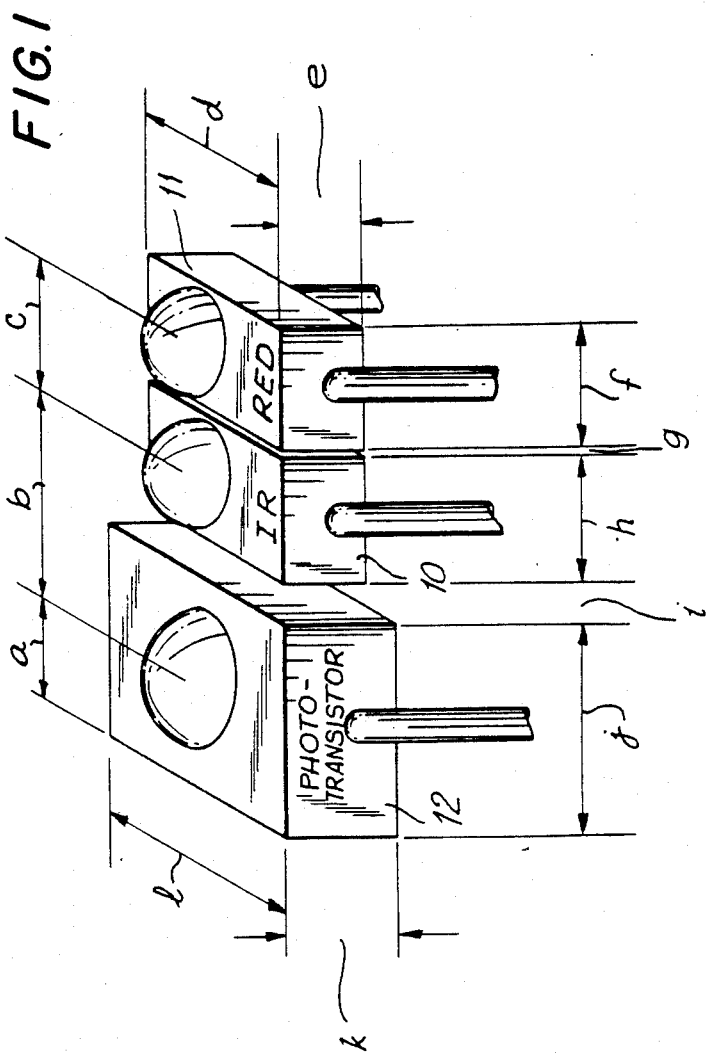

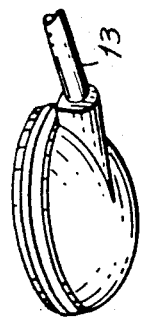
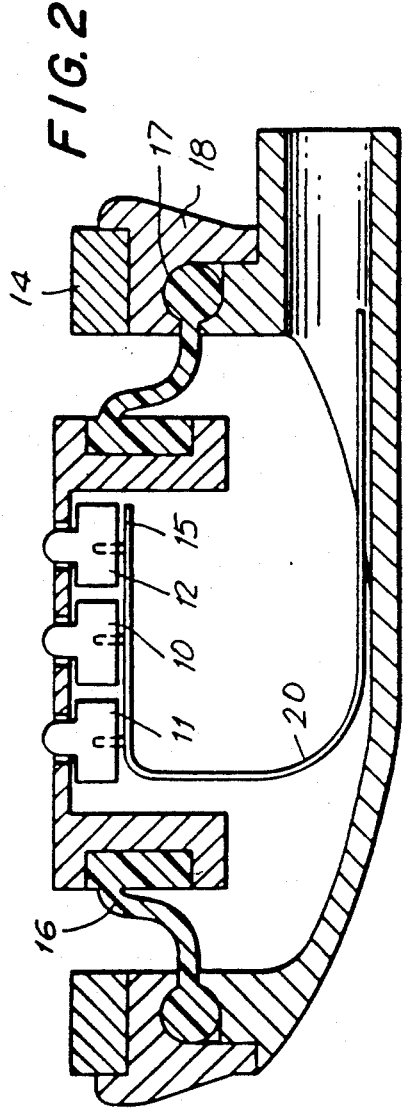

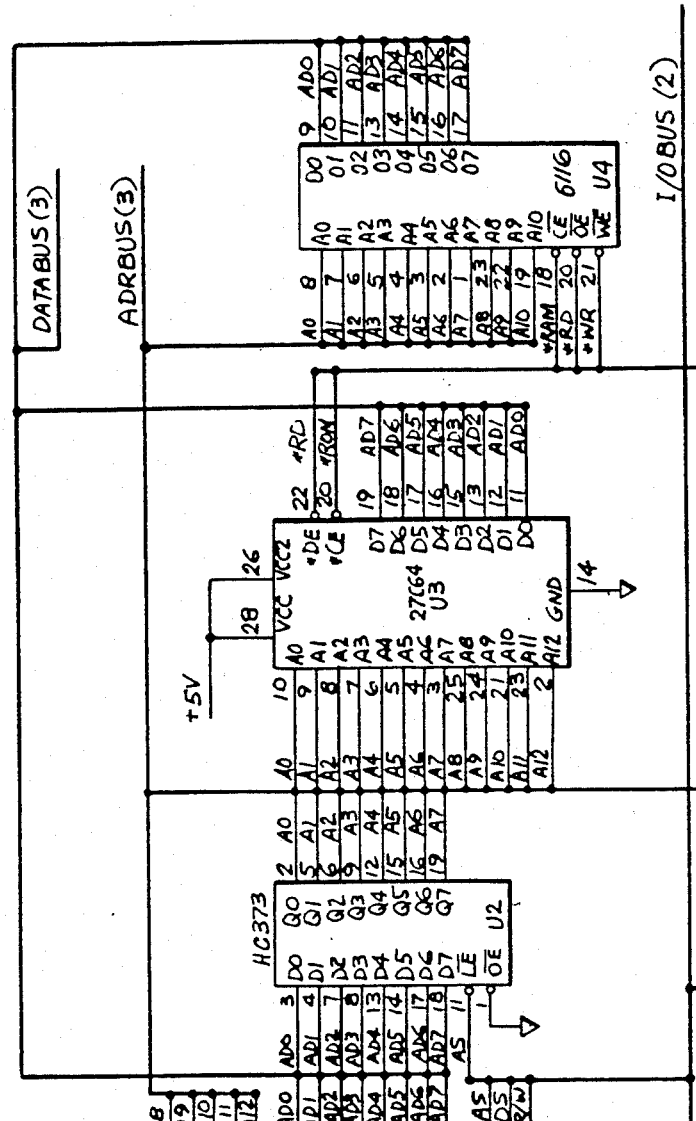
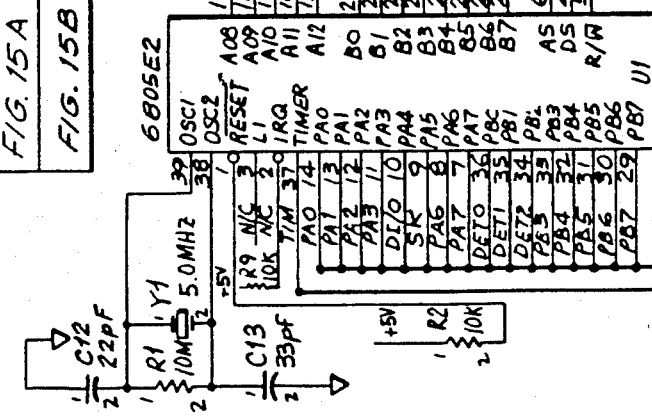
FIG. 15A
FIG. 15
| FIG. 15A |
|---|
| FIG. 15B |

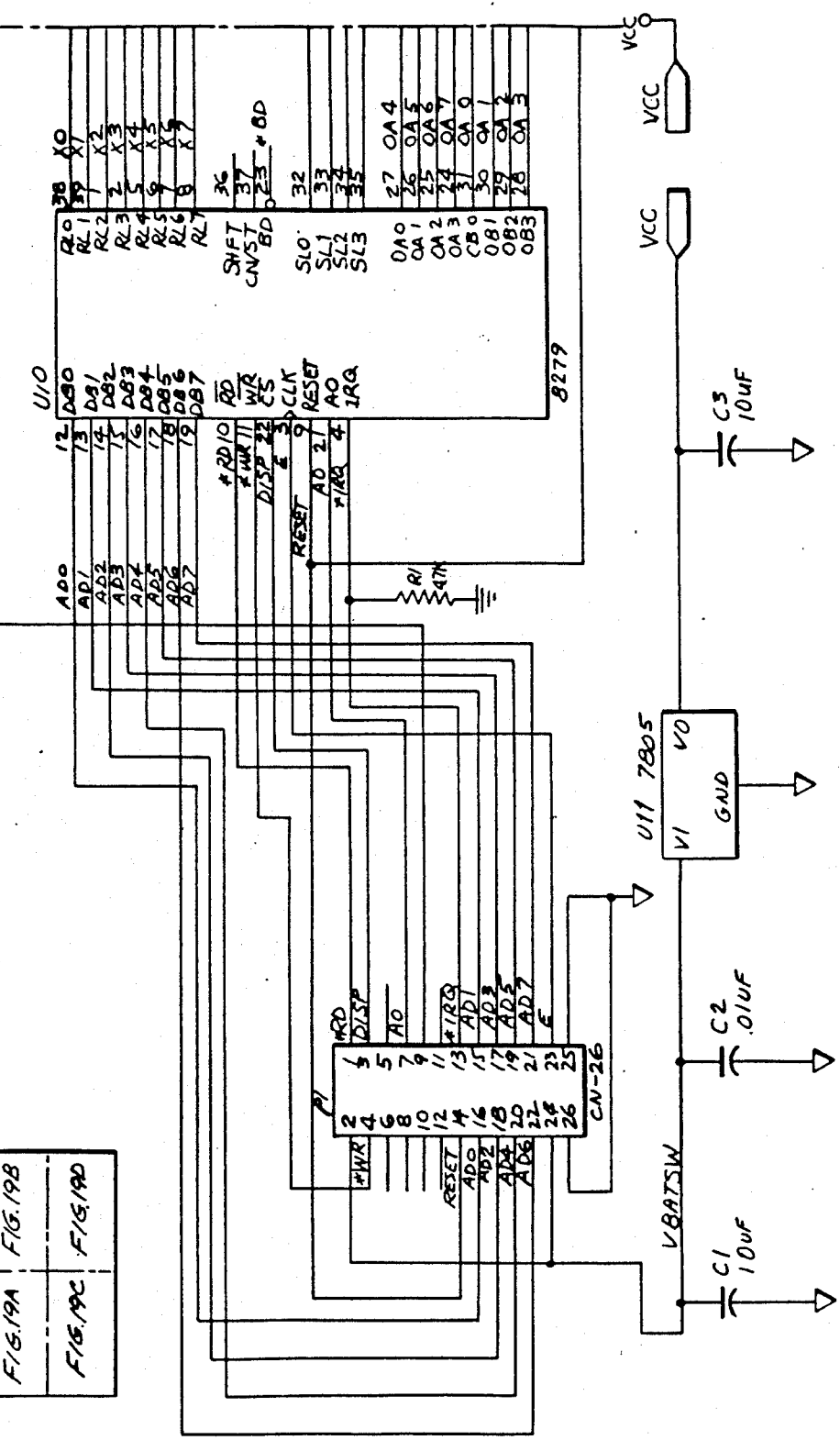

TABLE OF CONSTANTS

| NAME | HEX | DEC | DESCRIPTION |
|---|---|---|---|
| VPULH | 31H | 49 | VALID PULSE HEIGHT (.95v) |
| HHYS | 80H | 140 | HIGH HYSTERISIS LIMIT (2.73) |
| LHYS | 74H | 116 | LOW HYSTERISIS LIMIT (2.26) |
| RDIFL | 22H | 34 | RED DIFF LOW LIMIT (.66v) |
| JDIFL | 25H | 37 | IR DIFF LOW LIMIT (.72v) |
| PEGH | ECH | 236 | PEGGED HIGH LIMIT (4.6v) |
| PEGL | 13H | 19 | PEGGED LOW LIMIT (.37v) |
| DCHIGH | DC | 220 | DC HIGH LIMIT (4.3v AT A/D) |
| DCLOW | 22 | 16 | DC LOW LIMIT (.31v AT A/D) |
| DCHYS | 4 | 4 | DC HYSTERISIS (.08v) |
| LODC | 28 | 40 | LOWEST STARTUP ACCEPTED (.78v) |
| VMAYS | 25 | 37 | VECTOR MOTION HYSTERISIS (.72v) |
| OXYULI | 64 | 100 | OXY INITIAL UPPER LIMIT |
| OXYLLI | 58 | 88 | OXY INITIAL LOWER LIMIT |
| PULSULI | 78 | 120 | PULSE INITIAL UPPER LIMIT |
| PULSLLI | 28 | 40 | PULSE INITIAL LOWER LIMIT |
| K_ROWS | 3 | 3 | NUMBER OF ROWS TO BE SCANNED |
| D_CONST | 33 | 51 | DIVIDE CONSTANT |
| NK_TOUT | 32 | 50 | NO. KEY TIMEOUT |
| M_DELAY | 26 | 150 | ALARM MUTE DELAY TIME |
| DB_AREP | 01 | 1 | DELAY TILL AUTO REPEAT |
| PH_MODE | 01 | 1 | DELAY BEFORE OR BETWEEN AUTO REPEAT |
| PL_MODE | 03 | 03 | KEY DEFS   PULSE H |
| PL_MODE | 02 | 02 | PULSE LOW |
| SH_MODE | 01 | 01 | SAT HI |
| SL_MODE | 13 | 19 | SAT LO |
| INC_K | 12 | 18 | INCREMENT KEY |
| DEC_K | 11 | 17 | DECREMENT KEY |
| RESP_K | 23 | 35 | RESPONSE KEY |
| MUTE_K | 22 | 34 | MUTE KEY CODE |
| NO_KEY | 77 | 119 | NO KEY TIME OUT KEY CODE |
| BIG1ST | 5 | 5 | LARGE DIGIT 1ST CHARACTER |
| BIG2ND | 16 | 16 | LARGE DIGIT 2ND CHARACTER |
| BIG3RD | 27 | 27 | LARGE DIGIT 3RD CHARACTER |
| BIG4TH | 85 | 128+5 | LARGE DIGIT 4TH CHARACTER |
| BIG5TH | 90 | 128+16 | LARGE DIGIT 5TH CHARACTER |
| BIG6TH | 98 | 128+27 | LARGE DIGIT 6TH CHARACTER |

FIG. 22

FIG. 24
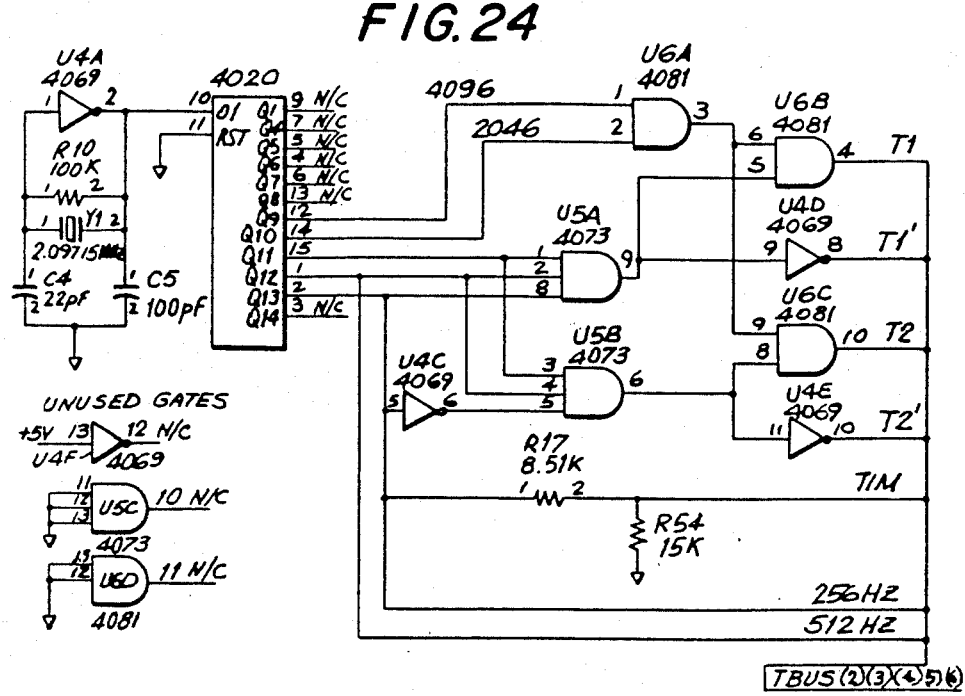
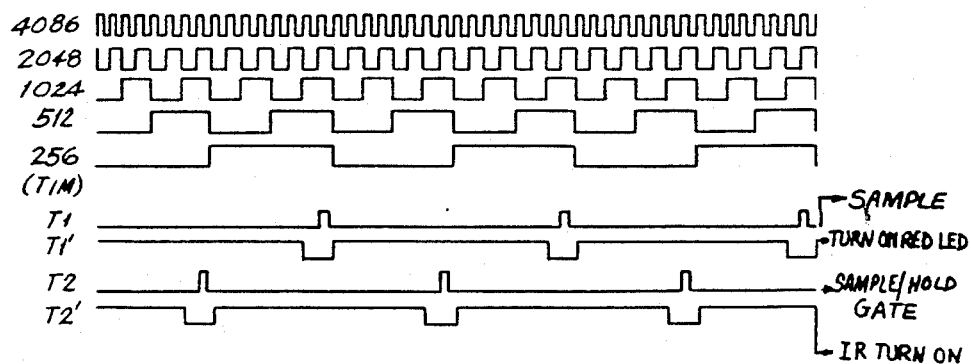
FIG. 25

SET UP

ACTION

FIG. 30

DACR: SELECT DAC THRU BITS 0,1,2 OF PORT A; 110 = DAC
5, PORTA ← 0 (CLOCK LOW)
4, PORTA ← 0 (DATA LOW); X ← OXYA (OXYAVE) CALL EIGHTb;
X (OUTPUT 6 BITS); X ← OXY (DUMMY); CALL EIGHTb
X ← NOT B (NOT END); CALL EIGHTb; X ← LAST +1 (IR LAST);
CALL EIGHTb; X ← LAST (RED LAST); CALL EIGHTb;
X ← BRIGHT; LEFTSHIFT X; LEFTSHIFT X (MOVE OUT UNUSED
BITS OF BRIGHT); CALL EIGHTb; 5, PORTA ← 1; 4, PORTA ← 1;
CALL OFF

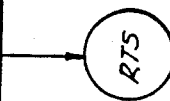 RTS

ANIN1:
PORTA, 2-0 (AS LOW)
PORTA, 5-1 (ON CLR 1)
LEFT SHIP X 3 TIMES
A ← 5
JSR SEND A
SEND NEXT 5 BITS OF X
DDRA, H ← 0 INPUT
PORTA, 5 ← 0 CLOCK↓
JSR GET (SET 8 BITS IN X
  FROM CONVERSION)
CALL OFF (CS HIGH)
DDRA, 4 ← 1 (OUTPUT)

 RTS

FIG. 29

BRI PART 1

BRI PART 2

BRIH
BRIL

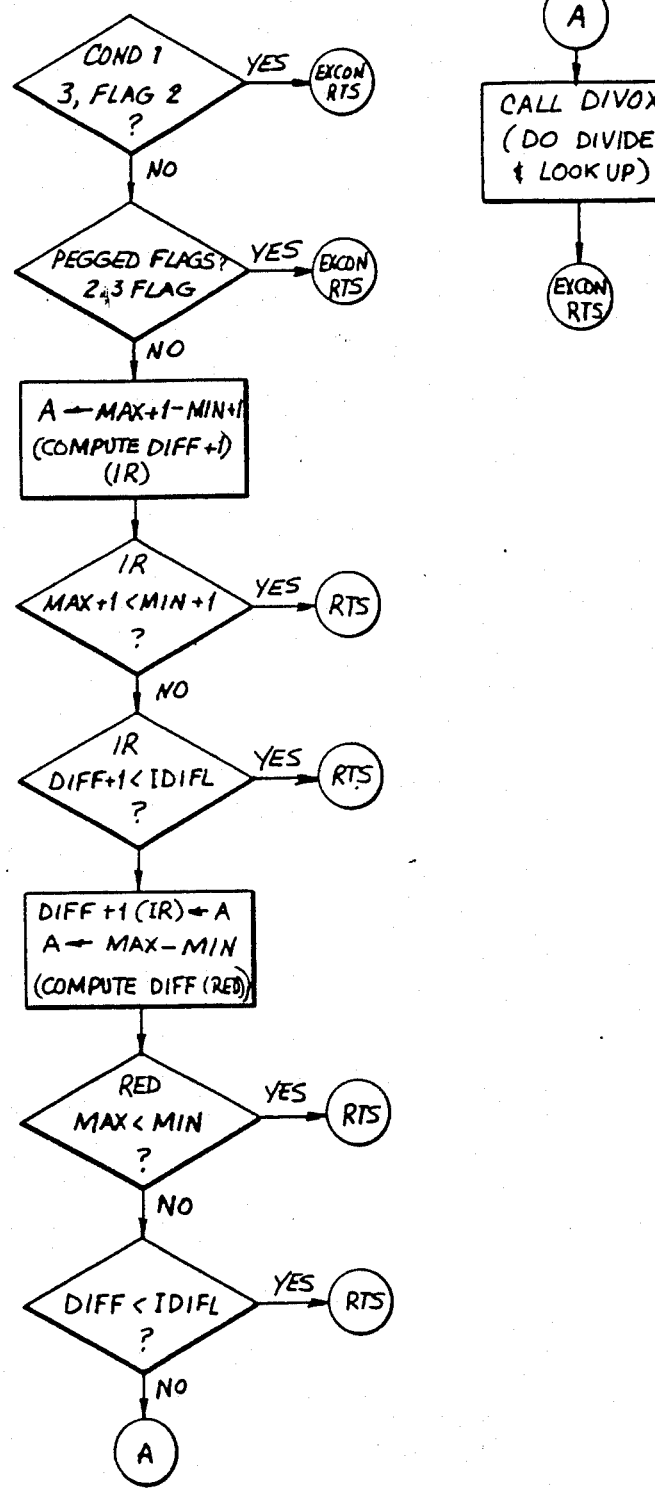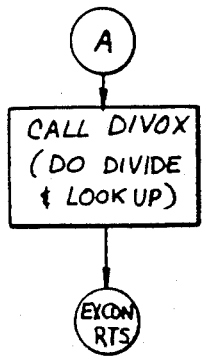
FIG. 34
COND1

DEELY

DOUBLE 2

DIVIDE

DIVOX

GET B

GET KEY

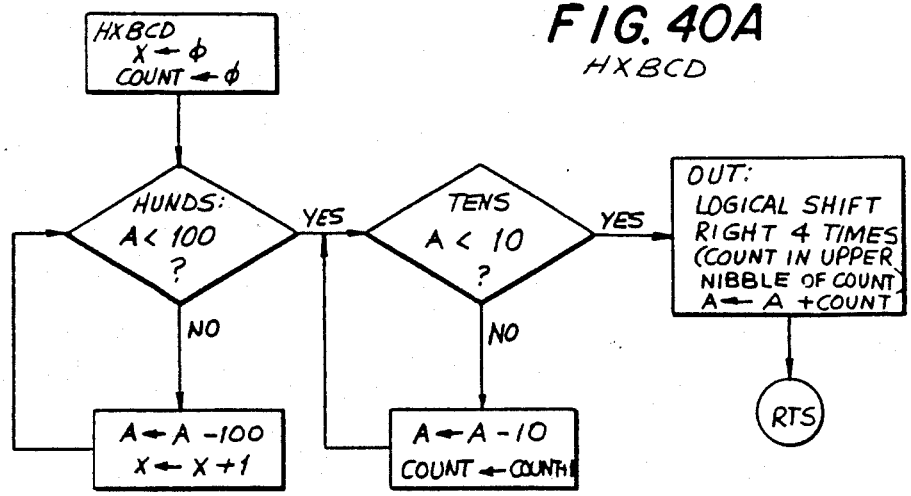
FIG. 40A
HXBCD
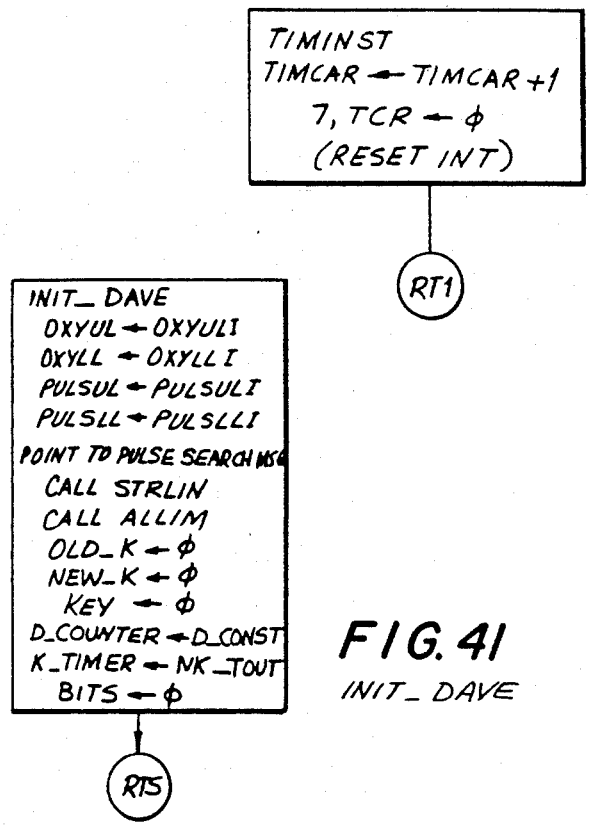
FIG. 40B
TIMINST
FIG. 41
INIT_DAVE

IRQ

LOW BAT

MAIN

EIGHT 6

OFF

MATCH

POSSET

```
POSSET
 X ← TEMPC
 A ← CPTABP,X
 DPOINT ← A
```

```
                SEC 1  EQU   0
                SEC 2  EQU  64
                SEC 3  EQU  128
                SEC 4  EQU  192

HEX
        00   CPTABP:  SEC 1        0   CHARACTER POSITION (UPPER ROW)
        06            SEC1+6       1
        0C             +12         2
        12             +18         3
        18             +24         4
        1E             +30         5
        24             +36         6
        80            SEC3         7
        86             +6          8
        8C             +12         9
        92             +18        10
        98             +24        11
        9E             +30        12
        A4             +36        13
        40            SEC2        14   (LOWEST ROW)
        46             +6         15
        4C             +12        16
        52             +18        17
        58             +24        18
        5E             +30        19
        64             +36        20
        C0            SEC4        21
        C6             +6         22
        CC             +12        23
        D2             +18        24
        D8             +24        25
        DE             +30        26
        E4             +36        27
```

PULSER

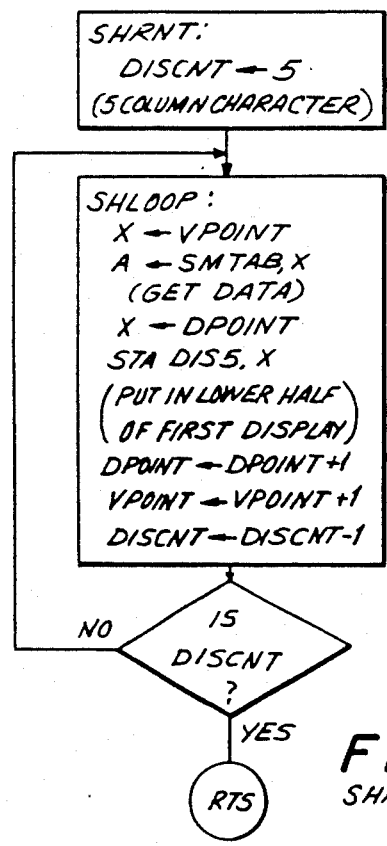
FIG. 48A SETUP
FIG. 48C SHRNT
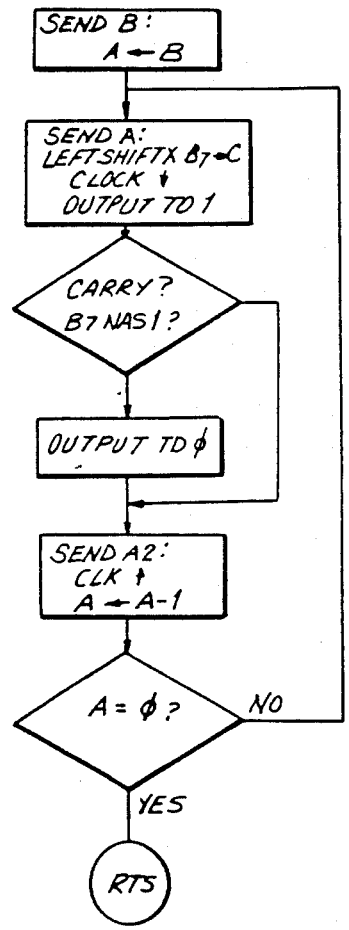
FIG. 48B SEND B

SHRNT 2

SHRNT 3

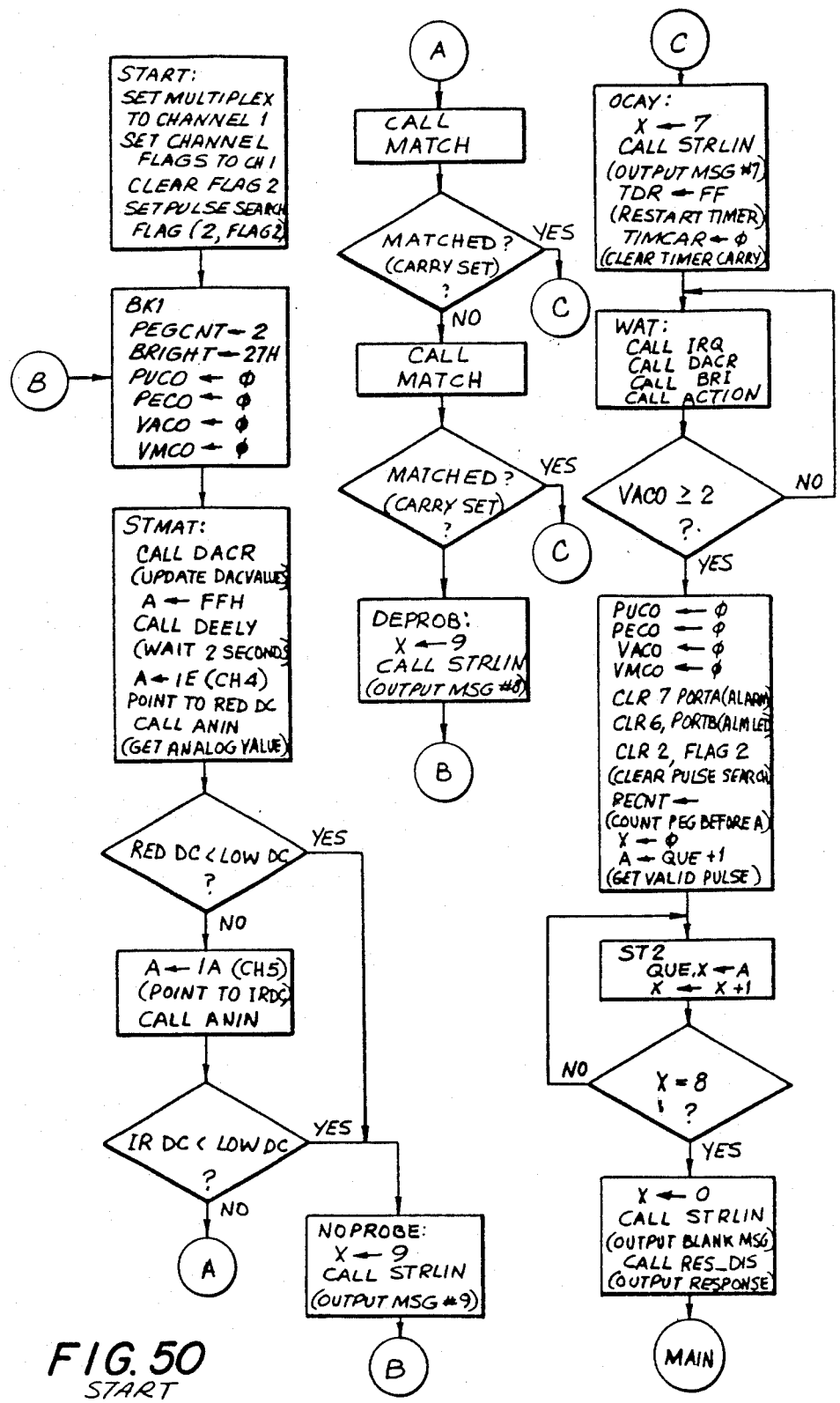
FIG. 50 START

\* X HOLDS OFFSET TO MESSAGE

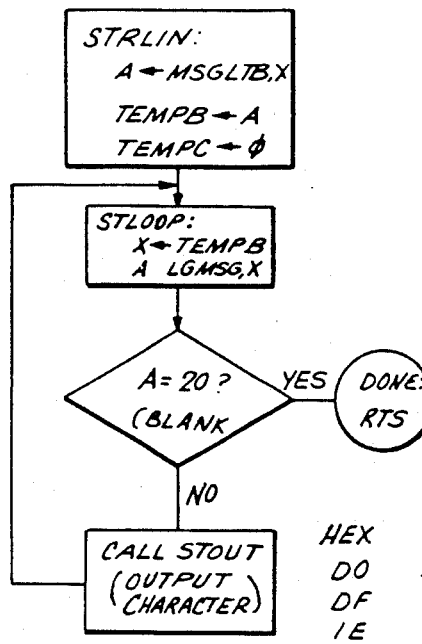

```
                LGMSG   3/4 & FULL LENGTH MESSAGES
                LGMG:
                LM0:    FCC  '@@@@@@@@@@@@@'
                LM1:    FCC  '@@@SAT@HIGH@@@'
                LM2:    FCC  '@@@SAT@LOW@@@@'
                LM3:    FCC  '@@PULSE@HIGH@@'
                LM4:    FCC  '@@@PULSE@LOW@@'
                LM5:    FCC  '@SIGNAL@@LOST@'
                LM6:    FCC  'LOW@PERFUSSION'
                LM7:    FCC  '@PULSE@SEARCH@'
                LM8:    FCC  '@CHECK@PROBE@@'
                LM9:    FCC  '@PLUG@PROBE@IN'
                LM10:   FCC  'BATTERY@DEAD@@'
                LM11:   FCC  '@BATTERY@LOW@@'
                LM12:   FCC  'MOTION@DETECT@'
                LM13:   FCC  '@NEXT@MESSAGE@'

HEX
        D0      MSGLTB: FCB   LM0 - LGMSG
        DF              FCB   LM1 - LGMSG
        1E              FCB   LM2 - LGMSG
        2D              FCB   LM3 - LGMSG
        3C              FCB   LM4 - LGMSG
        4B              FCB   LM5 - LGMSG
        5A              FCB   LM6 - LGMSG
        69              FCB   LM7 - LGMSG
        78              FCB   LM8 - LGMSG
        87              FCB   LM9 - LGMSG
        96              FCB   LM10 - LGMSG
        A5              FCB   LM11 - LGMSG
        B4              FCB   LM12 - LGMSG
        C3              FCB   LM13 - LGMSG
```

*FIG. 51*
STRLIN

TIBH

TESTL

TIBL

TREND

STOUT

OXIMETER APPARATUS

This invention relates to an oximeter, and is more in particular directed to the provision of a reference oximeter and method for operating the same.

BACKGROUND OF THE INVENTION

Pulse oximetry has become an accepted method of oxygen determination in the last five years. However, up to this point, all devices on the market have used the transmission method of detection. The pulse oximeter of the present invention is based upon a reflectance method. Both of these methods are based upon several related facts.

First, the concentration of blood in a given location of the body varies with each pulse of the heart. This variation can be measured by optical methods by introducing a light source near the skin and detecting either the reflected or the transmitted light intensity. This intensity is directly related to the localized blood concentration.

Secondly, the wavelength of the light source determines the effect that oxygen saturation has on the reflected or transmitted intensity. The wavelength which does not change intensity with saturation but only with concentration is called the isobestic wavelength. This isobestic condition occurs at several wavelengths. By using this wavelength as a reference and by comparing it to a second wavelength in the red portion of the spectrum, it is possible to determine the oxygen saturation of the blood non-invasively.

Current pulse oximeters using the transmissive method require the light from the emitters to pass through the tissue to the detector on the opposite side. This requires the sensor to be placed on an area of the body where the distance from the emitters to the detectors is fairly small (about an inch at most) and not obstructed by opaque tissue layers, such as bone. This limits the placement of the sensors to areas such as the finger tips, ear lobes, or the bridge of the nose.

SUMMARY OF THE INVENTION

The pulse oximeter of the invention uses a reflectance method where both the emitters and the detector of the sensor are placed next to each other. The light penetrates the tissue and is reflected back by the various layers of the skin and by the hemoglobin in the blood. By using this method, the sensor can be placed almost anywhere on the body where blood flow is sufficient. The light reflected back by the layers of the skin is fairly constant (or steady-state) whereas the light reflected back by the blood changes with each pulse depending upon the amount of blood in the tissue. Also, the hemoglobin in the blood changes coloration due to the amount of oxygen.

Pulse oximetry uses the amplitudes of the pulsation signals to determine the oxygen concentration of the blood rather than the steady-state levels of the signals. However, the steadstate levels must be nearly equivalent at all times to be able to measure oxygen saturation from the pusitile signals. Also, the steady-state, or DC, level of the signals must be adjustable to allow the sensor to compensate for factors such as skin pigmentation, skin thickness, and sensor coupling to the skin. This is achieved through the use of a voltage source to control the drive of the emitters in the sensor. The voltage source is controlled by the voltage level output from a digital to analog converter which gets its input from the microcontroller. This allows the microprocessor to select one of a multiple of brightness levels, for example 64, for the emitters. If the skin is heavily pigmented of if the blood flow in the area is limited, the microcontroller can increase the brightness of the emitters to compensate. Since the characteristics of the light emitting diodes used as the emitters can change slightly with continued use or temperature change, it is necessary to employ an integrator to measure and compensate for changes in DC levels. The time it takes to compensate for these changes can also be controlled by the microcontroller. When the brightness of the emitters needs to be changed, the microcontroller changes the brightness control voltage and also the time constant of the integrator from one second to 0.01 second. The DC levels are thus quickly changed to the new level and the new pulsatory signals are ready for sampling in less than one second. The first bandpass stage is also changed to a low pass filter to allow for the DC shift to settle out. This circuit is a key element in allowing this instrument to function properly on a wide variety of patients and over a wide range of conditions.

Briefly stated, in accordance with one feature of the invention, a reflectance oximeter is provided comprising a red light source, an infrared light source, a photodetector for receiving light from said sources reflected from tissue, first and second control circuits for energizing said red and infrared light sources respectively at different instants and signal processing means coupled to said photodetector and synchronized with said energizing means for determining oxygen saturation in said tissue. The process of reflection will be understood to include some degree of diffusion. The signal processing means comprises means for generating first and second feedback signals corresponding to DC component of Red and IR light respectively received by the photosensor. Means are provided for applying the first and second signals to the first and second control circuits. The first and second control circuits comprise means employing the feedback signals as negative feedback signals in the energization of the sources. The control circuits may comprise time constant circuits, and means for varying the time constant of application of the feedback signals thereto. The system may comprise a source of a brightness control voltage, the control circuits further comprising means responsive to the brightness control voltage for controlling the energization of the red and infrared sources as a function thereof.

In a further feature of the invention, the reflectance oximeter comprises a red light source, an infrared light source, a photodetector for receiving light from the sources reflected from tissue, first and second control circuits for energizing the red and infrared light sources respectively at different instants and signal processing means coupled to the photodetector and synchronized with the energizing means for determining oxygen saturation in the tissue. The signal processing means comprises filter means for selecting the a.c. component from the signal output of the photodetector, and a controllable gain circuit for controlling the gain of the output of the signal processing means. The gain circuit comprises a plurality of amplifiers of different gain connected to simultaneously receive the same signal output from the filter means, an output circuit, and means for selectively connecting individual ones of the amplifiers to the output circuit. The plurality of amplifiers may comprise at least four amplifiers connected to receive the a.c. component of signals corresponding to infrared light and at least four amplifiers connected to receive the a.c. component of signals corresponding to red light. The amplifiers of each group of amplifiers have relative gains of 1, 1.25, 2 and 4.

In a still further feature of the invention, a reflectance oximeter comprises a red light source, an infrared light source, a photodetector for receiving light from the sources reflected from tissue, first and second control circuits for energizing the red and infrared light sources respectively at different instants, and signal processing means coupled to the photodetector and synchronized with the energizing means for producing first and second output signals corresponding respectively to reflected red light and reflected infrared light for determining oxygen saturation in the tissue. The signal processing means further comprises means for detecting relative variation in the first and second signals, and means for inhibiting the determination of oxygen saturation when the relative variation exceeds a determined level.

In accordance with another feature of the invention, a reflectance oximeter comprises a red light source, an infrared light source, a photodetector for receiving light from the sources reflected from tissue, first and second control circuits for energizing the red and infrared light sources respectively at different instants, whereby the photodetector receives pulses of reflected light corresponding separately to reflected red light and reflected infrared light, and signal processing means coupled to the photodetector and synchronized with the energizing means for determining oxygen saturation in the tissue. The processing circuits comprise means for sampling the maximum and minimum values of each pulse received from the photodetector, and means for producing output signals responsive to the levels of the last maximum and last minimum values of pulses corresponding to reflected red and infrared light. The processing circuits may comprise means for determining the difference between the maximum and minimum levels sensed for each pulse.

In a still further feature of the invention, a reflectance oximeter comprises a red light source, an infrared light source, a photodetector for receiving light from the sources reflected from tissue, first and second control circuits for energizing the red and infrared light sources respectively at different instants, signal processing means coupled to the photodetector and synchronized with the energizing means for determining oxygen saturation in the tissue, and means for matching the d.c. levels of the output signals from the photodetector corresponding to red and infrared light. The matching means comprises means for adjusting the brightness of at least one of the sources as a function of the corresponding d.c. level output from the photodetector. The matching means may comprise a brightness control circuit for the sources, a feedback circuit connected to feed back the d.c. components of the outputs of the photodetector to the control circuit. The control circuit may further comprise means for controlling the relative brightness of the light sources.

Still further in accordance with the invention, a reflectance oximeter comprises a sensor having a red light source, an infrared light source, and a photodetector for receiving light from the sources reflected from tissue. The sensor comprises a housing having an aperture, a sensor carrier, the light sources and photodetector being mounted to have active light emitting and light receiving surfaces respectively at one side of the carrier. An electrical connection arrangement is provided for the sources and photodetector within the housing, and resilient means are provided for mounting the carrier in the aperture, whereby the carrier floats with respect to the housing. The resilient means may comprise means for biasing the carrier to have a uniform linear pressure for displacements of the carrier through a determined range, and may comprise a membrane sealingly holding the carrier in the aperture. The arrangement may further comprise an interconnection cable extending into the housing, with the electrical connection arrangement comprising a flexible connection board having electrical leads thereon, the sources and photosensor being mounted on the flexible board, and the leads being connected to the cable. The flexible board is preferably mounted to resiliently yield to pressure applied to the carrier, and may be U-shaped.

In accordance with another feature of the invention, a reflectance oximeter comprises a sensor having a red light source, an infrared light source, and a photodetector for receiving light from the sources reflected from tissue. The sensor comprises a housing comprising a sensor carrier. The light sources and photodetector are mounted to have active light emitting and light receiving surfaces respectively at one side of the carrier externally of the housing. A light barrier coats the sources and photodetector on substantially all surfaces except the active light emitting and receiving surfaces. The light barrier means may comprise silver paint.

In another feature in accordance with the invention, a sensor arrangement for a reflectance oximeter comprises a red light source, an infrared light source, a photodetector for receiving light from the sources reflected from tissue, and a housing having a sensor carrier. The light sources and photodetector are mounted in the carrier to have active light emitting and light receiving surfaces respectively externally of the housing. The sources and photosensor are positioned along a straight line with the infrared source being positioned between the red source and photosensor. The axis of infrared sensor is preferably substantially 0.128 inches from the axis of the photosensor, and the axis of the red sensor is preferably substantially 0.085 inches from the axis of the infrared sensor.

In one method in accordance with the invention for reflectance oximetry wherein red and infrared light sources are separately sequentially energized, and reflected light from said sources is sensed to produce red and infrared reflectance signals respectively, the method comprises separating the a.c. and d.c. components of said reflectance signals, determining oxygen saturation from said a.c. signals, and adjusting the brightness of light from said sources to maintain said a.c. signals within a predetermined range.

In a further method in accordance with the invention for reflectance oximetry wherein red and infrared light sources are separately sequentially energized, and reflected light from said sources is sensed to produce red and infrared reflectance signals respectively, the method comprises separating the a.c. and d.c. components of said reflectance signals, determining the difference between the maximum and minimum values of each pulse of said a.c. component, and determining oxygen saturation from said difference by comparison of said difference with a look up table. The step of determining the difference preferably comprises determining the difference twice for each of the pulses.

In order that the invention may be more clearly understood, it will now be disclosed in greater detail with reference to the accompanying drawings, wherein:

BRIEF FIGURE DESCRIPTION

FIG. 1 is a perspective view of the arrangement of the LED's and sensor in accordance with one embodiment of the invention;

FIG. 2 is a cross-sectional view of the sensor housing;

FIG. 3 is a perspective view of the sensor housing;

FIG. 14 is a further interconnection circuit diagram;

FIG. 22 is a table of constants, showing various limits thereof;

FIG. 24 is a timing circuit that may be used in the system;

FIG. 25 is a timing diagram;

FIGS. 28–54 are flow diagrams illustrating the operation of the invention.

DETAILED DESCRIPTION OF THE INVENTION

Figure 4:
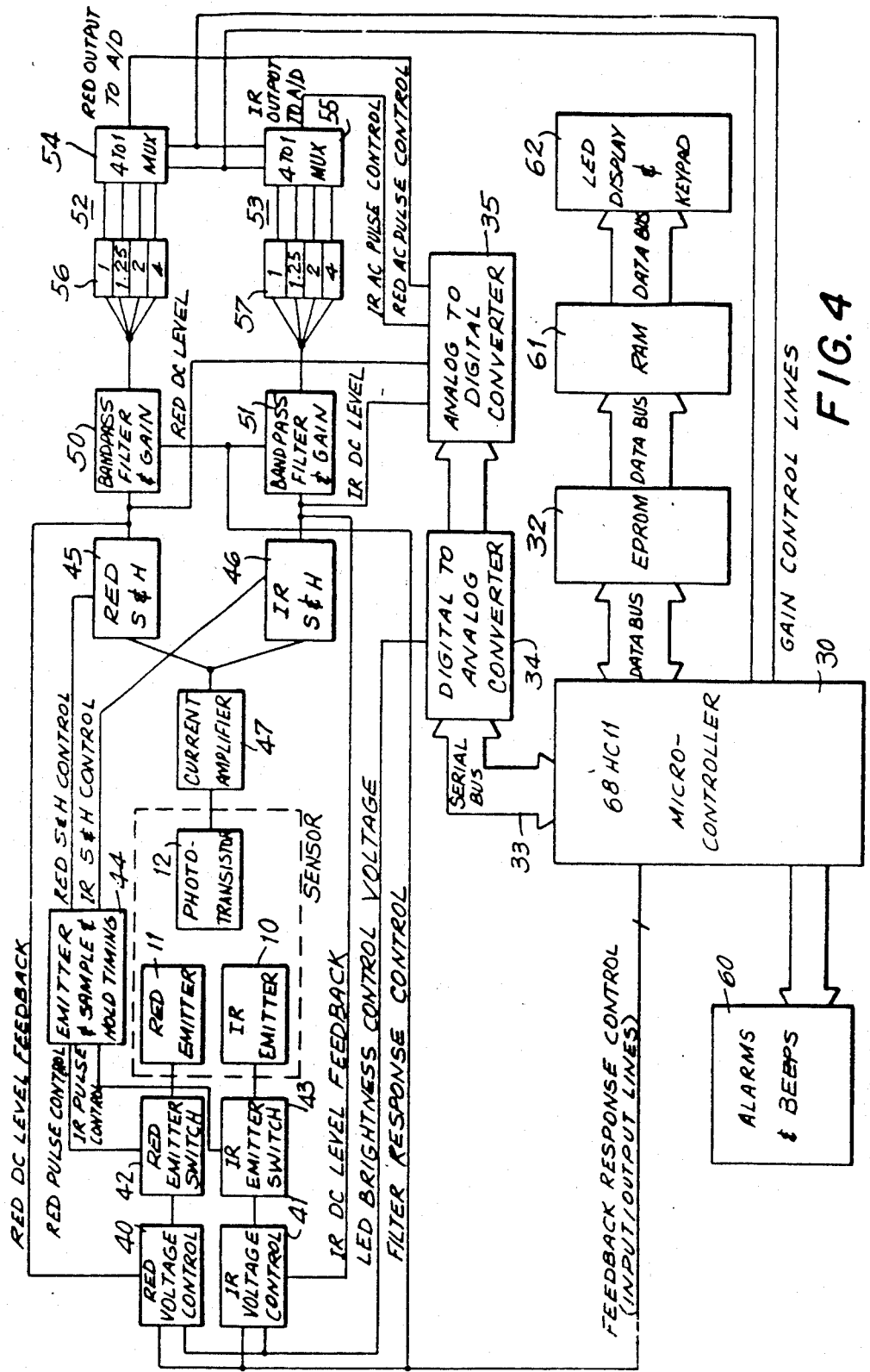
FIG. 4 is a block diagram of the system of the invention.
Figure 5:
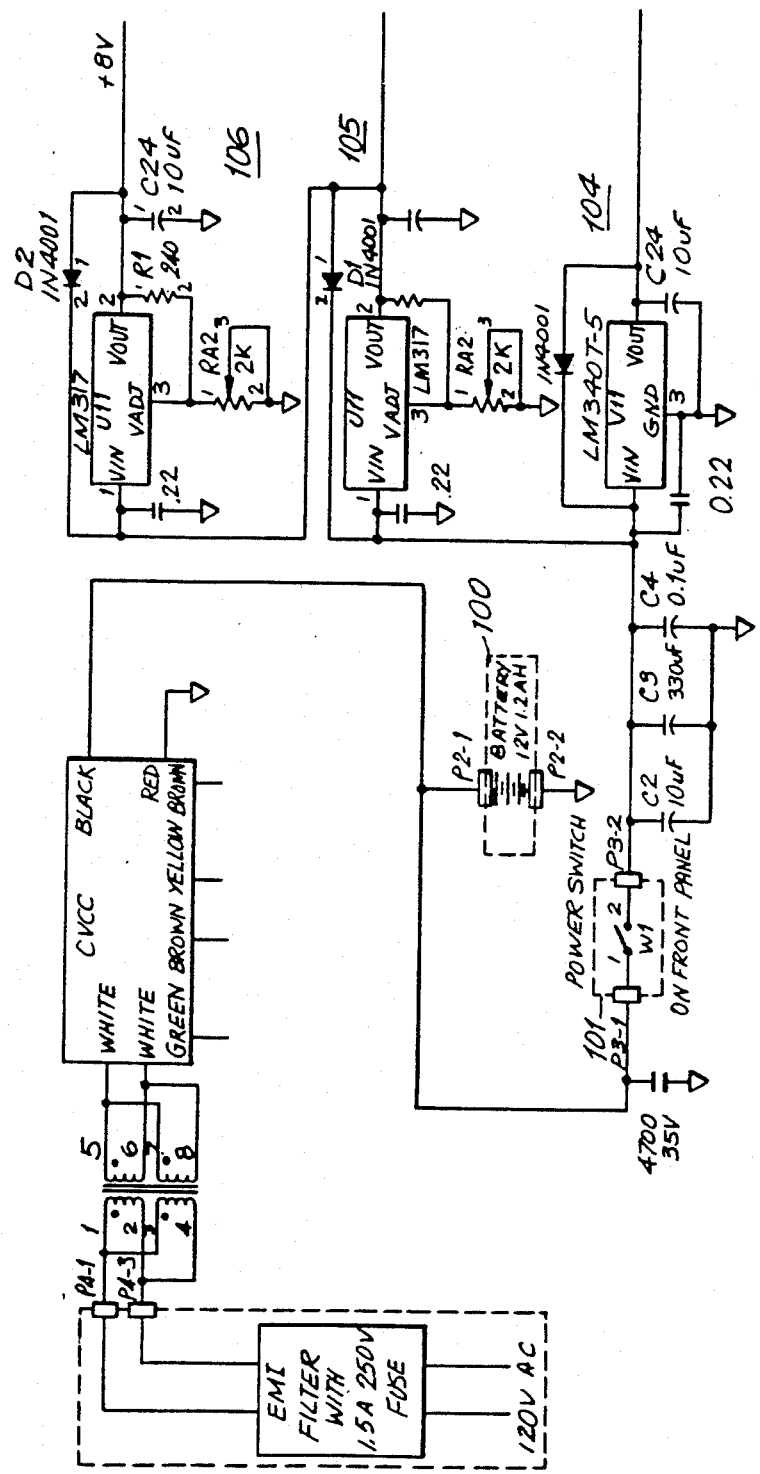
FIG. 5 is a circuit diagram of the power supply.

The sensor used with the reflectance oximeter in accordance with the invention preferably consists of the following:

a red LED (660 nanometers), and infrared LED (925 nanometers), and a phototransistor (800 nanometer-speak sensitivity). Multiples of each of the RED and INFRARED LED's are preferably employed.

The Infrared LED 10 is mounted in the center with the Red LED 11 on one side and the Phototransistor 12 on the other side. The spacing between each sensor and the arrangement is very critical. Saturation has been obtained with the sensors in other locations but the consistence and repeatability from site to site is maximized with the illustrated arrangement. Sensors have been placed in a triangular pattern with good results but the spacing between the three parts and their relationship to each other is critical.

The sensors are pulsed (turned on and off) at a rate of 256 times per second with a duty cycle of about ⅛. Each LED is turned on in synchronism with the phototransis tor and the sample and hold input circuit of the instrument. Thus the instrument sees the light reflected back from the skin from one LED at a time.

The attachment of the sensor to the skin is also very critical. A small amount of force (approximately 10 grams ) must be maintained to adequately hold the sensors in contact with the skin and yet not apply too much pressure to cause the area to be traumatized and thus cause blood flow restrictions. Tests have been conducted to determine if the sensor must be in contact with the skin. Results have shown that the sensor need not be in contact. Saturation has been obtained from as far away as ½ inch.

Although housings of a rigid plastic have been used with good results, the most favorable concept is one of more flexibility, one that would more easily and completely conform to the surface of the skin on which it was placed. Thus, either of two designs have been found to allow for proper operation. In one the whole housing is flexible and semi compliant with the sens or area on a floating membrane to insure proper pressure and contact. The other is of a harder type housing with the same sensor area as for the floating area membrane. The whole sensor housing is attached to the skin by means of a removable two sided adhesive foam donut pad. In order that the sensor be reusable, this foam pad can be removed and a new pad applied, thus insuring proper adhesion to each patient.

FIG. 1 shows the preferred sensor spacing and configuration. The spacing between the Infrared LED 10 and the Red LED 11 is not extremely critical, but the spacing between the Infrared/Red LED's and the phototransistor 12 is quite critical.

This spacing is as detailed on the drawing. The configuration is also to some degree critical. As mentioned above, the arrangement has been successfully employed with three sensors in a straight line, or in a triangular pattern. Various arrangements have produced limited good results, but the illustrated arrangement detailed on the drawing has produced the best, desired results. The drawing shows the wire connections for the sensors. The cathodes of the Red and the IR and the emitter of the Phototransistor are all tied to common. The anode of the Red, the anode of the IR, and the collector of the Phototransistor are brought back to the circuit separately. The RED and the IR are connected to their appropriate drivers and the collector of the Phototransistor is tied to the input operational amplifier and sample and hold circuit.

The signals need to be shielded from the RF and hence a ground plane over the conductors is required. An outer shield is provided over two of the conductors to help isolate them from the RF and the noise generated from the two LED's turning on and off.

The sensor has approximately 18" of cable 13 with a shielded plug attached to the end of the cable using a technique called insulation displacement. This plug plugs into a jack or the extension cable. The extension cable is designed to encase the plug with the exception of the very front chrome surface. The housing is molded of thermal plastic, such as a polyethylene, polycarbonate, pellathane or a styrene.

At the other end of the extension cable is another plug. This latter end plugs into the front of the machine. All of the plugs and jacks used are grounded from noise and RF. The pc board was designed and fabricated to allow the wires to mount to the jack, and also to provide shielding.

FIG. 2 illustrates the sensor housing utitlizing the hard concept. The sensors are allowed to float on a silicon rubber gasket type membrane. Referring to FIG. 2 an adhesive pad 14 is designed to be removed and a new one applied for each patient. The pad is approximately 0.062 thick and shaped like a donut.

The adhesive pad 14 has a carrier on both sides of the foam to aid in the adhesion and removal process. This carrier may be a very thin polyethylene material. This allows the adhesive to be removed from the patient and the sensor without tearing the pad. The pad is aligned and registered on the sensor with the use of a small raised guide tab. This small tab is approximately ½ the thickness of the pad and will force proper positioning of the pad without error. If the pad were to be applied nonconcentric, a portion of the sensor side of the pad could interfere with the movement of the floating diaphragm. This tab may be increased in height to just slightly higher than the pad thickness. This forms a light barrier around the sensing area of the skin to help block ambient light from reaching the phototransistor and causing potentially erroneous readings. The adhesive has a protective layer both top and bottom that will be peeled away when the pad is applied to the sensor and the patient. This protective layer is preferably split in the center to allow easy removal.

Reference numeral 15 is the sensor (LED's/phototransistor) mounting frame or carrier. The three sensor elements are mounted from the back side, the small dome lens thereof pushing through appropriate circular holes in the frame. They are mounted using an adhesive, such as UV cure epoxy. This LED carrier 15 provides many functions. The carrier is molded out of a dark, light blocking thermal plastic. The light cannot be permitted to enter the phototransistor except through the small domed lens area. The carrier will provides exact and proper positioning of the three sensors, and provides a proper test bed for testing the assembly, etc. The small domes protrude through the top of the carrier approximately 0.010. This will cause the sensor domes to always be in contact with the skin just slightly more than the whole top carrier piece. To increase their effectiveness, and to maximize their power and detection abilities, a silver reflective paint is applied on the outside of the RED, IR, and photo-transistor bodies. This paint covers all areas without interfering with the domed lens area. With the LEDs (RED/IR) this causes any and all emitted energy to be sent out through the dome area and not through the sides and bottom. On the phototransistor, it does two things. First, it helps block any ambient light, or light emitted from the RED and IR leds, and second, it helps capture all received light onto the die. On the RED and IR the paint also helps to block light from the phototransistor.

The silicon rubber gasket 16 is one of the key elements of the design. The silicon rubber gasket provides the following functions.

1. It provides a moisture barrier/dirt/contamination barrier from the outside to the inside.

2. The part allows the LED carrier to "float". This floating action will help insure proper skin contact at all times. If the housing is moved slightly, the inner carrier will float keeping the sensors in contact with the skin and eliminating a large amount of movement artifact.

3. Being of silicon rubber, it can easily be cleaned with normal hospital cleaning solutions. The silicon part is attached to the LED carrier in the manner of of a rubber band. It is stretched slightly, slipped over the top or bottom of the carrier 15 and put into place. The design is such that the silicon rubber will properly hold the carrier in place and provide all the required functions.

4. The design of the part is such as to afford a very small constant, linear force to the skin. This force is approximately 10 grams. The part, as the carrier is pushed down, will roll downward. This will continue to roll with a consistent linear motion for well over 0.100. Calculated max movement would be approximately 0.050 under normal use conditions.

5. This part is designed to apply a specific amount of preload to the carrier. This preload is set at approximately 0.020. This will force the sensor to always be in contact with the skin.

6. The rounded edge of the part is a ball 17 which allows easily an entrapment technique.

The top housing member 18 is designed to afford proper alignment of the pad, a stable surface for the pad to contact a light shield from outside ambient light, and half of the entrapment technique for the silicon rubber part 16.

The bottom 19 of the housing is nice and rounded to give a soft appealing look (See FIG. 3). The bottom housing also provides the other half of the entrapment for the silicon. The cord or cable 13 is mounted through a small extended opening off the bottom of the housing. The cable is bonded into the bottom housing with some epoxy based technique. The top and the bottom housing parts are connected using a solvent bonding operation.

The flex strip 20, having circuit traces for the sensor elements is attached to the LEDs/phototransistor providing the proper connections and is routed down and then soldered to the cable. The flex strip must be very flexible and not contribute or alter the linear movement of the LED carrier. Hence, the flex may be 0.001 kapton, with 1 oz copper trace and 0.001 kapton. Flexibility would be similar to that of one or two sheets of paper.

It has been found that all LED's and photodetectors do not operate satisfactorily in the environment of the invention. Specific devices that have the necessary saturation, color and intensity characteristics for correct operation of the system of the invention herein disclosed are BN501 (infrared LED), BR2262 (red LED) and PS502 (phototransistor), all products of Stanley Optoelectronics of Japan.

Referring now to FIG. 4, therein is illustrated a block diagram of the oximeter aparatus in accordance with the invention. The oximeter is controlled by a microcontroller 30 coupled via the data bus 31 to a program memory 32. The microcontroller 30 is connected to a serial bus 33, to apply digital signals to the digital to analog converter 34 and receive signals from the analog to digital converter 35.

The digital to analog converter 34 applies a brightness control voltage to voltage control circuits 40, 41 for the red and infrared LEDs, the control circuits 40, 41 applying operating current to the red and infrared emitters 11, 10 by way of electronic switches 42, 43, respectively. The switches 40, 42 are controlled by a timing circuit 44 which also controls the operation of red and infrared sample and hold circuits 45, 46, respectively, so that the output of the sample and hold circuit 45 occurs synchronously with the turning on of the red emitter switch 42, and the output of the infrared sample and hold circuit 46 occurs synchronously with the turning on of the infrared emitter switch 43.

The output of the phototransistor 12 is applied by way of the current amplifier 47 to the sample and hold circuits 45, 46, and thence to band pass filter and gain circuits 50, 51, respectively and thence to controlled gain circuits 52, 53, respectively. The outputs of the gain circuits, which may include four to one selectors 54, 55, is applied to the analog to digital converter 35, and thence on to the serial bus. The four to one selectors or multiplexers 54, 55 are controlled by the microcontroller 30, to select the desired gain level from multiple gain amplifiers 56, 57, respectively.

The outputs of the sample and hold circuits 45, 46 are applied as DC level feed-backs to the voltage control circuits 40, 41, respectively, as well as to the analog to digital converter 35 to enable monitoring of this DC level by the microcontroller. The band pass filter and gain circuits 50, 51 are controlled by the filter response control line from the microcontroller, as is the response of the control circuits 40, 41. The circuits is further provided with a suitable alarm and beeping circuit 60, random access memory 61, and a display and keypad circuits 62.

Figure 6:
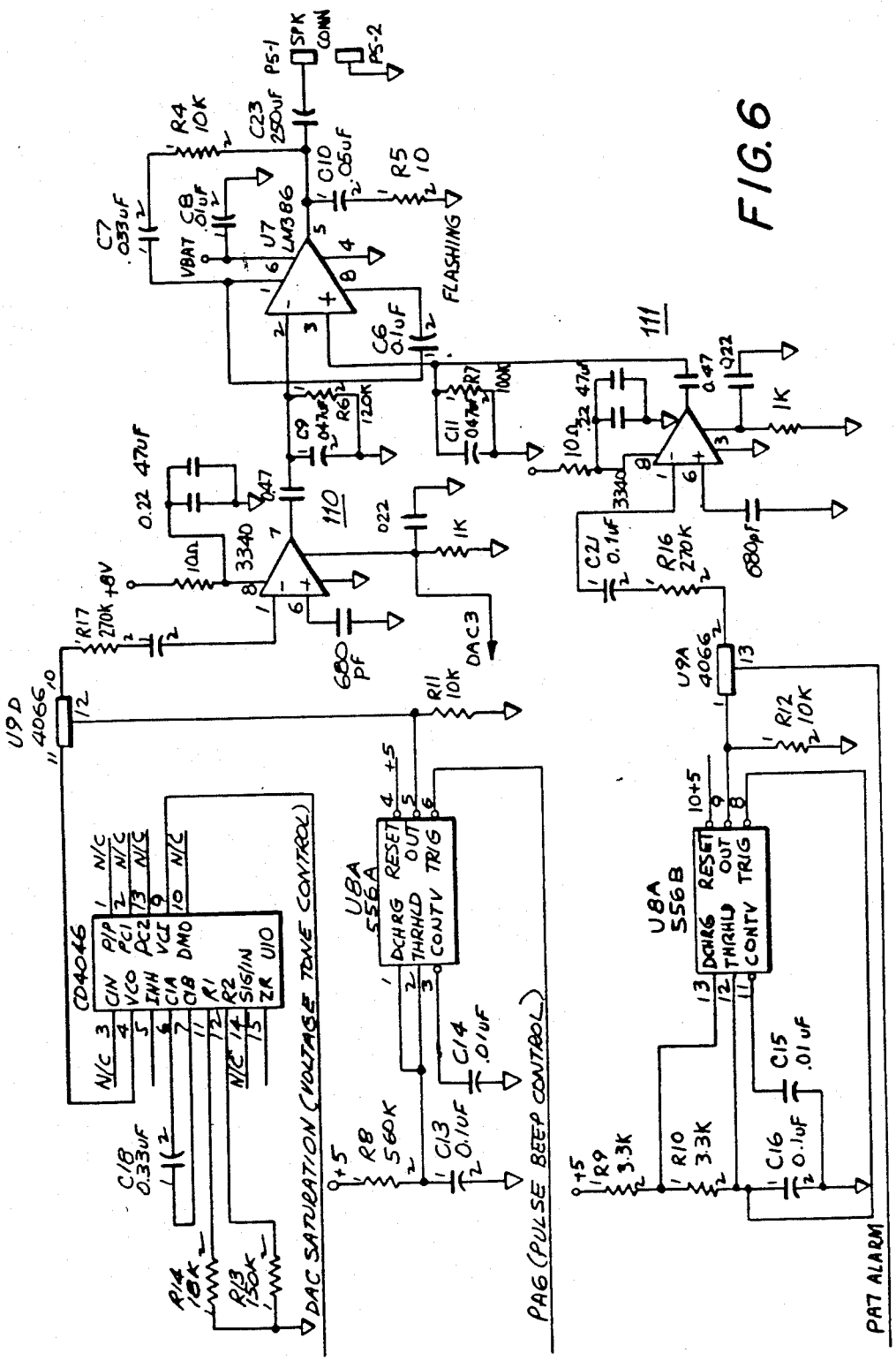
FIG. 6 is a circuit diagram of the alarm control circuits.

On the left-hand side of FIG. 6 is the 120 volt A.C. input to an EMI filter, thence through a transformer, to the constant voltage constant current charger CVCC which maintains the 12 volt battery at a full charge during its usage, as long as it's plugged in. As soon as the wall current is lost, battery backup enables continued operation for approximately two hours, or up to eleven hours when LCD displays are employed.

The 12 volt battery 100 is coupled via a power switch 101 to three voltage regulators. The supply 105 outputs a voltage ABIASto provide a pseudo-ground for operating the op amps. This output is four volts. The LM317 supply 106 is connected as an 8 volt regulator and supplies the upper rails for all of the analog circuitry. The LM340T supply 109 supplies the microprocess or board with 5 volts.

Figure 7:
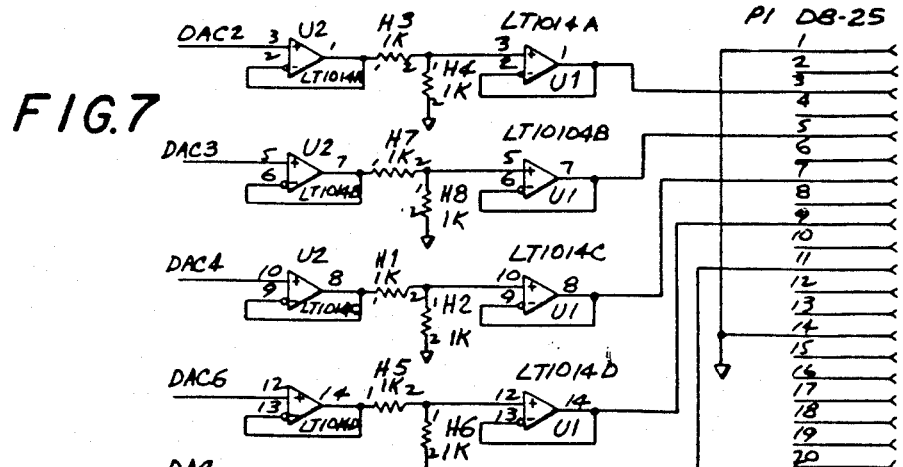
FIG. 7 is a circuit diagram of a voltage output circuit.

FIG. 7 shows all of the circuitry necessary to control the tone change for the speaker or a saturation change, and to control how long of a beep to have for the pulse. This is done with a 556. It also includes a multivibrator to generate the tone for the alarm. The part 4046, U10, is a voltage-controlled oscillator to produce the tone desired for the saturation value. The controlling voltage is DAC Saturation which comes from the DAC of the microcontroller board. The pulse is controlled by signal PA6 that goes to the trigger of U8A to give about a 20 millisecond pulse output to the 4066 switch U9D. U9D acts an an analog switch to control whether the signal is present or not. After being supplied with AC bias the signal goes to a 3340 connected as a voltage controlled attenuator 110. The control voltage for the 3340 is from line DAC 3 and, along with the output from the microcontroller via U9D, control is provided for the magnitude of the signal, plus controlling the volume.

U8A includes a 556 connected in a multivibrator mode to generate a tone. That tone is controlled by the 4066, U9A. The signal PA7 gates the 4066 to control whether the alarm tone is on or not. The software controls when the alarm is on. The beep signal is not mixed with it, so this circuit makes sure there is only one signal there. The alarm signal is applied to a 3340, 111, to enable control of the volume of the alarm with the signal called DAC 2. This is a buffered output from the DAC on the microcontroller board. Both of these signals are fed into an LM386 audio amplifier U7. The LM386 is operated by the supply voltage VBAT and drives the speaker through AC coupling via C23.

FIG. 7 is a diagram of a circuit for a voltage output to enable verification of the functionality of the unit and also to give an output proportional to saturation, a pulse wave form, for clinical research. The output goes to a DB25 connector on the back panel. The unit may have three analog outputs, one for pulse, one for saturation, and one for the wave form, or variation as desired.

Figure 8:
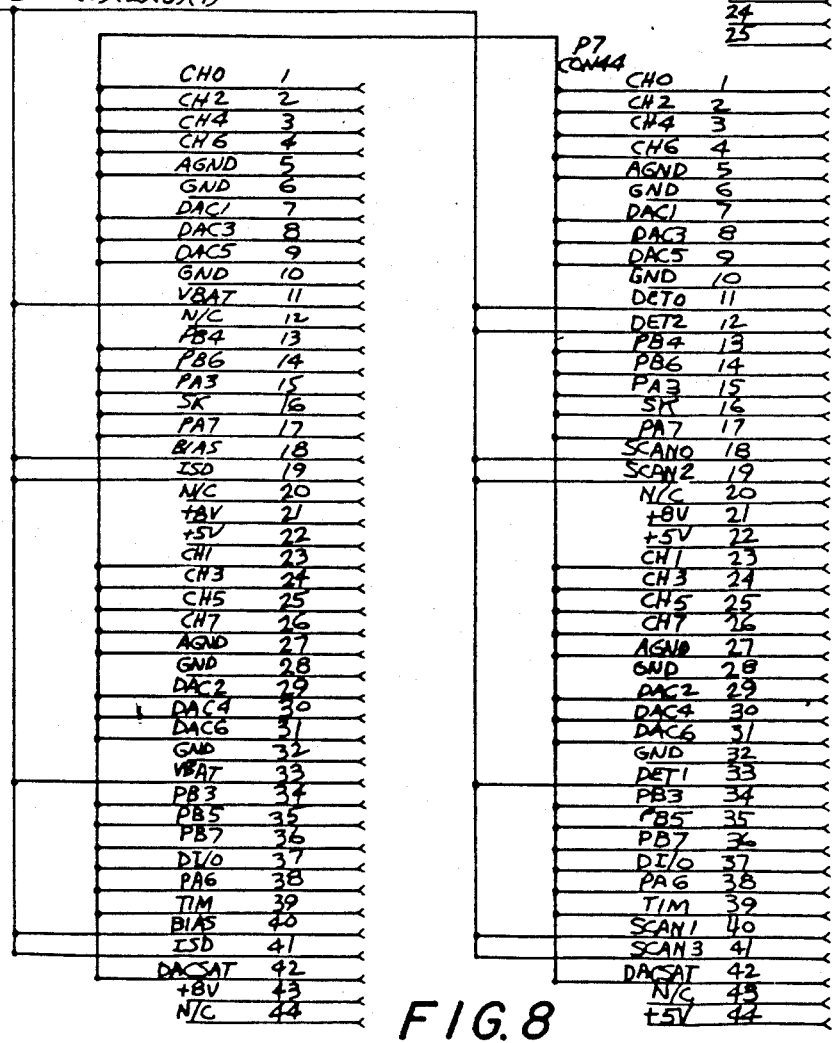
FIG. 8 is a connection diagram for clarification.

FIG. 8 shows self-explanatory connections between the two 44 pin connectors in the circuit.

Figure 9:
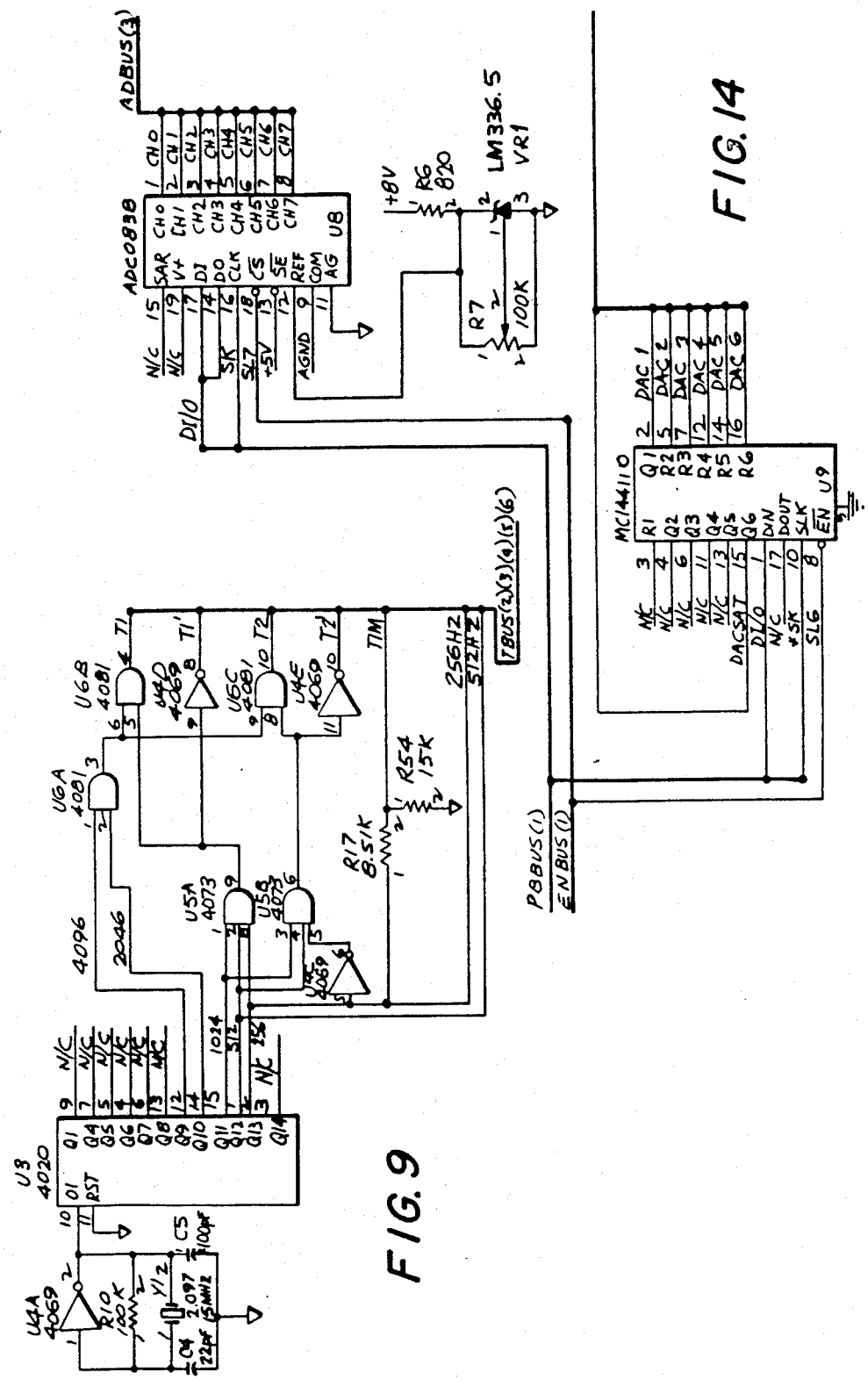
FIG. 9 is a circuit diagram of the timing circuits.

FIG. 9 shows the analog circuits 44 concerned with the timing generation for turning on and off the LEDs and turning on and off the sample and hold at the appropriate time.

Figure 10:
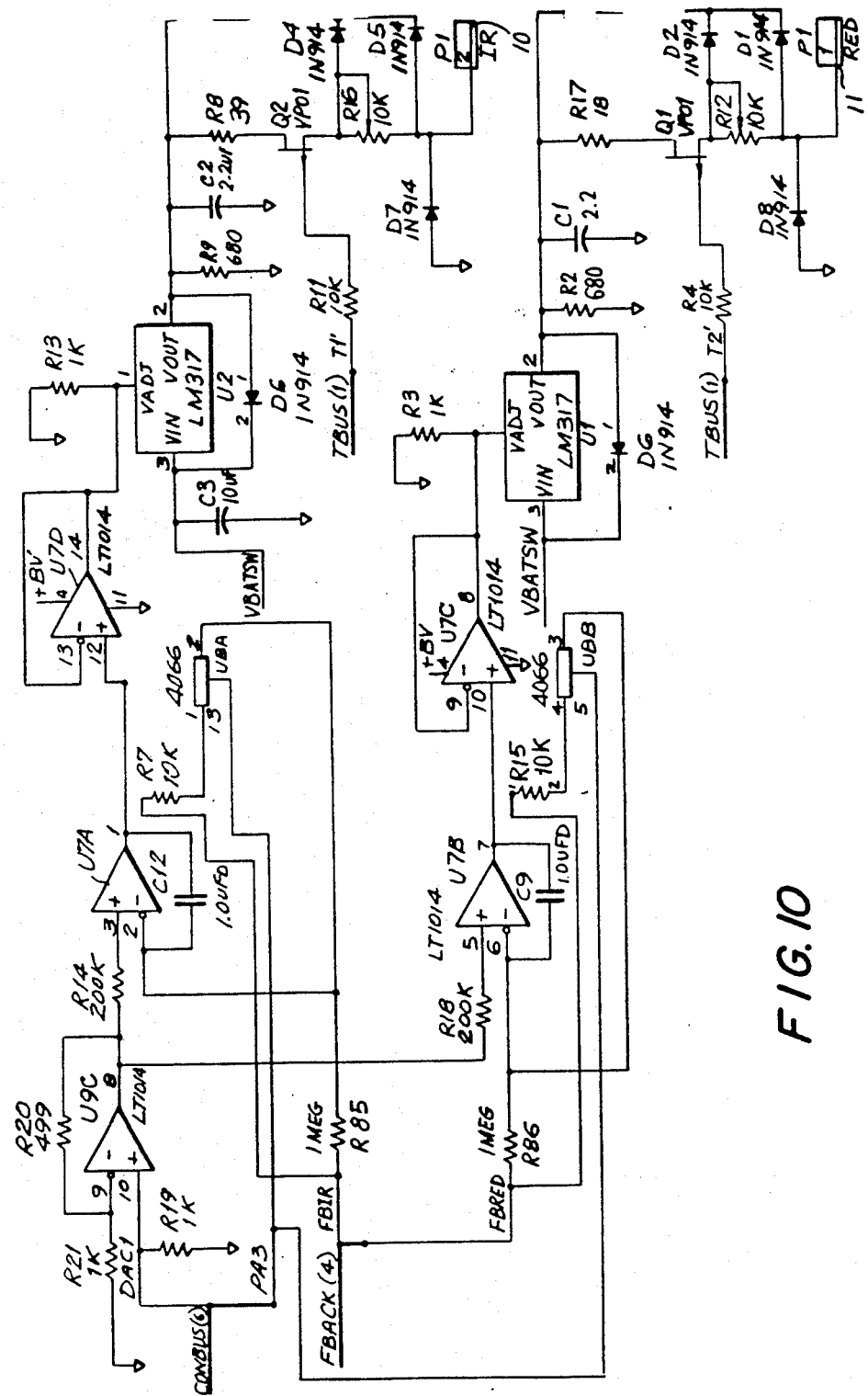
FIG. 10 is a circuit diagram of the circuits controlling the operation of the LED's.

The circuit of FIG. 10 is concerned with controlling the voltages applied to the IR and the red LEDs. DAC 1 is a signal from the connector bus, and ranges from 0 to 5 volts. This signal controls the level of brightness of the LEDs. It is amplified in U9C to give a signal that ranges from 0 to 8 volts to provide a little gain. The signal output of U9C is applied via a serial 200 k resistor to the non-inverting input of U7A and also via a 200 K resistor to the non-inverting input of U7B. This is part of a feedback loop and it forms an integrator which allows control of the brightness The other part of the feedback loop is feedback IR, which is the signal FBIR. This signal is applied via a 1 meg resistor, or alternatively via a resistor, to the inverting input of U7A, or into Pin 6 of U7B. When considering FBRED, the feedback red signal is similarly applied via a 1 meg resistor or alternatively, via a 10 k resistor, to the inverting input of U7B. U7A and U7B are connected as integrators with 1 mfd mylar capacitors C12, C9 forming the integrating part of these circuits. The time constant of the feedback loops can be changed by activating the 4066 switches U8A, U8B and paralleling the 1 meg resistors R85, R86 with the 10 k resistors R7, R15. This sets the integrator to a much faster mode for faster signal acquisition. This mode control is effected by the signal PA3, which is controlled by the microcontroller and permits changing the time constants, not only in the feedback loop, but as will be apparent, also in the bandpass filters .

The output signals of U7A and U7B are directed via voltage followers U7D, U7C, to the V-adjust input of LM317 regulators U2, U1. These circuits perform voltage control functions to produce regulated output voltages, controlled by the V-adjust inputs, with an upper limit of that is about 1.2 volts below VBATSW. R9 is a load to maintain the proper current output of the regulator, and smoothes the output. R8, R17 39 are current limiting resistors. Q1 and Q2 are switches to turn on the signals to the LEDs. The diodes D1, D2, D4, D5, D7, and D8 protect the FET's from static electricity or discharges that might occur in that area. The timing signals will be discussed in the following paragraph.

P1, pin 2 applies the signal to the IR emitter, and P1, pin 1 applies the signal to the red emitter. This is a voltage controlled signal.

Figure 11:
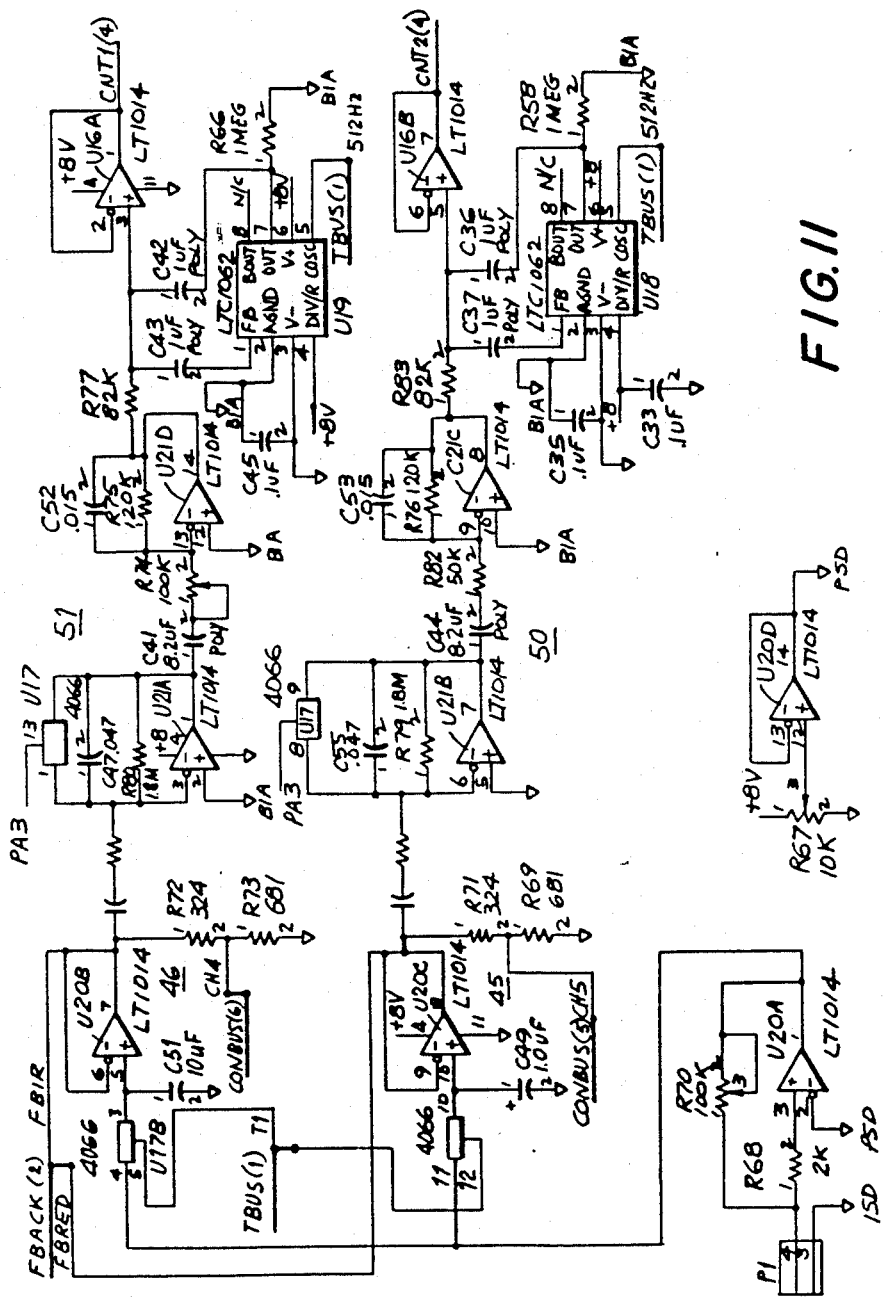
FIG. 11 is a circuit diagram showing processing of the output signals of the photodetector.

Referring now to FIG. 11 the photodetector input to the circuit is applied to P1, pin 4. This is the collector side of the phototransistor. Pin 3 is the isolated ground on emitter side of the phototransitor. R70 is a control potentiometer for the gain of the current to voltage convertor, formed by the Opamp U20A. R68 is a current limiting resistor to protect U20A from any inputs which may exceed the rails potential. The signal output of U20A are applied to a red sample and hold circuit 45 and an IR sample and hold circuit 46. The sample and hold circuits include the 4066 analog gates U17B, U17D, and capacitors C51, C49. The signals now are essentialy in the form of an AC signal riding on top of the DC. U20B and U20C are voltage followers to eliminate any loading of C51 or C49.

The signal output of U20B, U20C is essentially a DC signal with a small AC component, and that DC signal is fed back as the above-discussed FBIR or FBRED. These signals are also fed through a voltage divider back to an A to D convertor on the microcontroller board. This enbables checking to make sure that the DC levels are properly matched. It's crucial to the system to maintain a match between the Red and the IR signals in so far as their DC components are concerned. Becaue of thi, feedback is employed which maintains that match contant independently of any degrading of the parts themselves or any minor fluctuations that might occur in contacting the skin, etc.

The signals are now AC coupled via C40 and C39 to the first stages of bandpass filters, U21A, U21B. The feedpack paths of the filters, which include 1.8 meg resistors, must be shorted by analog switches U17 under the control of the PA3 signal. This makes it a lowpass filter and allows compensation for the DC component. PA3 from the microcontroller board, is the same signal that is used to control the signals from the feedback loop constant for faster compensation.

After filtering in U21A and B, the signals pass through very large polyester capacitors C41, C44 and serial resistors R74, R82 to a bandpass stage formed by U21D and U21C. After filtering in these stages, the signals are essentially AC signals. These signals are applied to LTC1062 circuits U19, U8 which are 5 pole lowpass filters, to eliminate any high frequency components. Since the LTC1062 circuits cannot drive substantial capacitive loads, their outputs are applied to a voltage followers formed by U16A and U16B.

Resistor R74 which is a 100 k potentiometer. This resistor is used to adjust the two stages U21C, U21D so that the levels of the IR stage, at the top of the figure, and the red stage at the lower portion of the figure, can be essentially matched. This matching is essential since the two bandpass filters, all of the filtering, all of the gain on our AC signal, must be identical in the two circuits. This matching may alternatively be effected in the microcontroller, to render adjustment of R74 unncessary, so that the unit can be calibrated by running a test program with a clibration header connected thereo.

Figure 12:
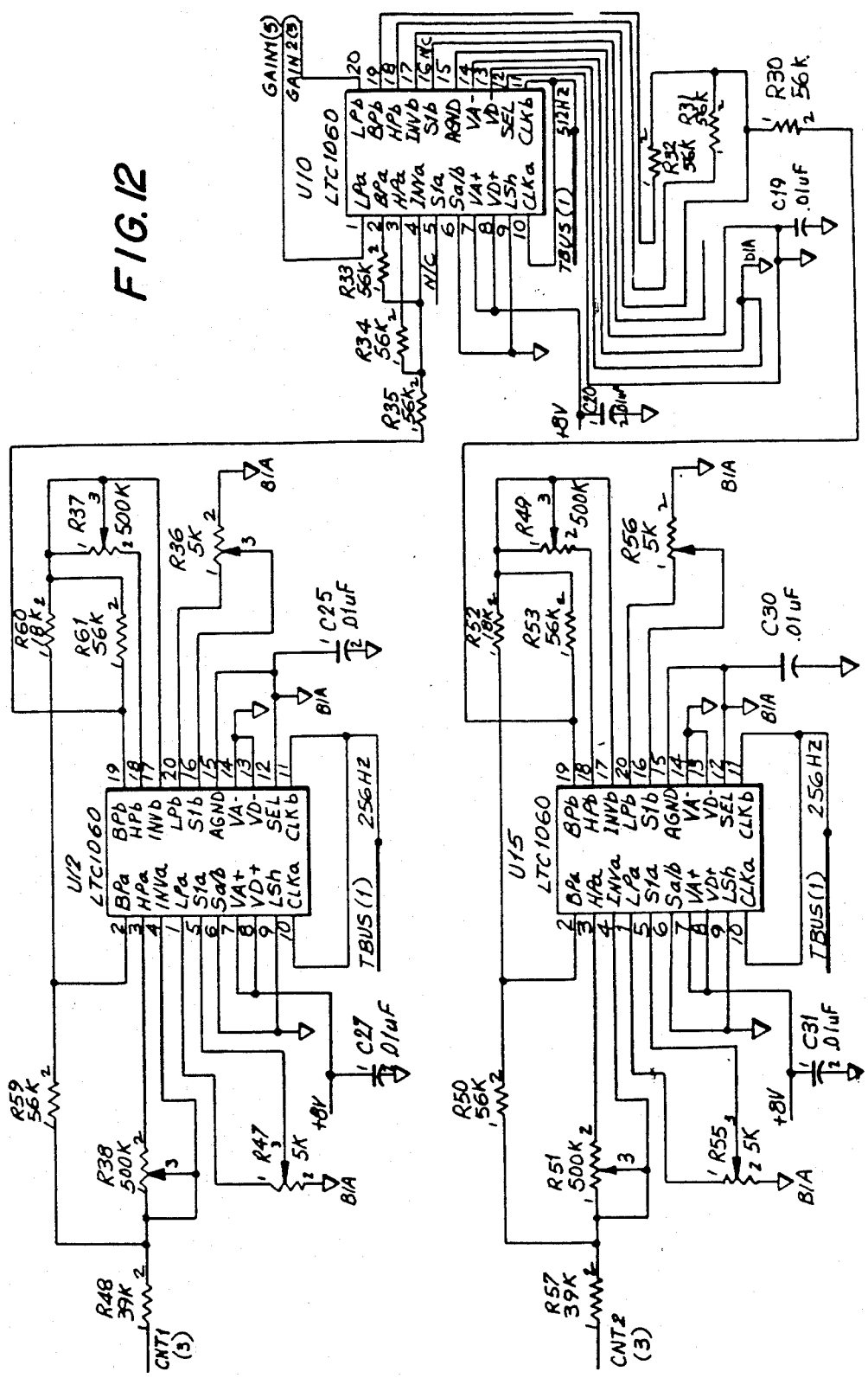
FIG. 12 is a circuit diagram showing part of the bandpass filters.

The signal outputs CNT1, CNT2 are applied to the circuit of FIG. 12. This circuit includes the bandpass filters, Linear Technologies LTC1060T—U12 and U15. These are 2-poled band or highpass/lowpass filters configured to have a gain of 56 over 39, in mode 3. The Q is adjusted by R38, R47 and adjusts the center frequency. The center frequency was set to about 102 beats per minute. The filter is used to just provide a few more poles on the high and the low end.

The Tbus signal applied to the filters is a signal which is at 256 hz that clocks these switched capacitor filters. The signal outputs of the filters U12, U15 are applied to a further LTC1060 filter U10. Once the signals have passed through these three filter stages, they exit the circuit as GAIN1 and GAIN2. U10 may have a gain of 1, and a Q of 1.

Figure 13:
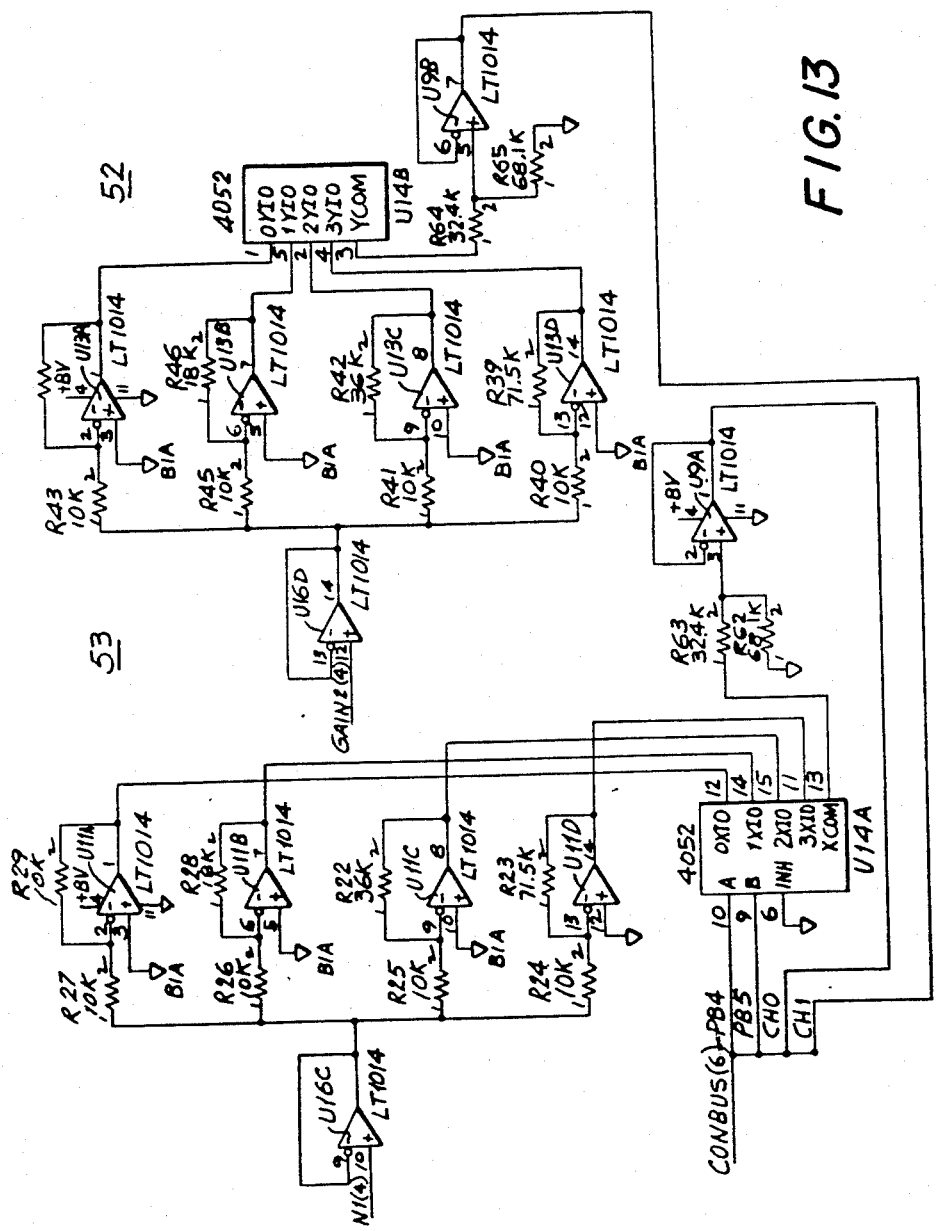
FIG. 13 is a circuit diagram showing the gain control circuits.

Referring now to FIG. 13 of the analog circuit, the RED or the IR signal pass through voltage followers U16D, U9D, and then are each applied to four stages of amplification, each with a different feedback resistor, so each gain is different. These gains in one example were 1, 2, 4 and 8, and in another example they are about 1, 1.25, 2, and 4. The outputs of these amplifiers U11, U13 are fed to 4052, i.e. a dual 4 to 1 selector, U14A, B. The selector is controlled by signals PB4 and PB5 from the microcontroller board. In this system, the 4 by 1 selectors are used to enables elections of any desired gain signal. While an adjustable gain system may provide the necessary adjustment function, such systems generally have too long a setting time. The present system, however, aquires the correct signals almost instantly. In the illustrated system, the 4 channels operate simultaneously and the desired one is picked using a 4 to 1 selector. The 4 to 1 selector also controls the RED signal. Both of these signals are fed to attenuators to have a 0 to 5 volt range, so that they can be read by an A to D (not shown), via the voltage followers U9A, U9B signal channels CH0 and CH1. These channels are viewed by an analog to digital convertor to determine what kind of signals they are.

FIG. 14 shows the connectors which goes to the main Board and the associated bypass capacitors. The 8 volt LED is for diagnostic purposes, to make sure that the board had the proper voltage.

Figure 15B:
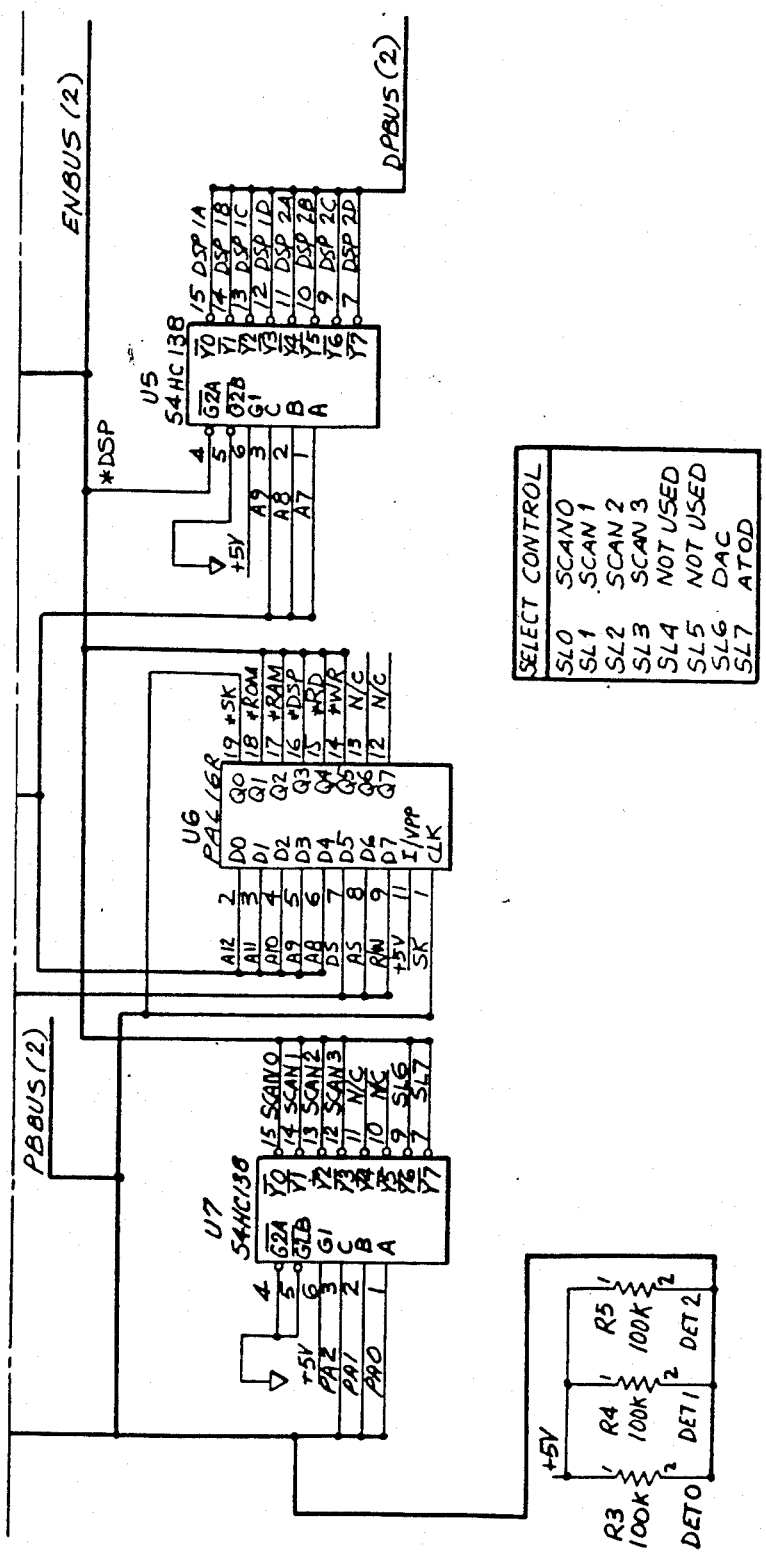
FIG. 15 is a circuit diagram of the digitial circuits of the system of the invention, including the microcontroller.

The digital section, as seen in FIG. 15 employs an 6805 8 bit micrcontroller cloced at 5 mHz.

Since the 6805 uses multiplexed address/data lines, a 74HC373 latch U2 is used to separate these signals. U3 is an 8 k ×8 ROM. A 2 k× 8 RAM U4 provides room for storing the variables, etc. U7 may be us ed for keyboard scan, if desired. The EP310 U6 is a programmable logic device for decoding the RAM and controlling the display. U5 is further decoded to get a display bar signal to allow breaking the addressing into 8 segments for controlling an LCD dis play.

FIG. 14 shows the A to D convertor, U8, which is a serial device, preferably an 8 bit, 8 channel A-D serial device. It is selected by the signal SL7. The other serial device in this figure is a 6 bit, 6 channel DAC, U9, used to generate signals and control the beep and alarm volume, etc., and also the bypass capacitors and the indicator LED.

Figure 16:
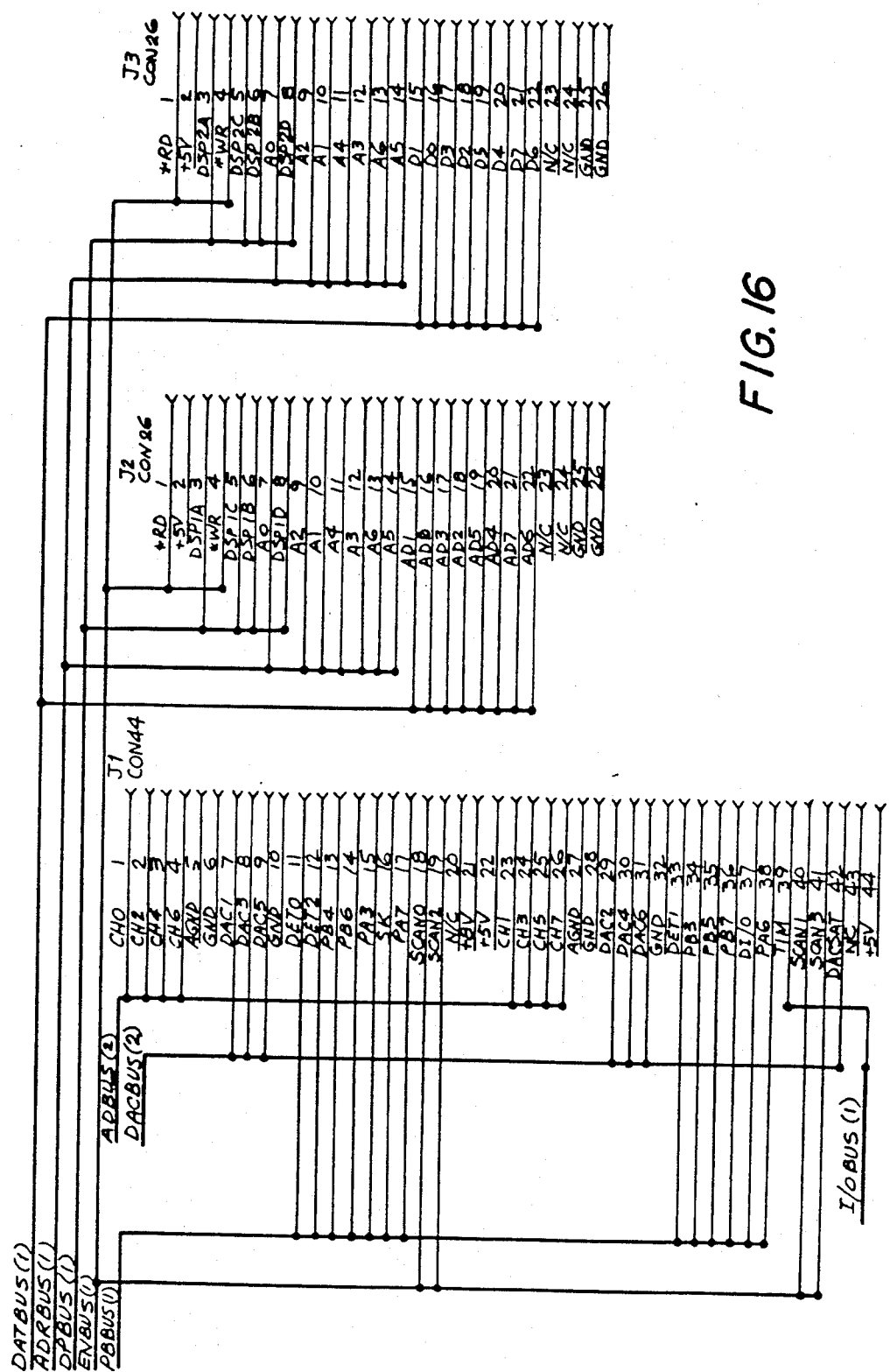
FIG. 16 is an interconnection diagram.
Figure 17:
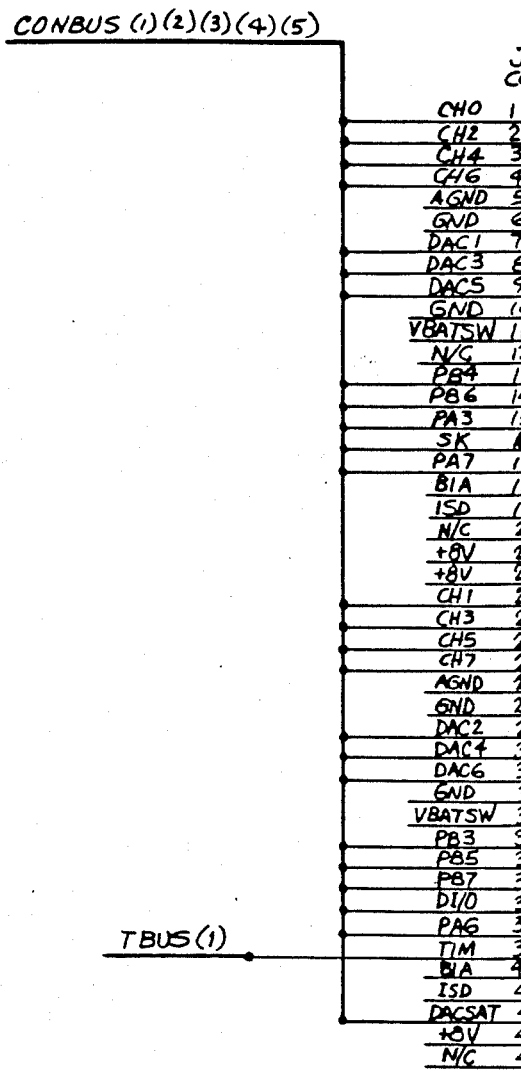
FIG. 17 is a further interconnection diagram.

FIG. 16 shows the connections to the display, etc. J2 controls the display.

Figure 18:
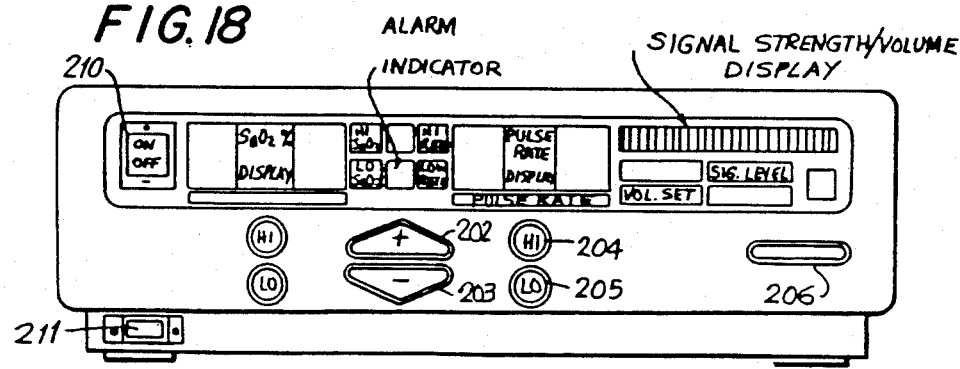
FIG. 18 is a front view of the control panel.

Considering now the front panel and the schematic for the display boards as seen in FIG. 18. The front panel has essentially 7 keys. Key 200 is for setting the high saturation limit. Key 201 is for setting the low saturation limit. In the center of the unit a key labelled "PLUS" implements the limit. A key 203 labelled "MINUS" decrements the limit. The plus and minus keys can also be used to control the volume. Next to the PLUS and MINUS keys, under the pulse rate area, a key 204 is provided to set the high pulse rate limit and a key 205 is provided to set the low pulse rate limit. On the far right hand side of the unit, an alarm mute key 206 is provided. This key's function is to mute the alarm when it is functioning for a period of 30 seconds. By simultaneously pushing the alarm mute key and the PLUS and MINUS key, the alarm volume can be set and/or turnd off completely. If it is turned off, an indicator on the front panel will indicate an alarm off situation and continue to flash. An on/off 210 switch is located on the far left of the unit and a patient/cable connector 211 is provided in another area. All of the functions on the keyboard and the display must be controlled by an 8279 keyboard display controller interfaced directly to the microprocessor through connector J2 on the microprocessor board.

Figure 19B:
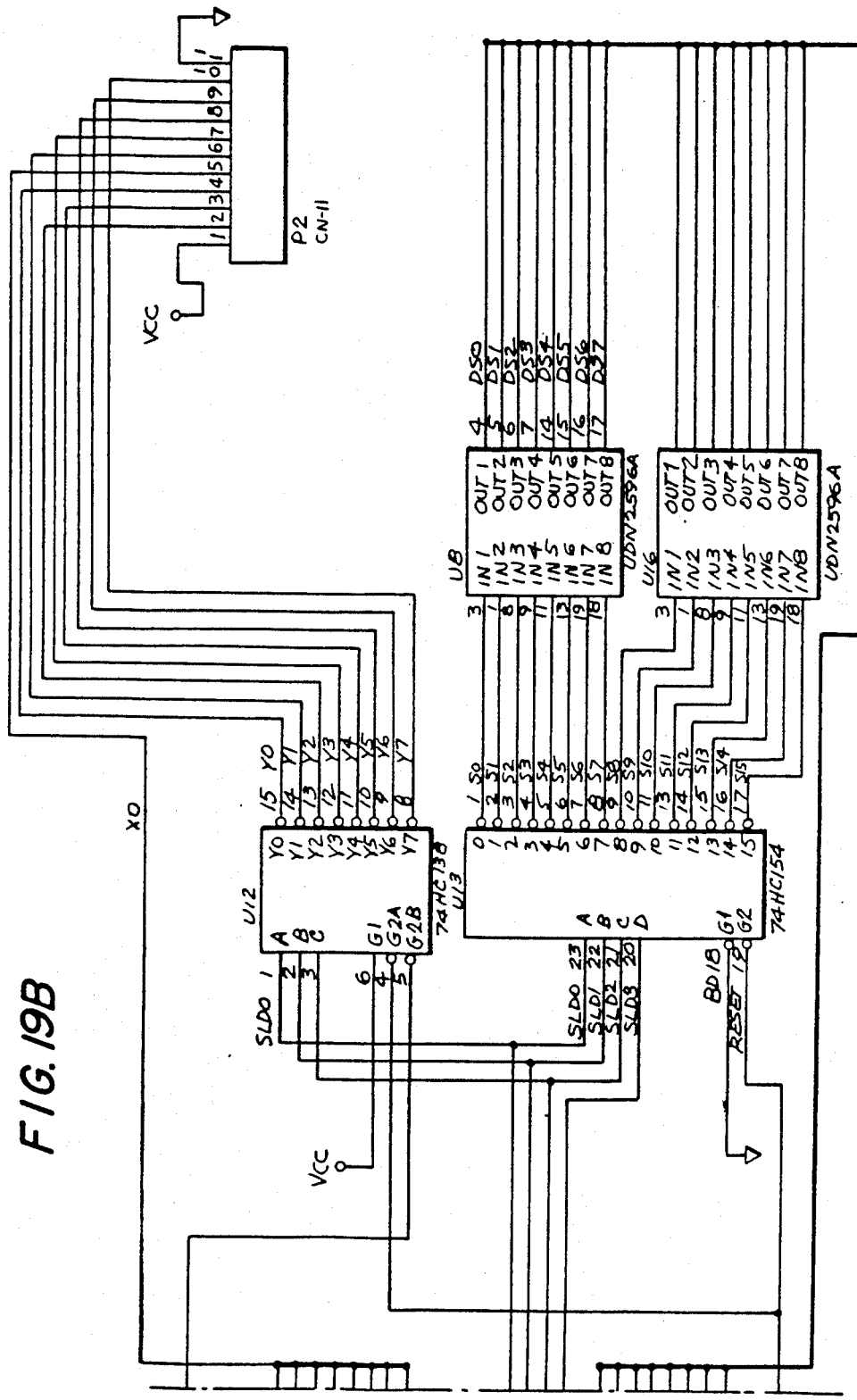
FIG. 19 is a circuit diagram of the display panel.
Figure 19C:
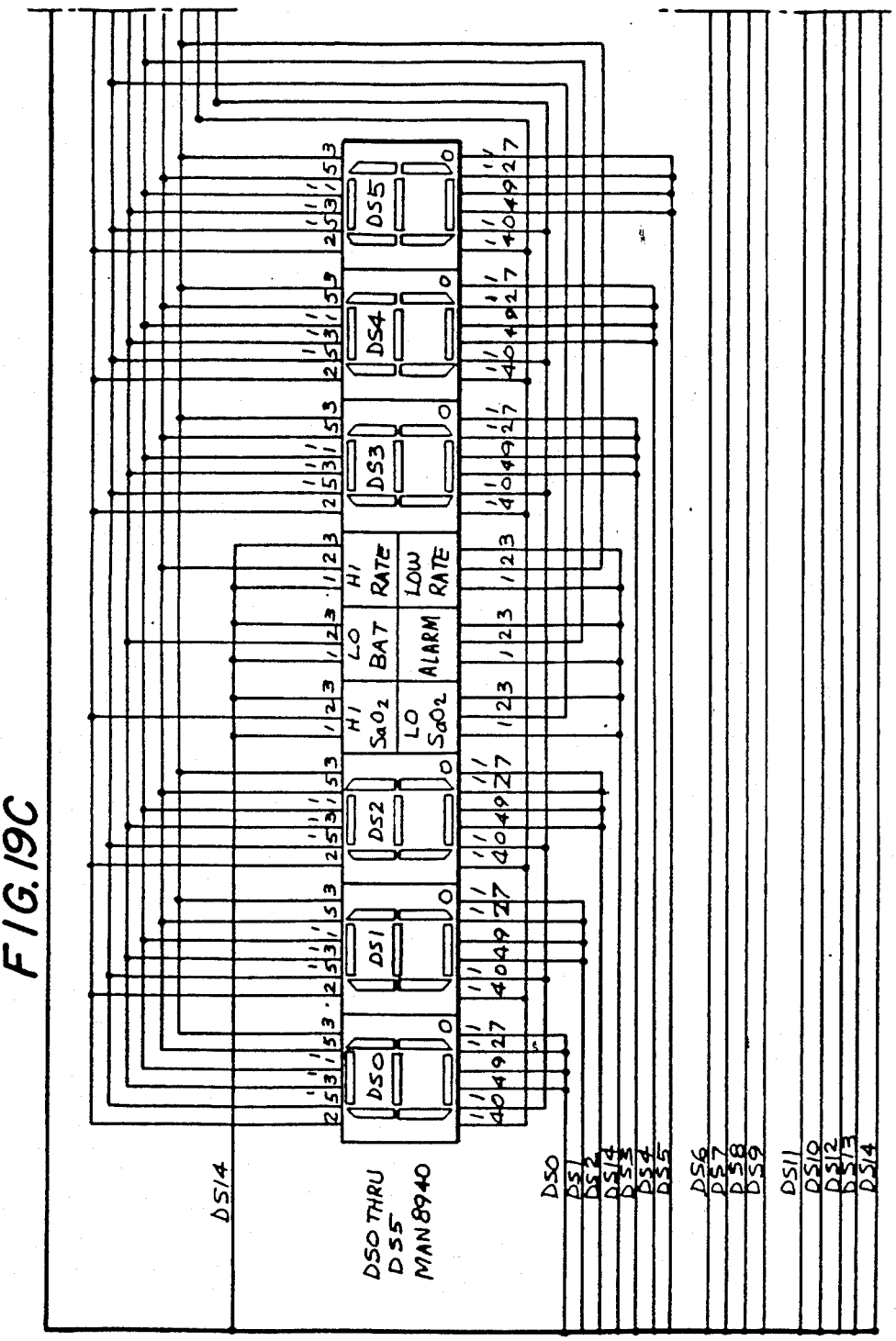
Figure 19D:
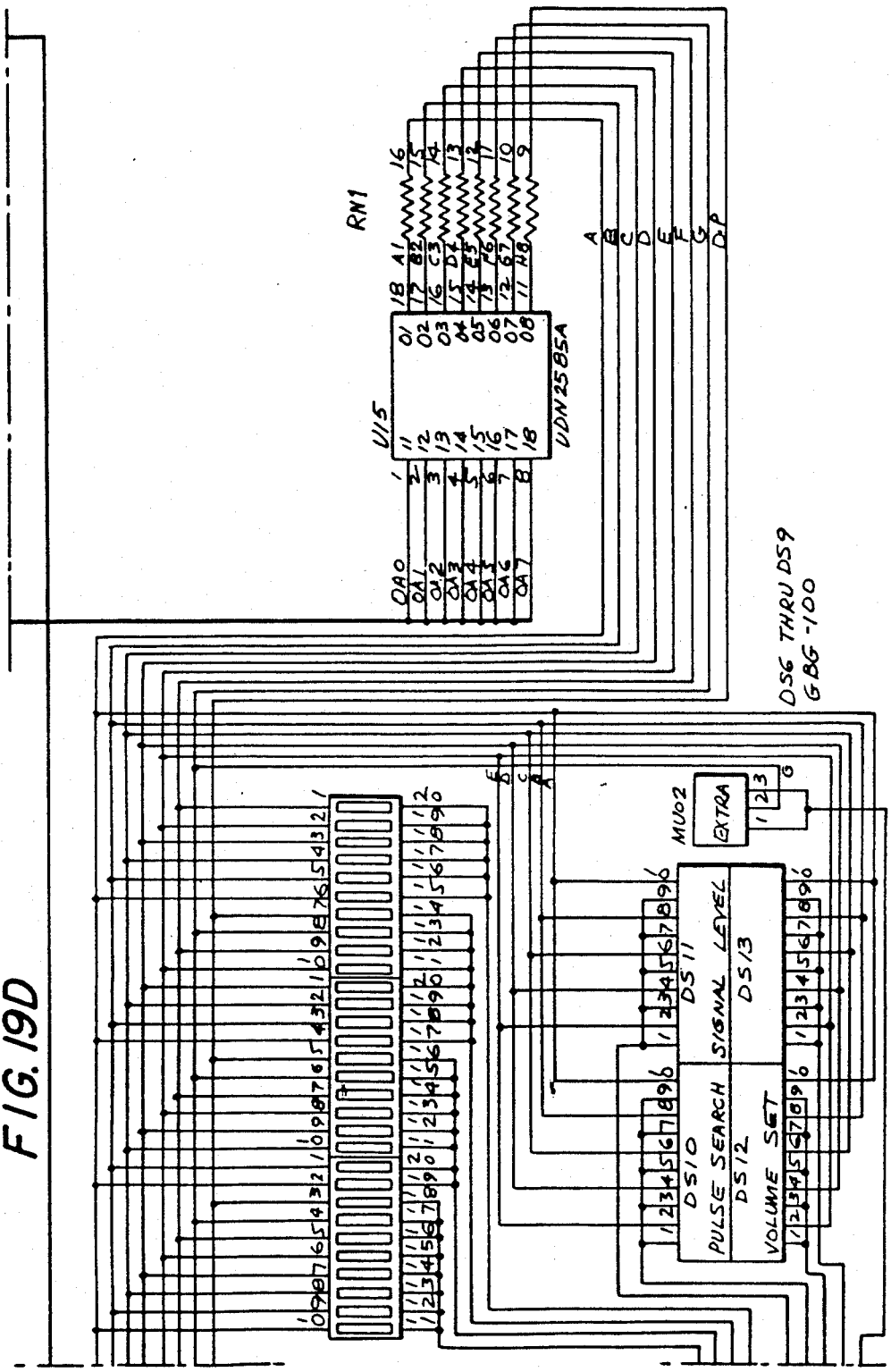
Figure 20:
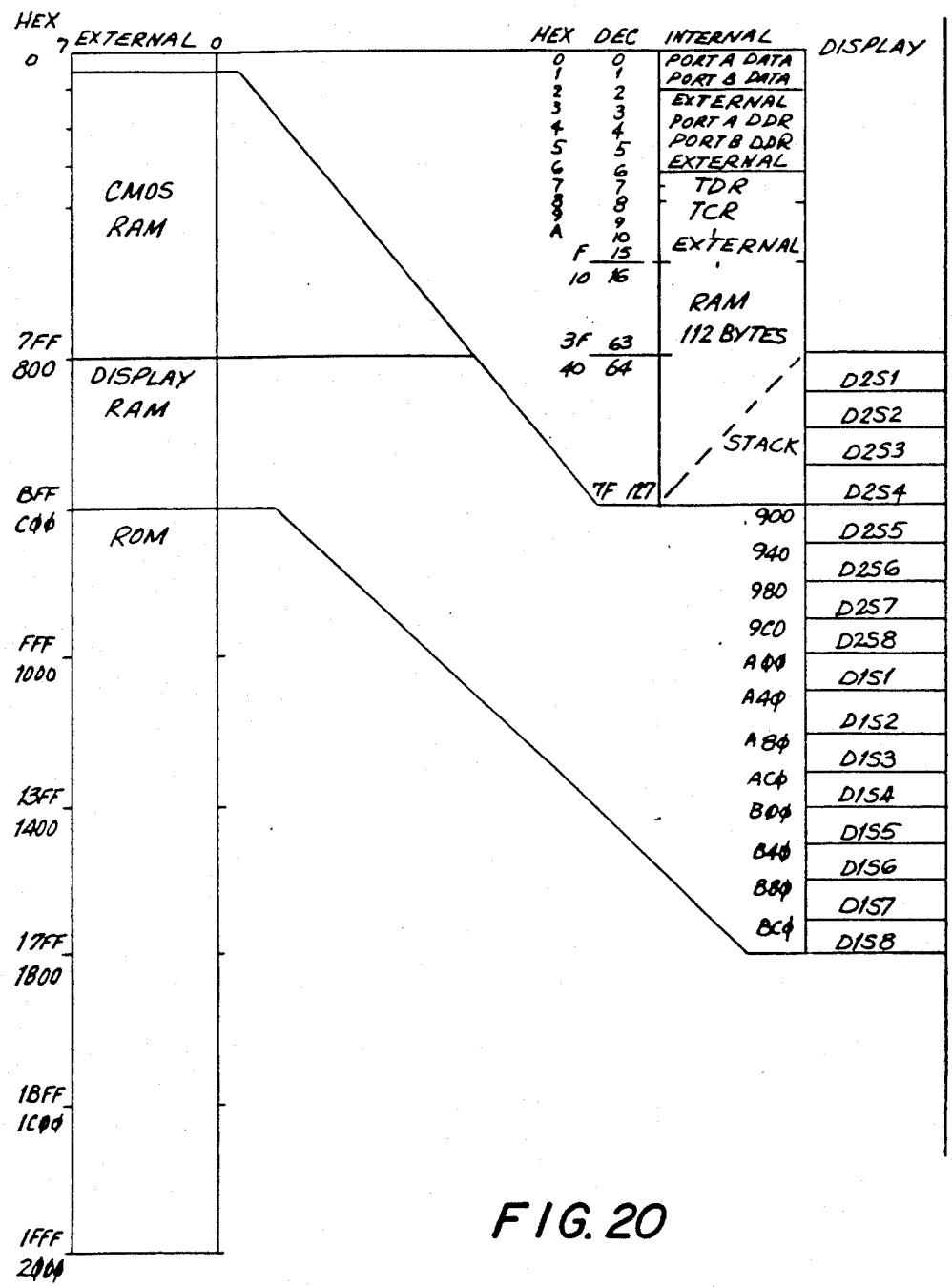
FIG. 20 is a memory map of the microcontroller.

Referring to the display schematic FIG. 19 7 segment displays DS0 to DS2 are used to indicate the saturation number and also the saturation limit when in the limit set mode. DS3 to DS5 are used to show the pulse rate in numerical values. The saturation value is a percent of the saturation—100% being fully saturated. In the center of the unit, 6 light bars are used in conjunction with the alarm set to indicate the set limit, whether it's a high Sa02, low Sa02, high rate or low rate, and also to indicate when those limits have been exceeded. High saturation will flash, for example, if the high saturation limit has been exceeded. Also the number for the saturation will flash.

Two annunciators in the center of the FIG. indicate a low battery condition, where power is low to go into a battery conservation mode. The lower center indicator indicates an alarm condition when the alarms are turned off, thus giving the user a visual indication that the alarms have been disabled. The unit also has 4 larger light bars; one is to indicate a pulses earch mode, another to indicate a volume set mode when the volume levelis being set. Still another indicates a display of a signal level. When in a pulses earch mode, the unit actually looks for a pulse signal; once that signal is found, then the system switches to the signal level area. Volume set shows when the bar graph is being used to indicate the volume level. When trying to decrease the alarm volume level all the way down until not a single bar is left, that is, an alarm off condition and the alarm light will flash continually indicating this condition, so it will not make any noise. The bar graph is a visual indication that that level is completely off. The bar graph is located over the ∝ indicators just mentioned, and indicates a signal level during normal operating mode, during pulse search it does not indicate anything. In the volume set mode it indicates the volume level, with the bar graph lit completely from left to right. The keyboard is scanned every 5.2 milliseconds and the display is updated every 10.6 milliseconds, thus eliminating flashes, etc. This is a very bright display which has the capabilities of recognizing two key pushes which is needed for alarm use and then continuous key pushes which is used for the volume set, plus or minus.

PROGRAM AND FLOW CHARTS

Figure 21:
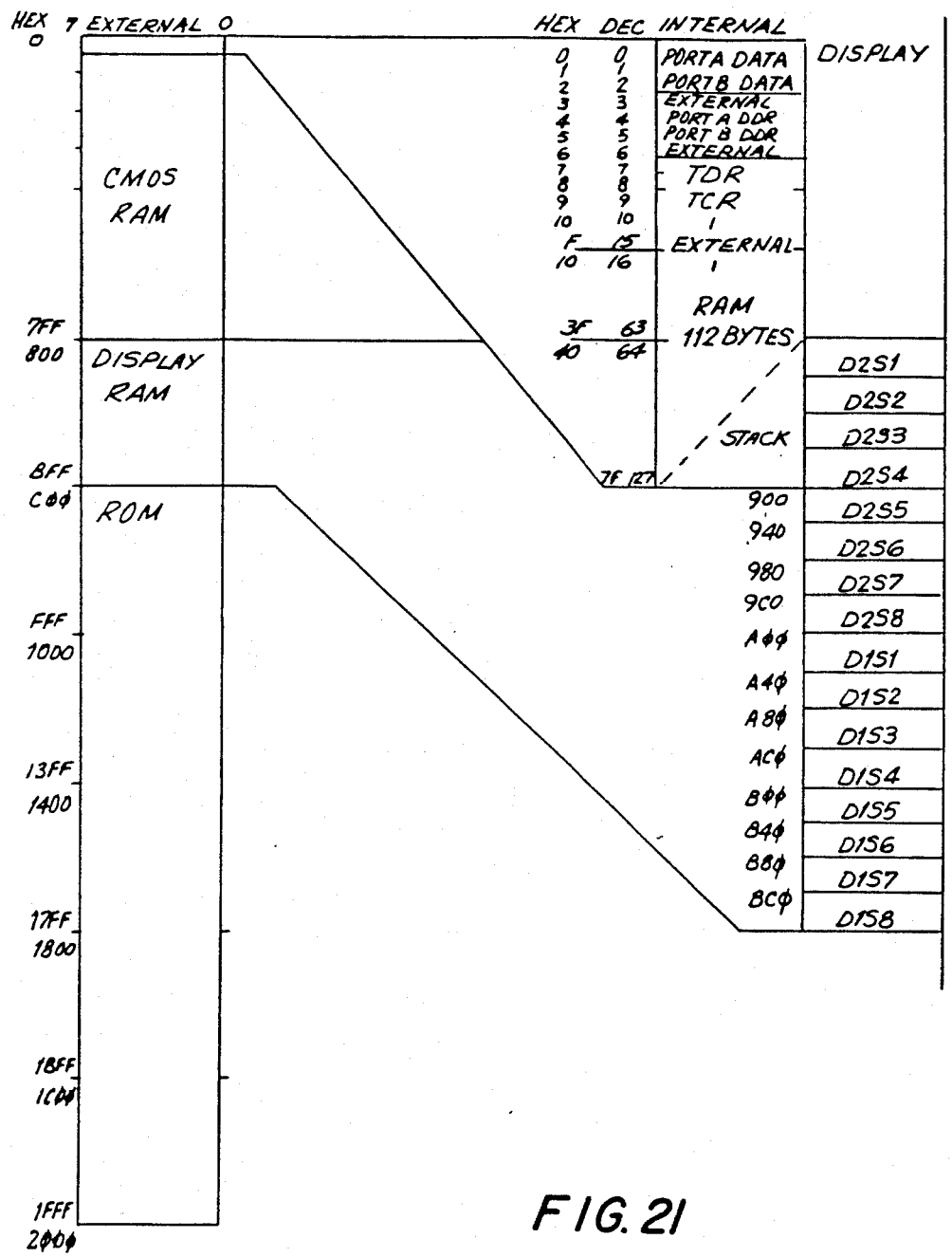
FIG. 21 is a memory map of the system.

The memory map of FIG. 21 essentially shows the interal configuration where we have our C-mos RAM where the display RAM is and also where the ROM starts, which is C000 through 1FFF.

FIG. 22 is a is table of contents showing limits that are set up and used in several areas controlling counts for key debounce limits for the signal acquisition, etc.

Figure 23:
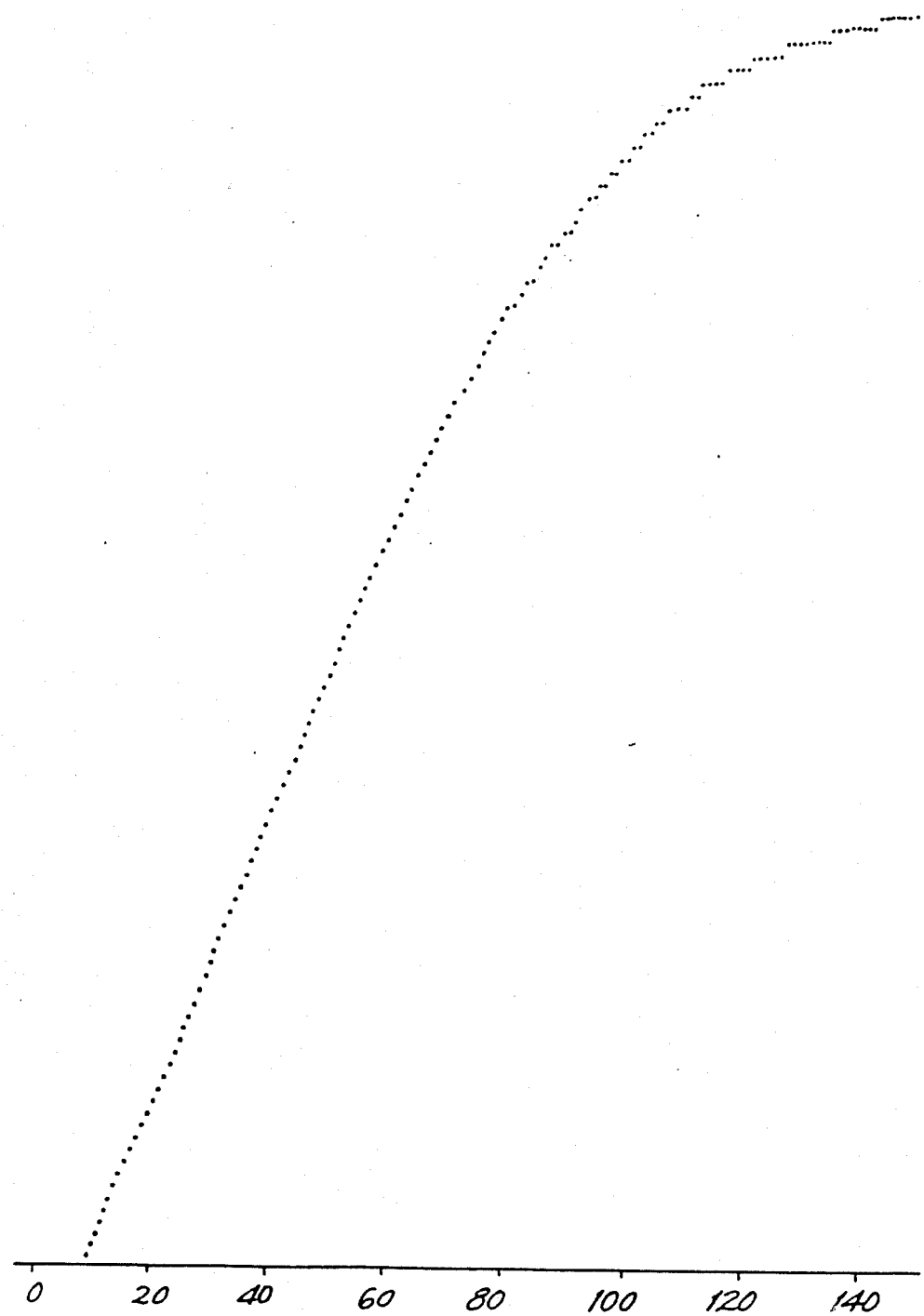
FIG. 23 is the Oximeter look-up table.

FIG. 23 is the oximeter lookup table which holds the lookup values for the oximetry calculations. This is the table the program accesses to lookup the oximetry percent after a simple divide on the numbers. When IR channel and Red channel have the same magnitude in their AC waveforms, a value of 96 is obtained. This value can be used for calibration purposes.

FIG. 24 shows a timing circuit which may be employed, although the timing is preferably in software for a total synchronous system.

Figure 26:
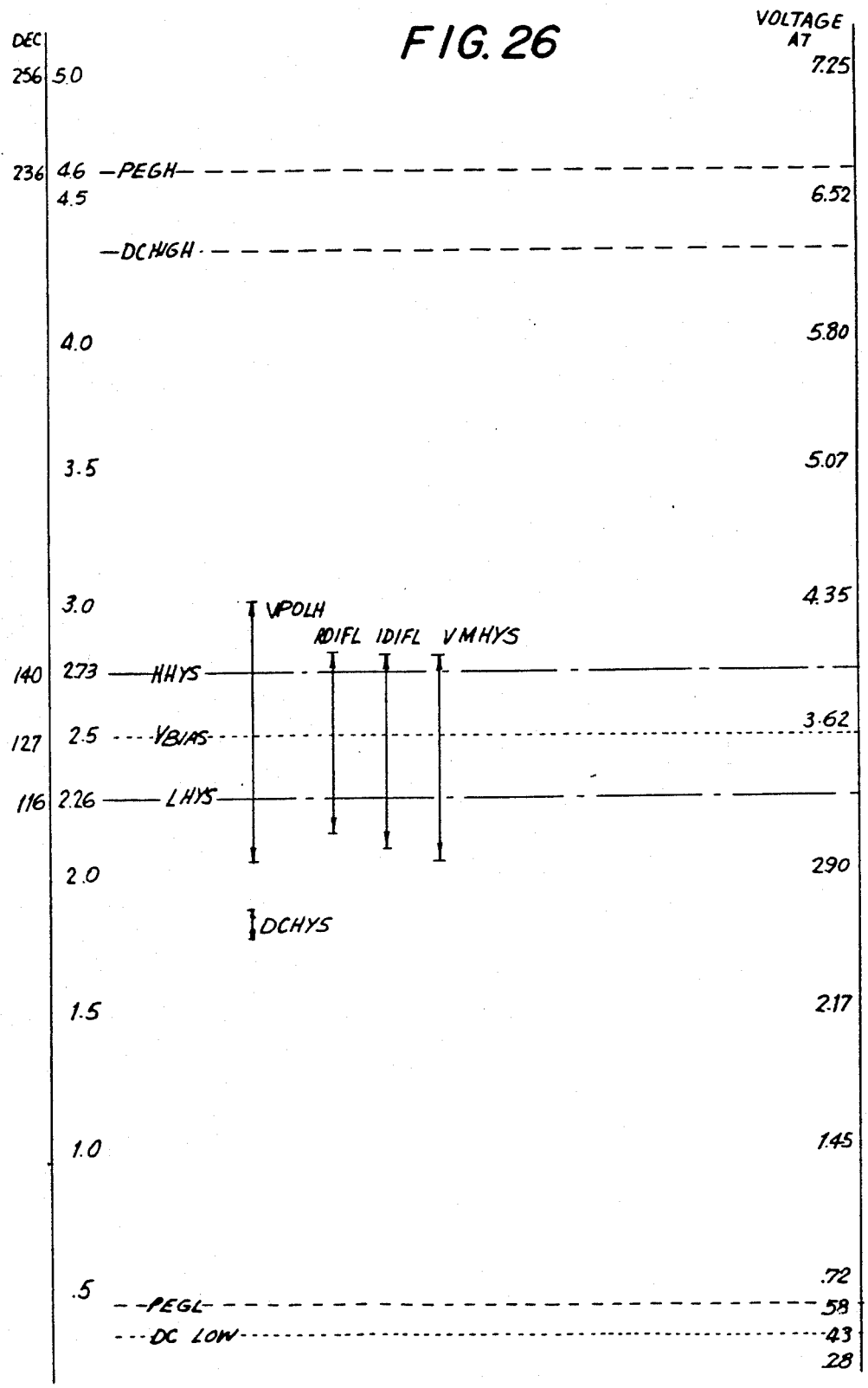
FIG. 26 is a diagram illustrating constant levels.

FIG. 26 shows the timing sequence that is used. In this FIG., for example, the Red LED is turned on with signal T1' and then sampled with signal T1. The signal T2' is the IR signal, and the sample and hold the gate for IR is opened only during the high state of T2 to look at the signal present at a given time.

Figure 27:
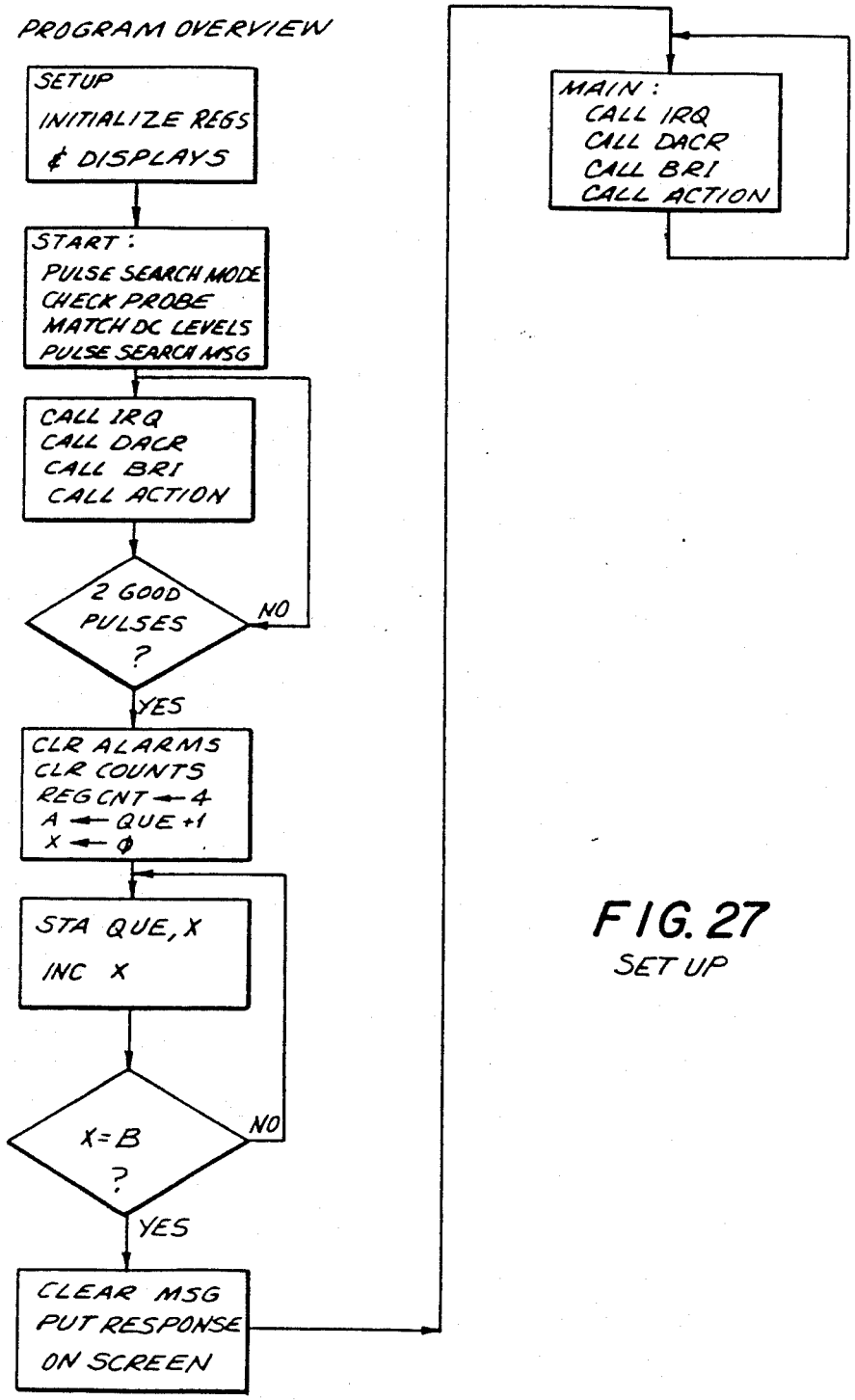
FIG. 27 is an overall flow diagram for operation of the system.

FIG. 27 is a chart showing some of the constants. On the left side is the decimal value and at the right side is the voltage. For example, decimal 256 gives a voltage at the A-D of 5 volts, the voltage at the op amp would be about 7¼. DC high is at 4.3 volts at the A-D. PEGH and PEGL are the limits that are used to determine when the signal is too large and pegs or rails. When it crosses out of that range, the AC signal is not counted, because some of the important data may be lost.

DC high is a setting such that the DC voltage coming back from the LED cannot exceed this upper limit. By the same token, DC low is the lowest point the brightness value is permitted.

At the center of the page, valid pulse height VPULH is the height of the pulse that is preferred. The minimum difference between max and min on the red is defined as RDIFL that's the lowest the red difference is permitted to be.

IRDIFL is the IR limit and VMHYS is the vector motion hystersis.

Essentially, the pulses hould be PULH high, which is about 2 volts or more high. A variance between the two signals 1½ volt is needed to trigger the vector motion detection. Dotted lines HHYS which is a high hysteres is level and LHYS is the low hysteres is level. These two lines are the lines which must be crossed for a valid pulse detection. Pulse detection requires that going above the HHYS line and below the LHYS line. V BIAS is the voltage that is us ed to reference the other voltages, and is about 3.62 volts.

The software has four main aspects:
(1) Acquis ition of Data from signal
(2) Qualification/control of the signal
(3) Data Computation and output
(4) User Interface/control of alarms and limits The acquisition of a signal requires a routine which in a real time mode meas ures the AC signals, both IR and RED. This is achieved by the routine called IRQ which is executed at a rate of about 256 Hz. The IRQ routine als o determines if the value is the highest of lowest value detected so far in this pulse. It also checks to see if this pulse waveform crosses the hysteres is limits and if so sets a flag for the computation routines.

Qualification of the signal is an ongoing process which checks for various conditions which nullify the saturation computation. These conditions are:

(1) A signal, either RED or IR, which does not correlate with its counterpart by the $\overline{\text{VMHYS}}$ amount. This kind of signal caus es the vector motion flag to be set.

(2) An AC signal which is close to the output limits of the OP AMPS is probably distorted and must be discarded. This condition is called OP AMPS pegged high or pegged low and sets the appropriate flag. Finally a signal which is too small cannot be used to compute saturation accurately and must be discarded. These qualifications als o trigger the control of channels on the 4 to 1 max and brightness levels of the emitters. For example a pegged signal is too large and the channel must be changed to lower again or if the signal is at the lowest gain, brightness level must be reduced. Conversely a signal which is too small must have more gain or if the gain is as high as possible, more brightness.

With each puls e the puls e rate mus t be determined and this is done in the routine $\overline{\text{Pulser}}$ by making the computation 7680 counts per minute divided by counts per beat to get beats /minute. If the qualifiers are all satisfied, then saturation is also computed. This computation occurs twice per pulse and takes IRDIFF/RED DIFF which is us ed for determining the fractional result for the look up table vector.

Finally the system can utilize any conventional method of output to the us er whether LCD, LED or some other state of the art display. Als o the us er must be able to set alarm limits, control BEEP and ALARM volume and shut of the alarm. The keypad or other state of the art controls are used and monitored by the software in a known or useful manner.

Figure 28:
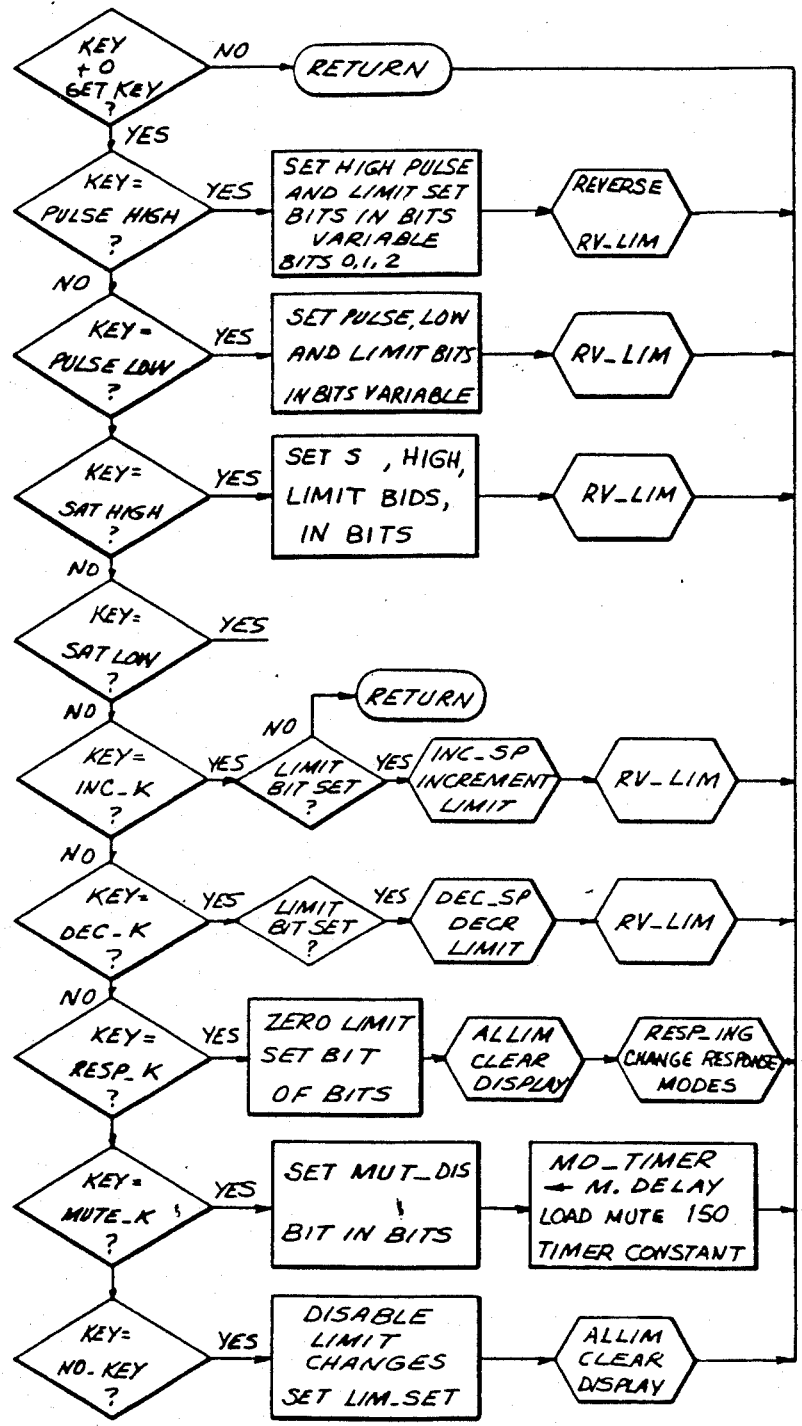
Figures 31A, 31B:
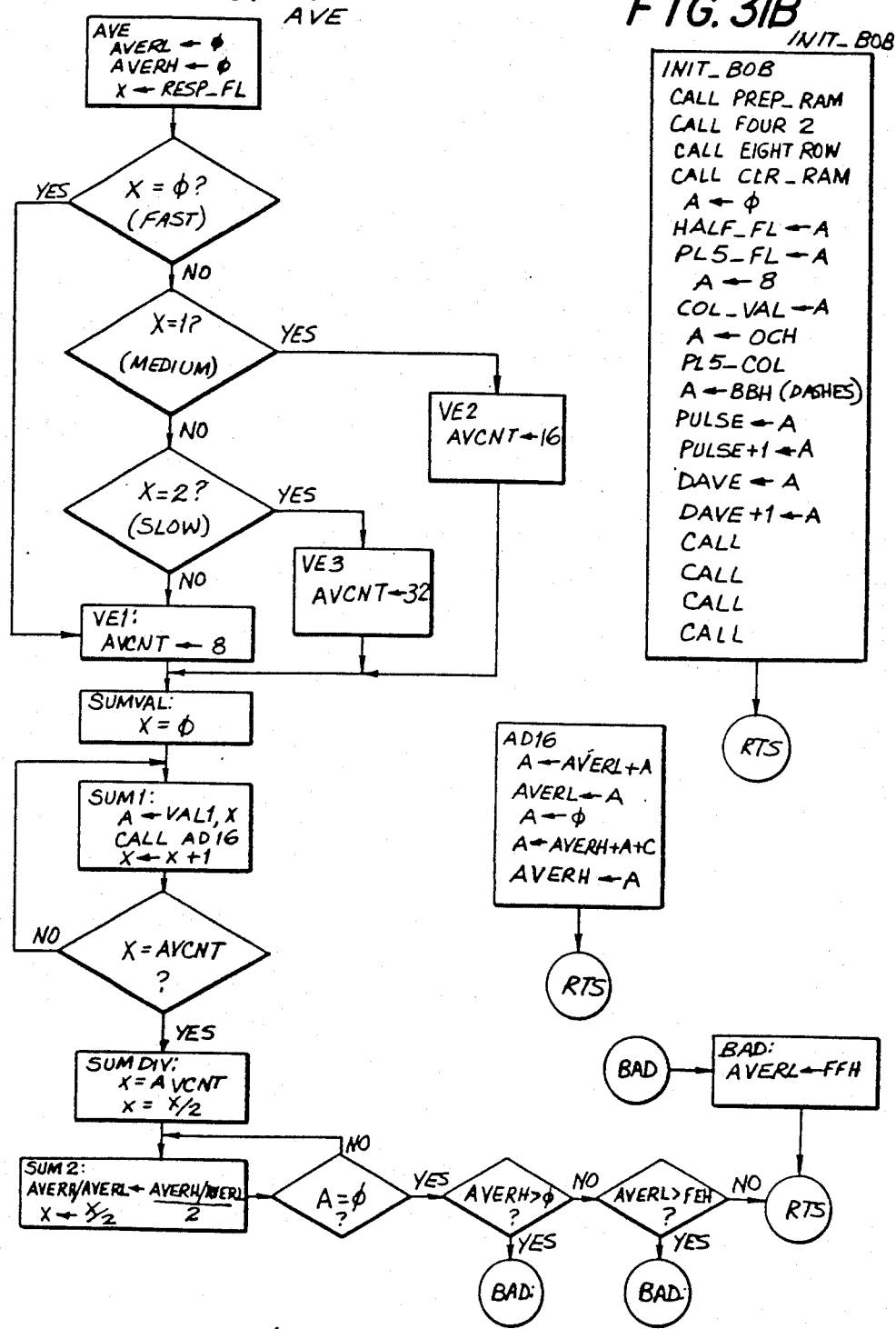
Figure 32A:
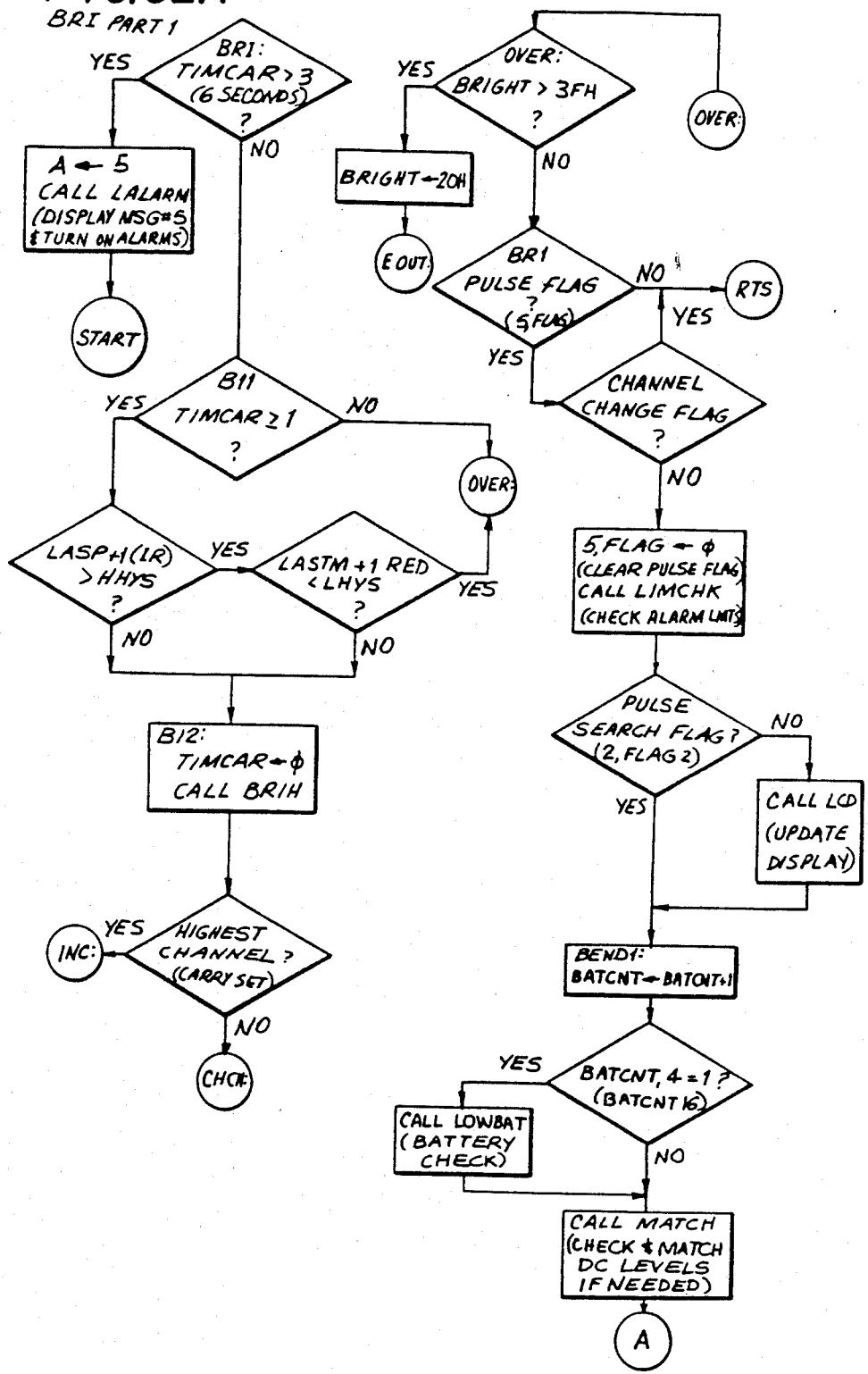
Figure 32B:
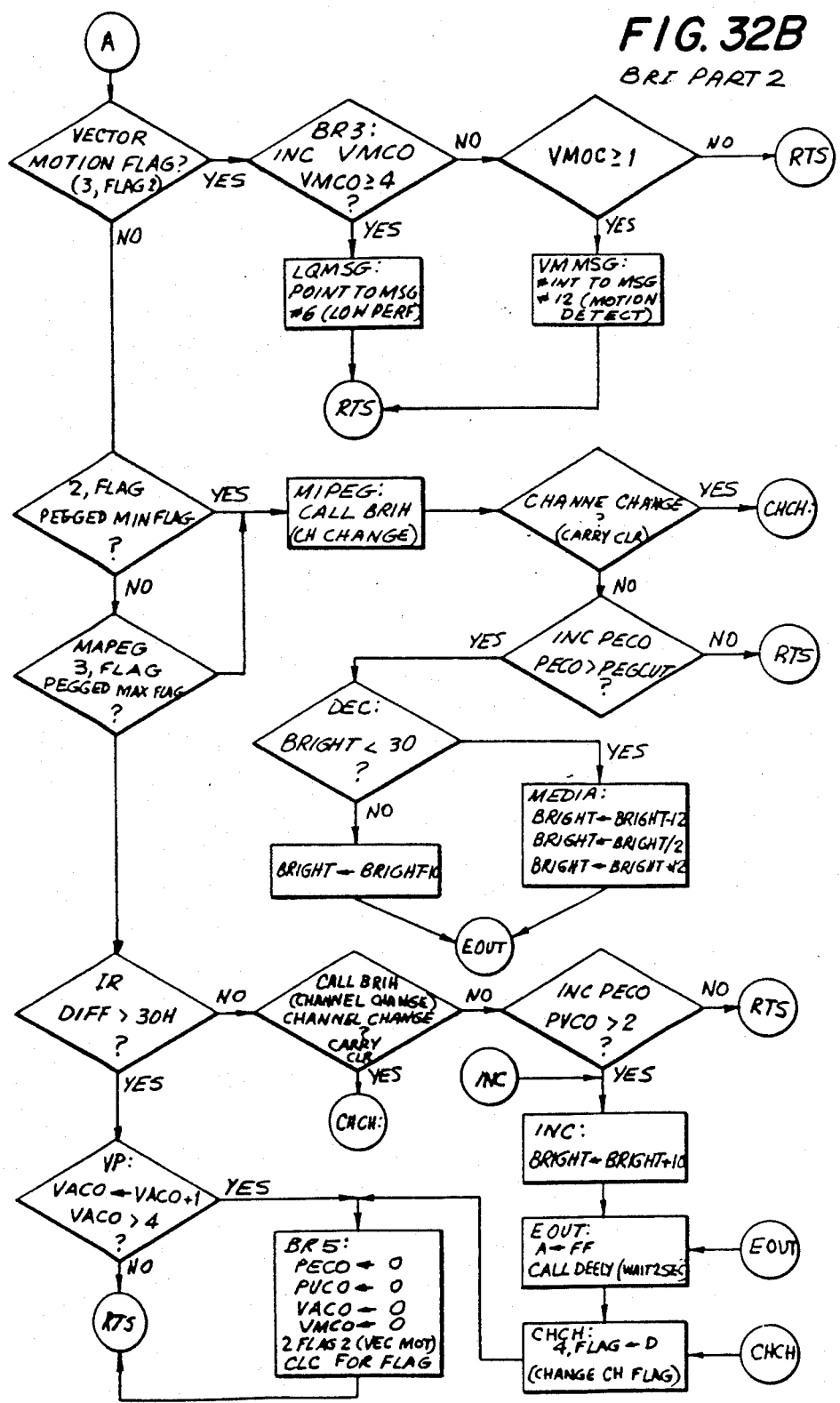
Figure 33:
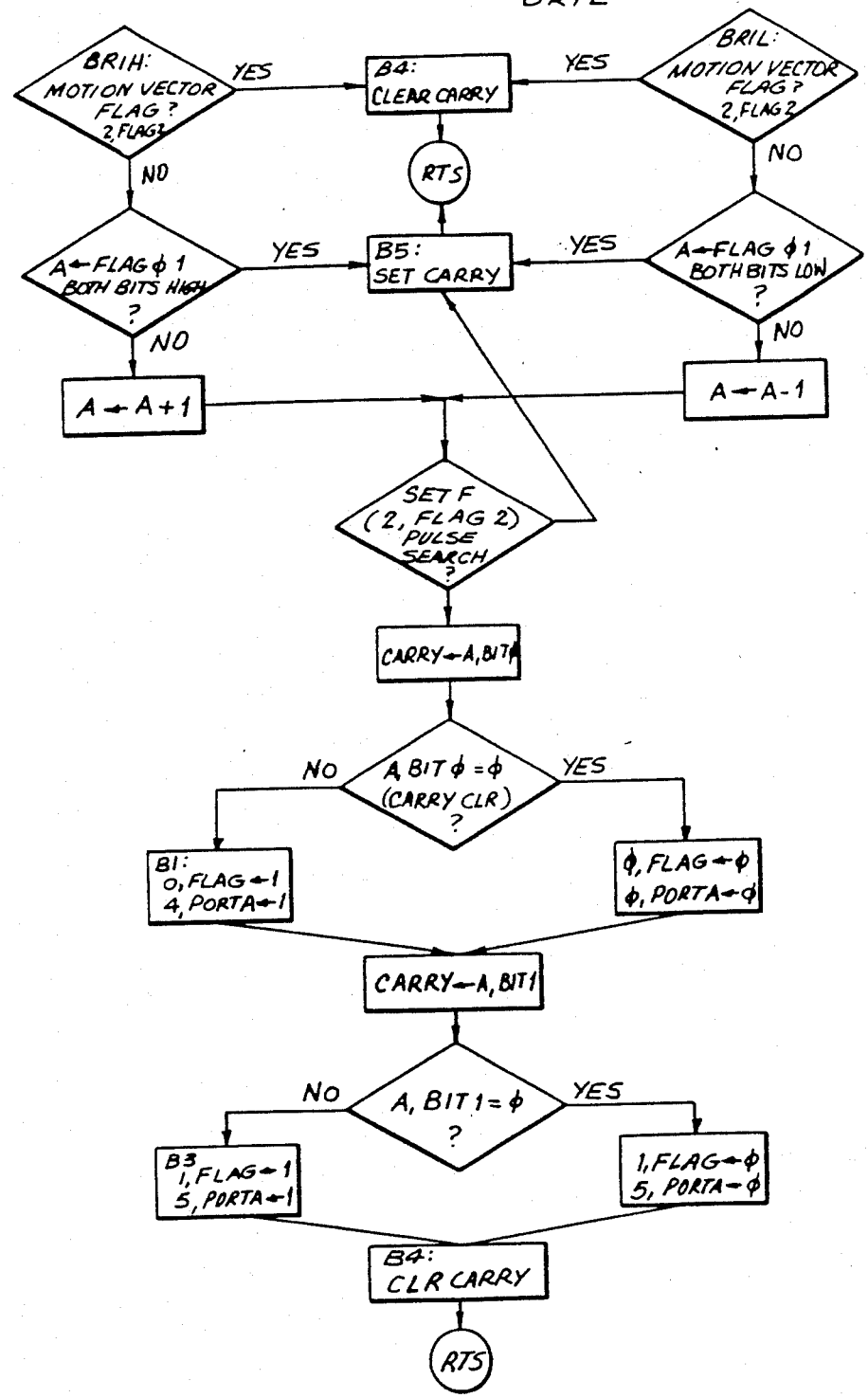
Figure 35A:
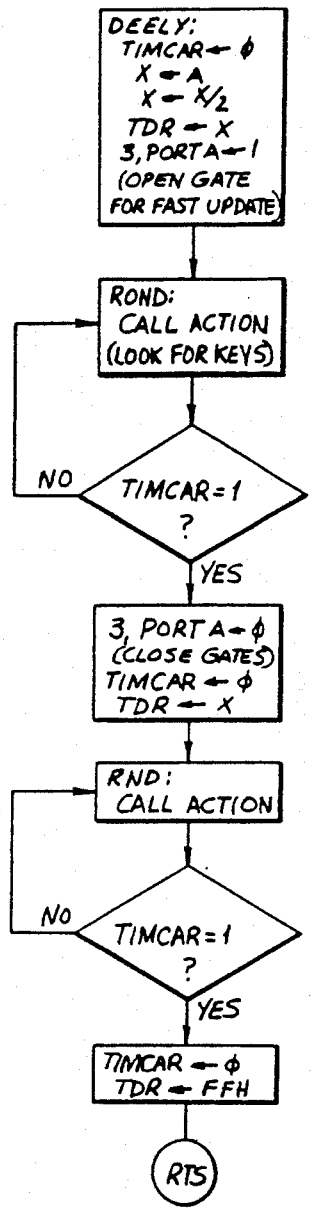
Figure 35B:
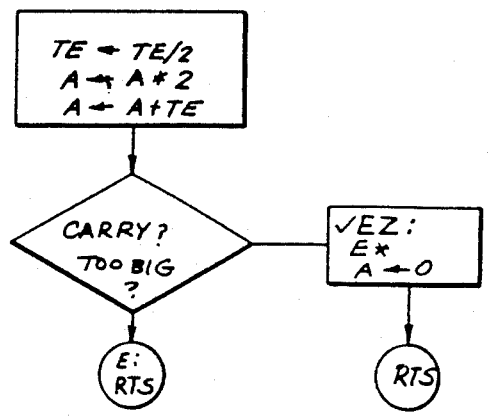
Figure 36:
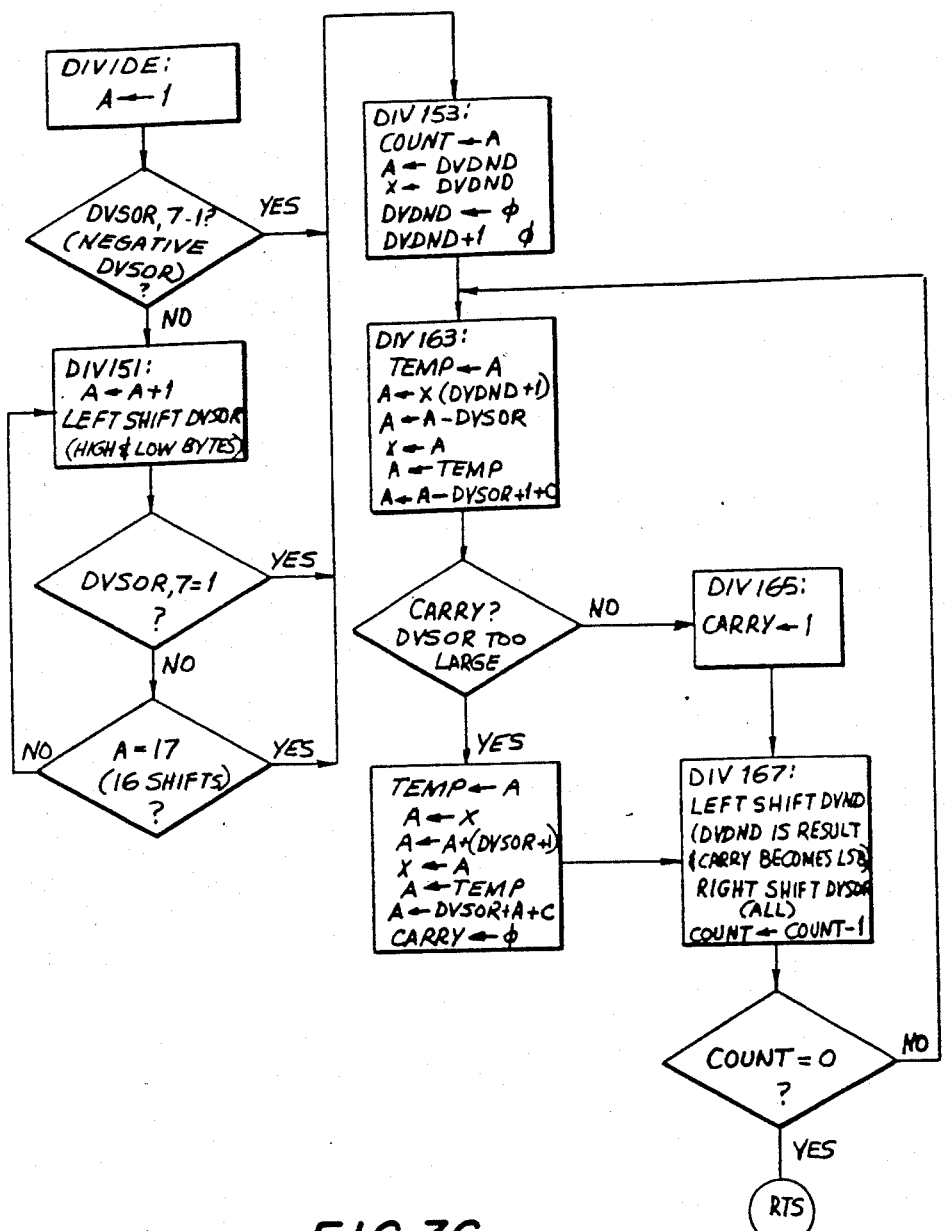
Figure 37:
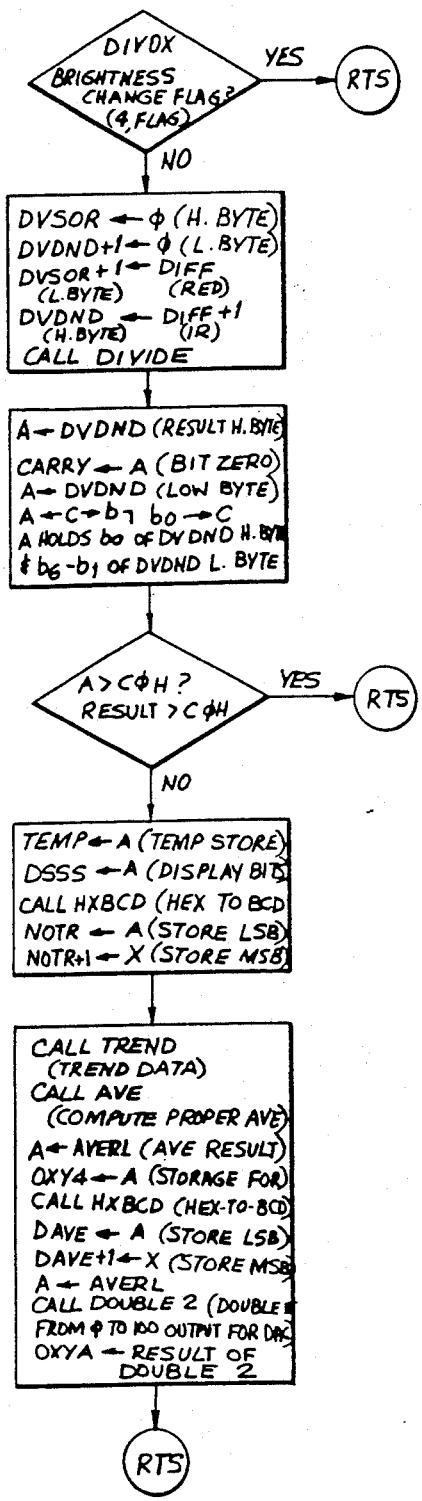
Figure 38:
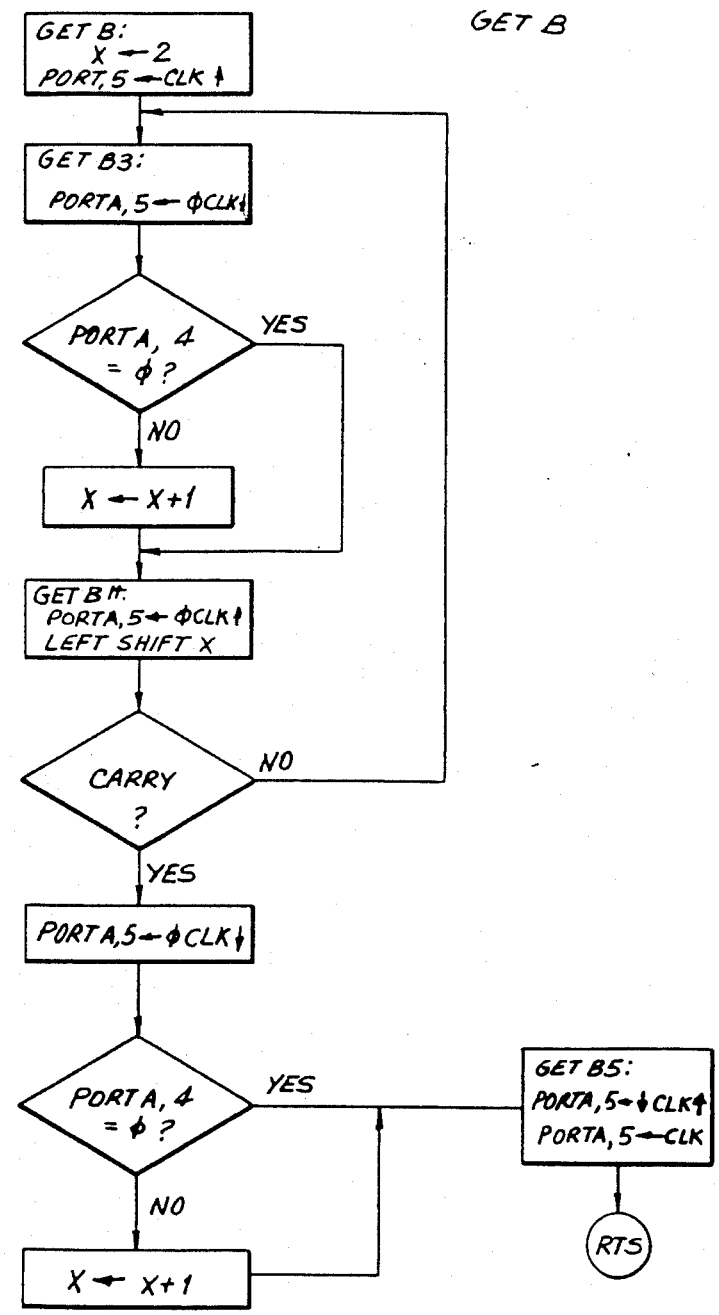
Figure 39:
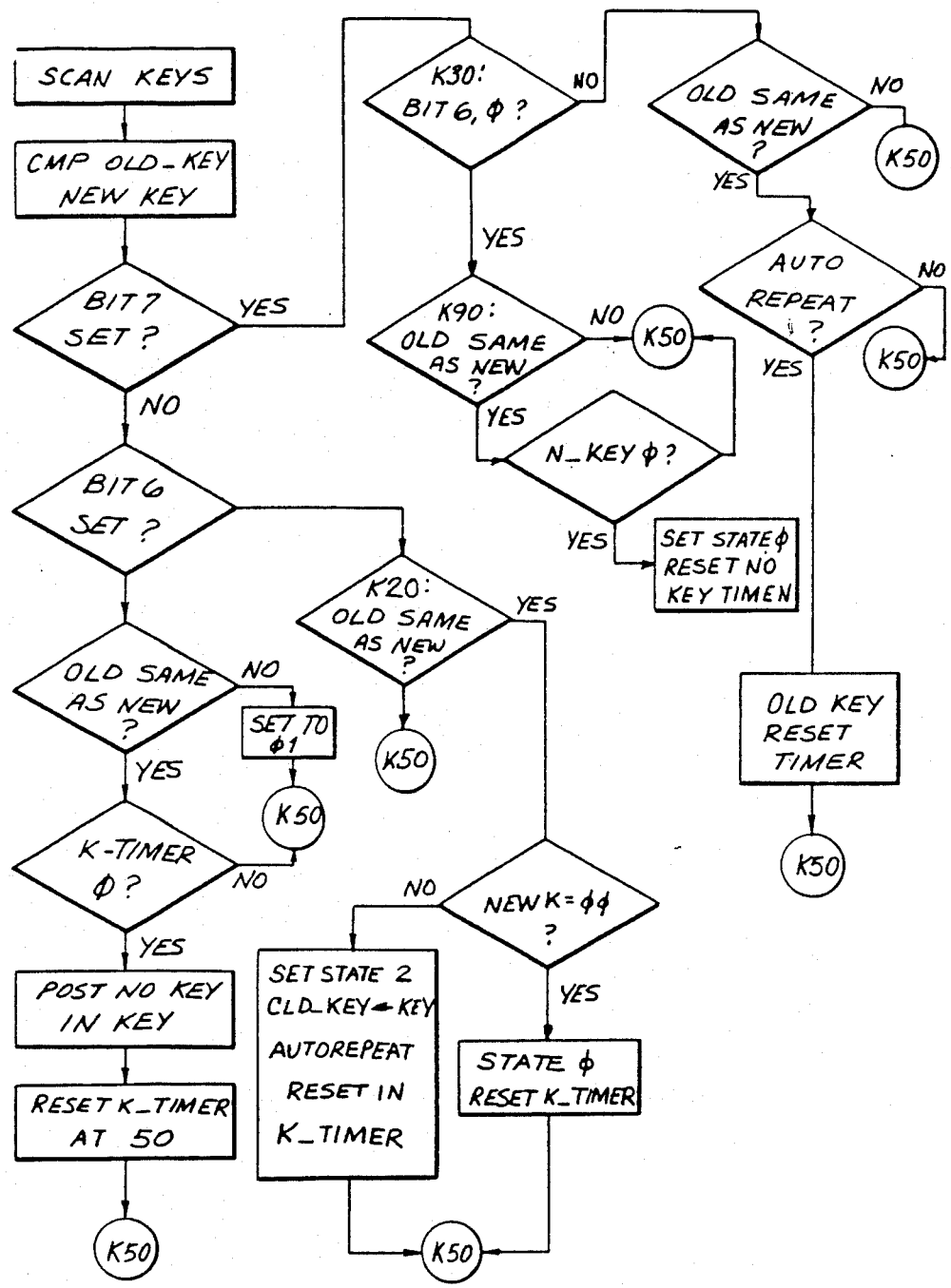
Figure 42:
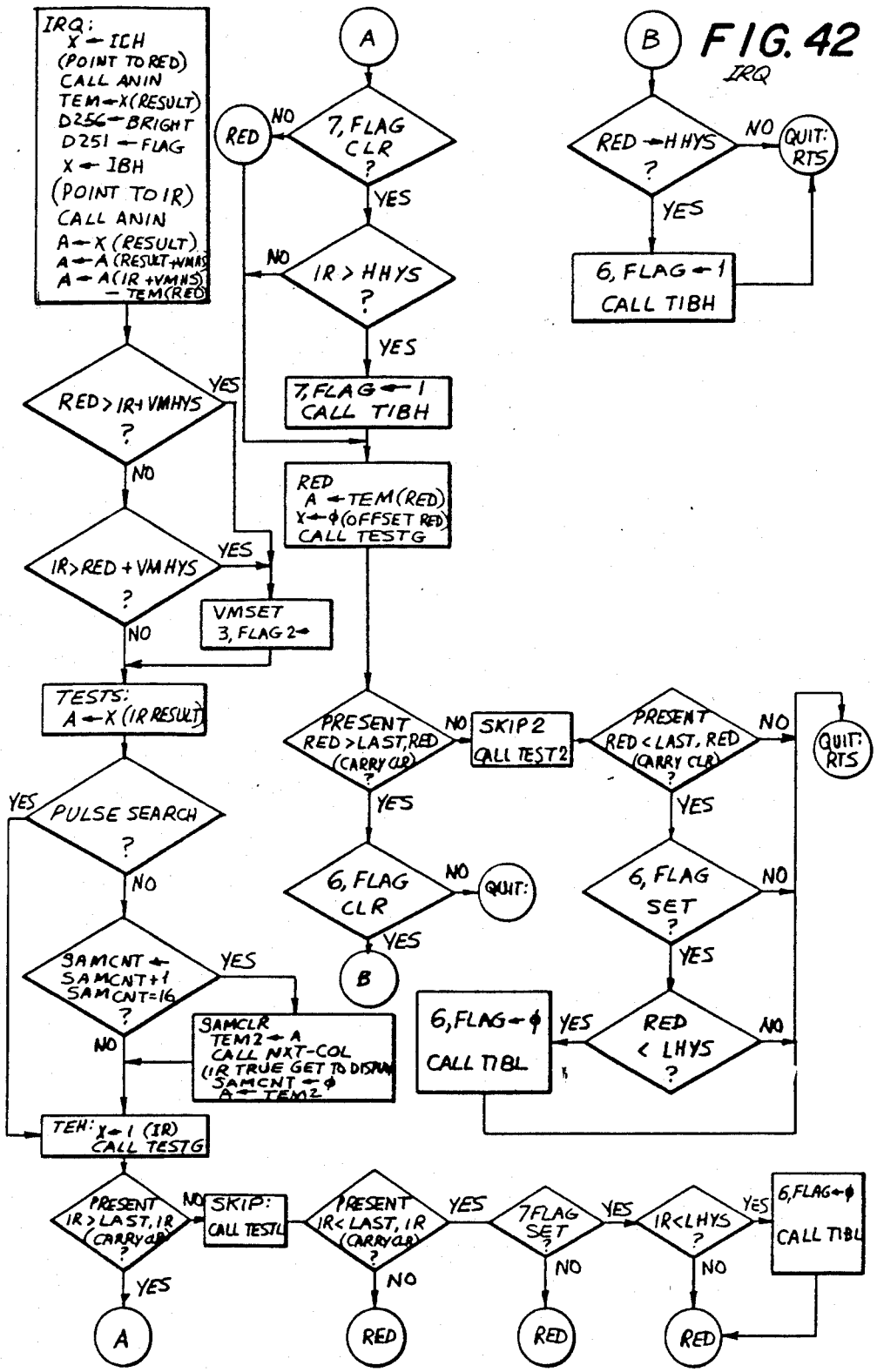
Figure 43:
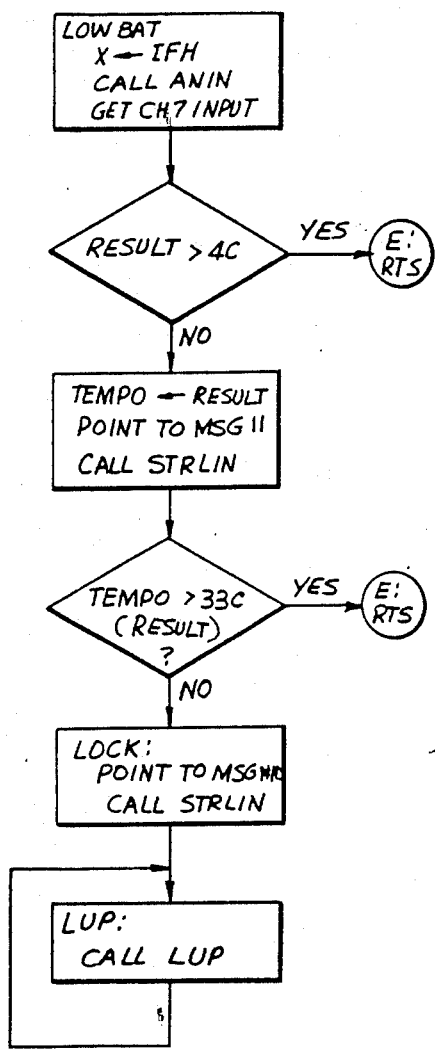
Figure 44A:
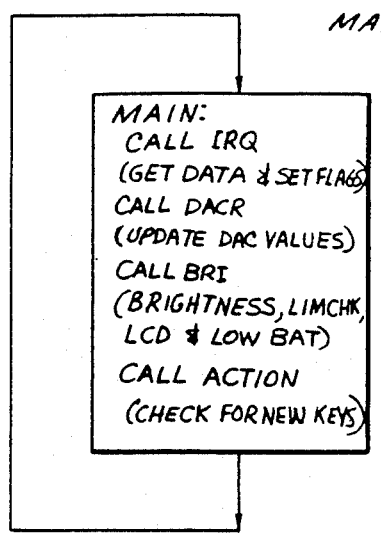
Figure 44B:
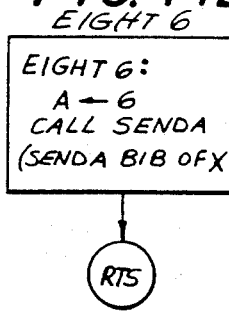
Figure 44C:
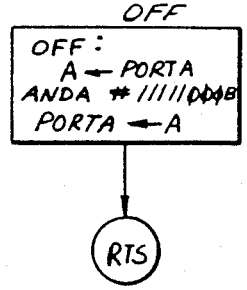
Figure 45:
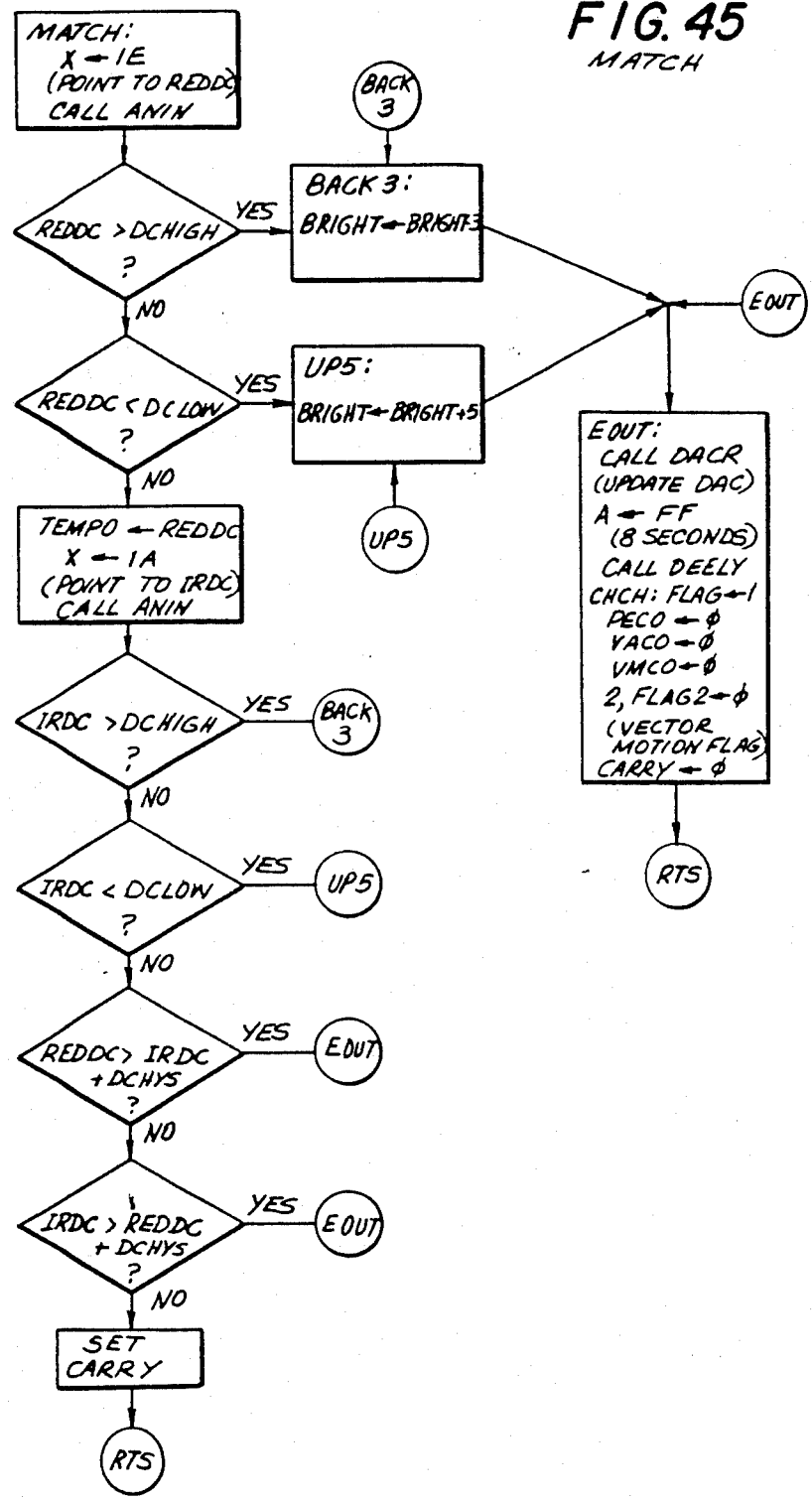
Figure 46:
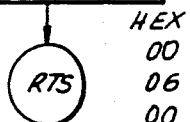
Figure 47:
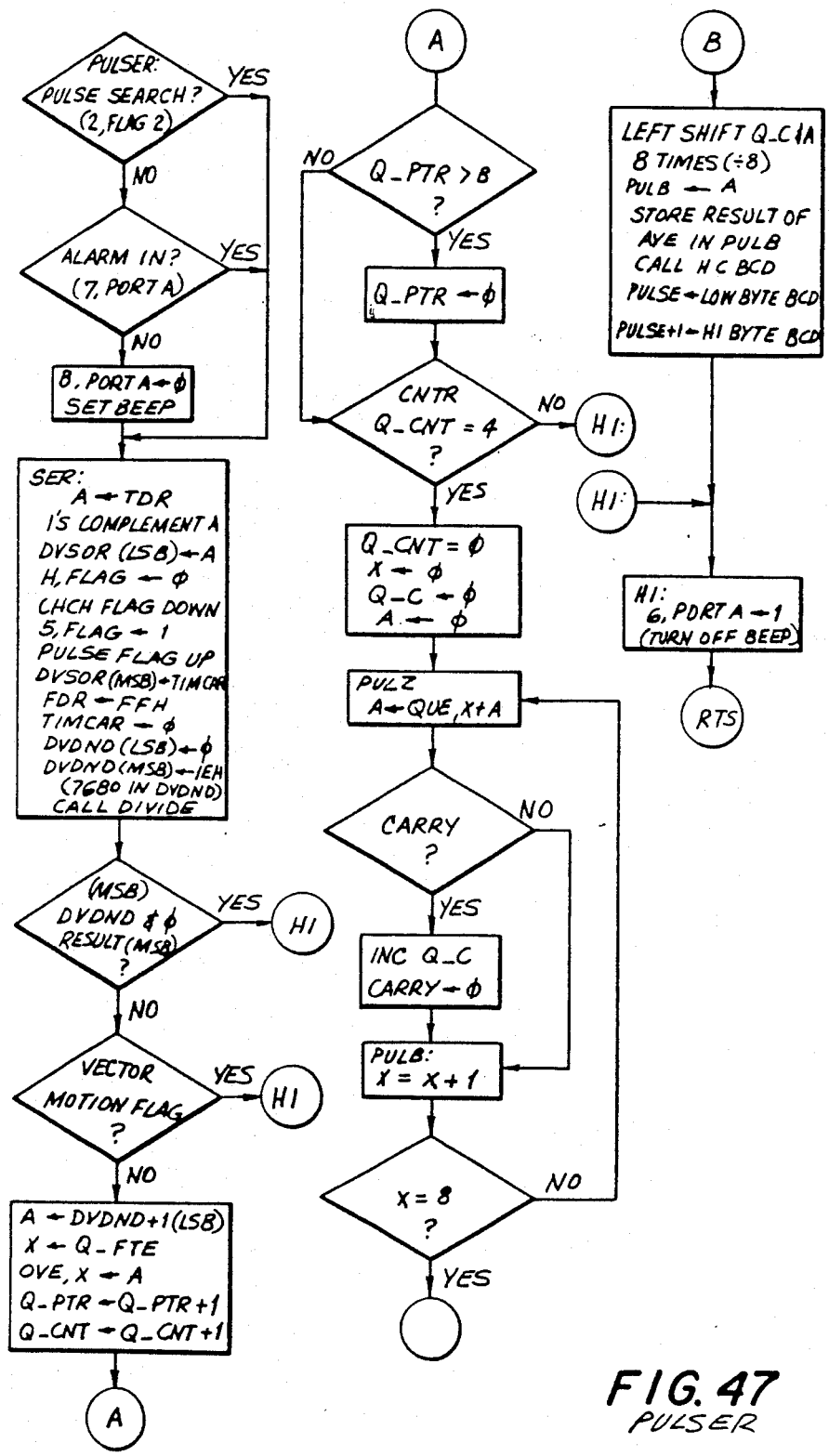
Figure 49A:
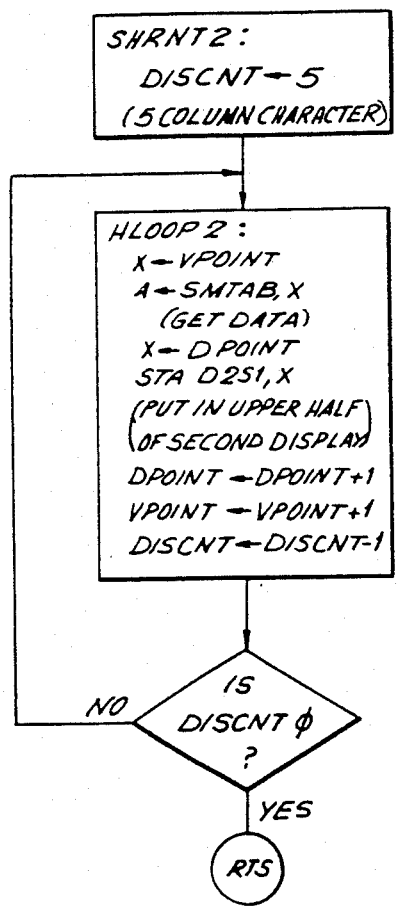
Figure 49B:
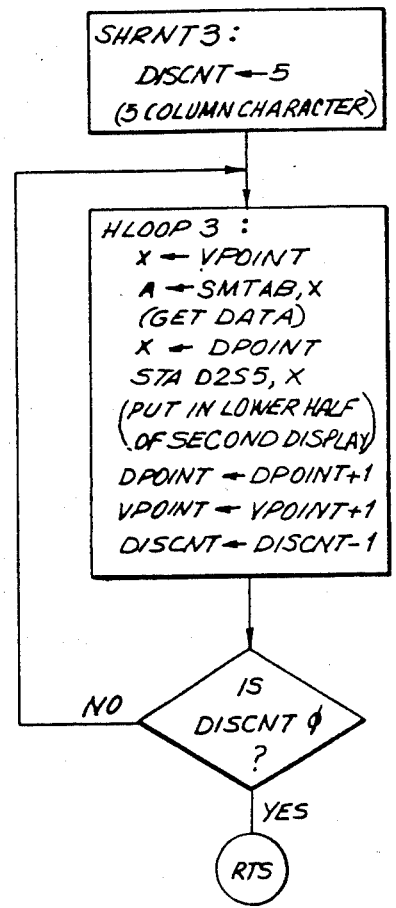
Figure 52A:
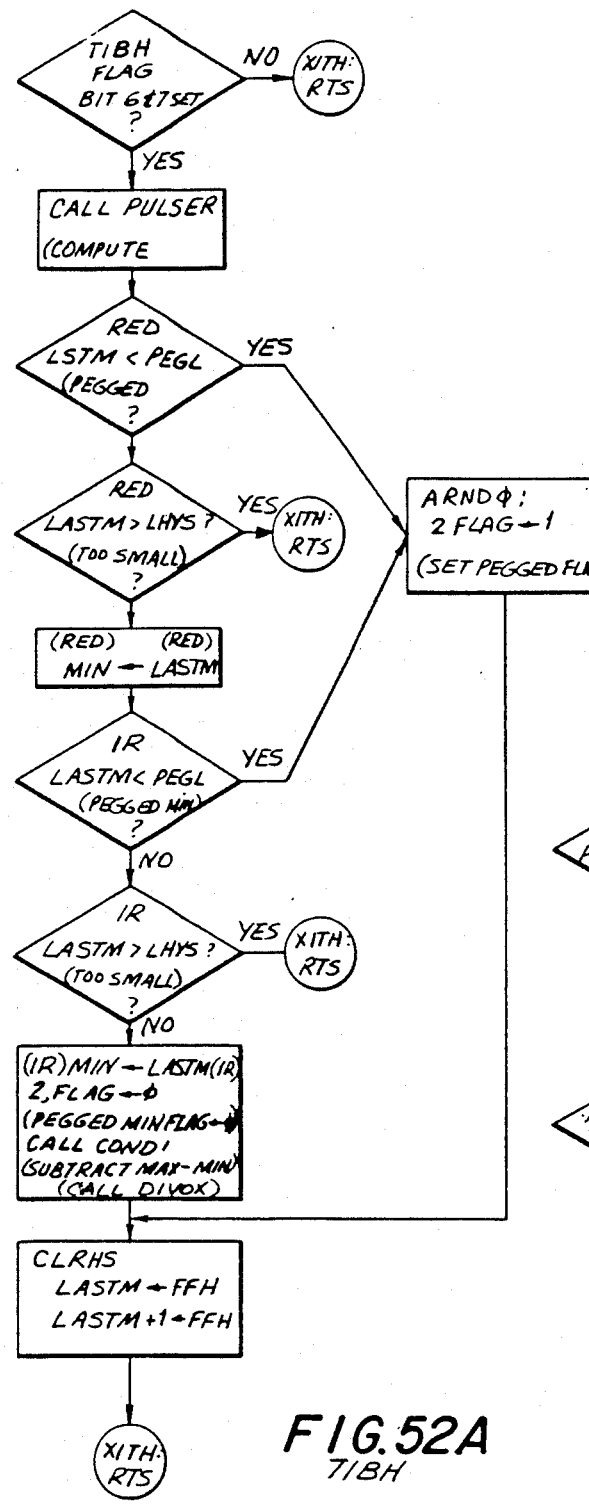
Figure 52B:
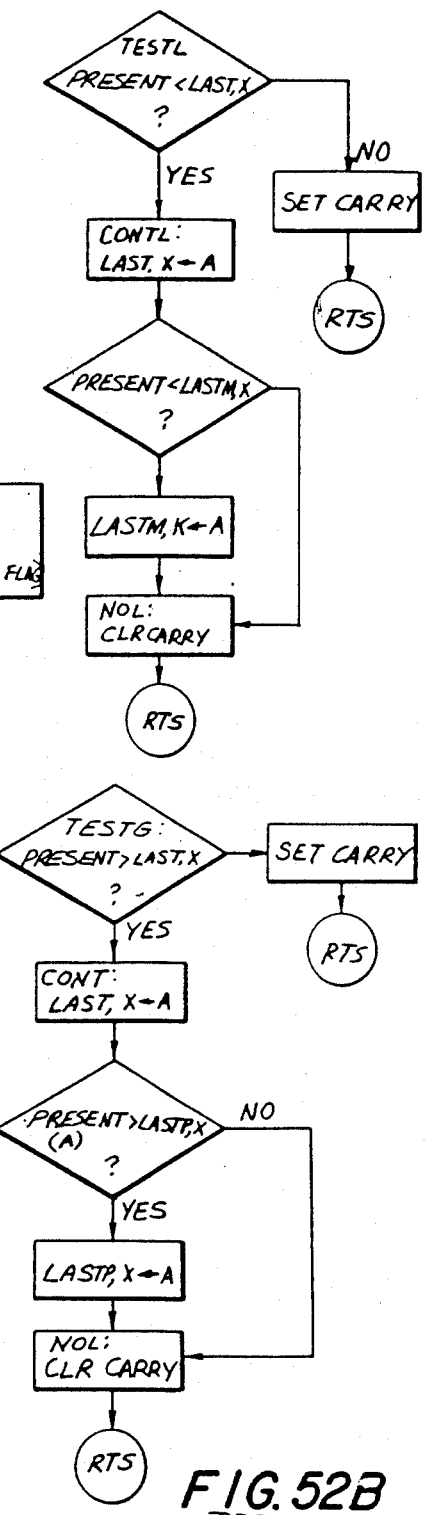
Figure 53:
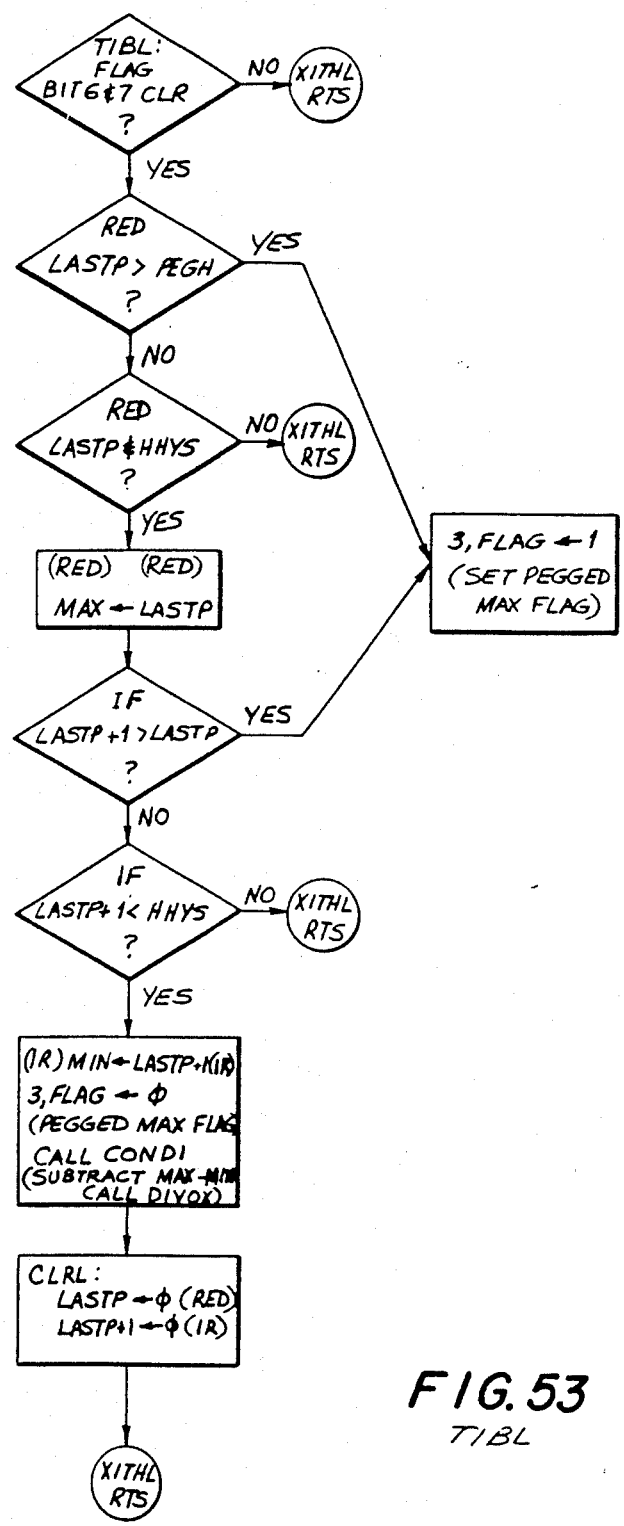
Figure 54A:
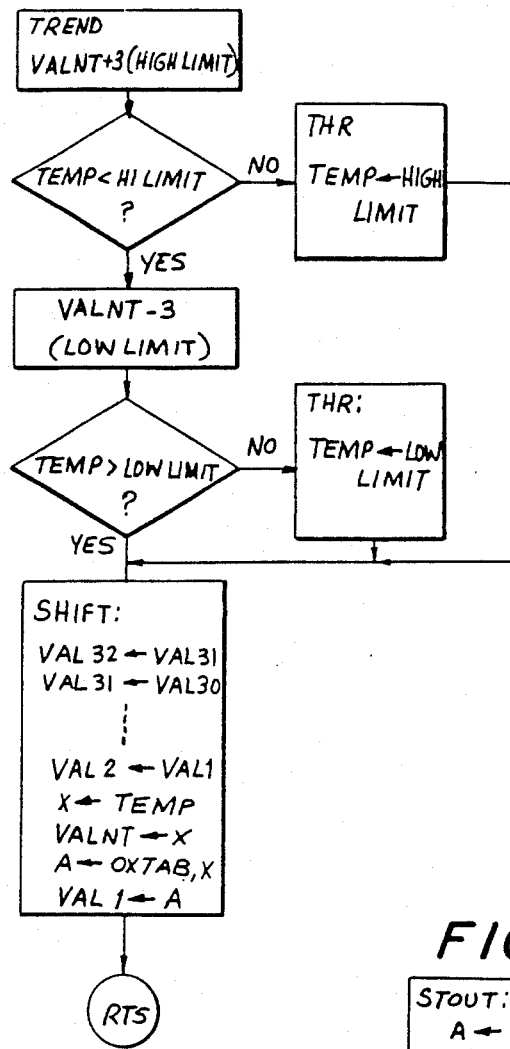
Figure 54B:
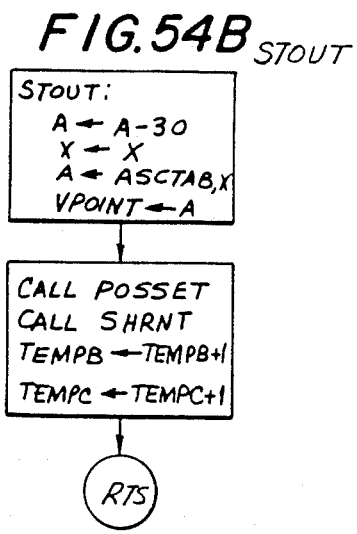

A quick program overview is shown in FIG. 28. The program is started a reset vector to go through SETUP to initialize the registers and the displays. The next routine is START. START puts the unit in pulse search mode, which checks to see if the probe is pres ent, that is, it checks for a DC voltage, and then it makes sure that these DC levels match. Then it starts a pulse search match. Now if it can't match or can't verify there's a probe present, it will loop on itself and wait.

The next mode is the pulses earch mode and during this mode we call IRQ, DACR, BRI and ACTION. All of these routines are important for the function of the unit. If two good pulses, are detected, an exit is made to the START routine and counts are cleared and PEGCNT is set. Then the accumulator A is set to Que plus 1, and the X register is set to zero. The Que buffer is 8 bits.

The main routine is the routine used during almost all normal functioning and it has calls to IRQ, DACR, BRI and ACTION.

The IRQ routine handles the data acquisition between the Red and IR signals and checking for determining max and min. It also calls the pulse routine because it knows when we have crossed the high hysteres is and low hysteres is levels. At the same time it checks to see if vector motion has occurred. If so, the proper flag is set.

The TESTG program tests the present value in the A register with the last stored value. It will update the peak if the value we have now is greater than the last peak. LASTP will hold the peak value at all times and this way a register is provided that is continually updating and keeping that peak or maximum value for either the Red or the IR. An offset system is used for this program, where the offset of 0 indicates that the program is looking at the Red channel, and a 1 indicates that the program is looking at the IR channel. This permits use of the same routine for both channels while having everything stored in the proper sequence. TESTL is the same kind of routine that tests the present value and, if less than the last value LASTM is updated if this value is indeed a new minimum for that sequence of sampling.

A test is made to sense high levels for both flags. If both flags are high, a routine, which indicates detection of a new pulse, to start sensing how long that pulse has been.

The routines used are described briefly as follows:

OVERVIEW

This diagram illustrates the overall operation of the program.

SETUP

This is an initialization routine to set up the various vectors and counters for the start of the operation.

START

This routine sets the unit into the Pulse Search mode, checks for the presence of the probe and match, and counts good pulses until two pulses are received, at which time it exits to

MAIN

IRQ

This routine handles the data acquisition, peak detect function, maximum/minimum lock-in, and call of the pulser routine. It reads both the Red and IR LED's at first, and locks in the max/min on the IR puls e peak detect. It also sets various flags.

DACR

This routine is the digital to analog convers ion output routine that sends out 36 bits on the serial bus from the microprocessor to the digital to analog convertor. It also updates DAC values

BRI

This routine controls the channels of the 4:1 MUX and LED brightness during the START and MAIN routines. It also controls LIMCHK, LCD and LOWBAT.

ACTION

Checks for keys and for mode changes due to alarms and/or key pushes or actuations

MAIN

This is the main loop which controls all of the acquisition, etc. There are only two ways to exit this loop, i.e. back to the pulse search mode and a lockup in the LOWBAT routine.

EIGHT6

Sends out 6 bits of X through SENDA of SENDB

OFF

Deselects serial devices

HXBCD

Converts the hexadecimal value in A to BCD (hundreds in X, tens/ones in A)

TMINT

Handles the timer interrupt and allows for timing events longer than two seconds, and clears interrupts after servicing.

PULSER

Reads the timer values, resets the timer to FF and checks for timer values. It computes Beats /minute with DIVIDE, and puts the computed value in 8 bit QUE with update.

LOWBAT

Checks line 7 of the A/D converter for proper battery voltage.

DIVIDE

This routine performs a divide function, putting a 16 bit dividend in DVDND (HI byte) and DVDND+1 (LO byte), the 16 bit divisor in DVSOR (HI byte) and DVSOR+1 (LO byte) adn the 16 bit result in DVDND (HI byte) and DVDND+1 (LO byte).

DEELY

This routine gives 2*A/256 seconds delay. The maximum possible delay is two seconds. It opens the response gates during the first half, then closes them.

DIVOX

This routine prepares for divide of DIFF IR/DIFF RED, calls the divide TREND and AVE routines, and converts the result to BCD.

DOUBLE2

In this routine, a value to be doubled is held in A, and the doubled value is returned to A.

ANIN

This is the analog input routine. It gets the value of CHANNEL (X value upon entry), and stores the value in X for exit.

GET8

GET8 bits from the serial bus.

SENDA

SEND A bits of X register out on its serial bus.

CONDI

This routine is called by TIBL or TIBH to computer differences and call DIVIDE if no pegged or vector motion flags are set.

TIBL

This routine tests for bits 6,7 or FLAG CLR, tests for MAX PEGS and large enough signals, stores max's and calls CONDI (for DIVOX)

TIBH

This routine tests for bits 6,7 of FLAG HIGH, calls PULSER, tests for PEGS and large enough signals, stores minimums and calls CONDI (for DIVOX, etc.)

TESTG

The PRESENT value is in A, and an OFFSET is in X (1 for IR and 0 for Red). The routine tests the PRESENT value in A with the LAST value, offset x, updates the LAST value if PRESENT value is greater than LAST value. The routine is exited with carry if it is greater, and without carry if it is not greater.

TESTL

PRESENT value is in A, OFFSET is in X (1 for IR, 0 for Red). The routine tests the PRESENT value in A with the LAST value, X, and updates LAST if PRESENT is less than LAST. Also updates LASTM if PRESENT is less than LASTM. The routine is exited with carry if it is not less, and with carry if it is less.

STOUT

Outputs a character held in A to a first display, lower half. A holds the ASCII value.

TREND

Establishes oxygen values by trending last raw values. Also shifts proper value into 32 bit FIFO buffer. TEMP hold current raw value. VALNT holds last raw value.

SHRNT

Single height character output routine. DPOINT (display pointer) and VPOINT (character data point) must be set before calling this routine. The routine writes to the lower half of the first display only.

SHRNT2

Single height routine. DPOINT (display pointer) and VPOINT (character data pointer) must be set before calling this routine. The routine writes to the upper half of the second display only.

SHRNT3

Single height routine. DPOINT (display pointer) and VPOINT (character data pointer) must be set before calling this routine. The routine writes to the lower half of the second display only.

MATCH

Match checks the D.C. levels on channels 4 and 5 to verify the levels are within limits of each other. If not, a rematch is performed.

BRIH & BRIL

Checks for both channel control bits, high and low respectively. If both are the same, then exit with carry set (unable to change channel). Otherwise change channel and exit with carry CLR (able to change channel).

STRLIN

Select message to output or LCD display.

INIT_BOB

Prepare RAM for display routine

AVE

Looks at response flag to determine how many points to average

AD16

16 bit addition routine, adding A to AVERL (LO byte) and to AVERH (HI byte)

INIT_DAVE

Initialize for keyboard and alarm defaults.

GETKEY

Keyboard scan routine
CONDI checks to see if the mode is correct. That is, if there hasn't been a gain change recently, and that none of the PEG flags are set. If it is, the max and the mins are taken to verify that a subtract of the minimum from the maximum can be made. Then the difference of those two in the IR and the Red is taken and put in their appropriate registers and Divox is called. Divox performs the divide and the lookup from the lookup table and puts them in a FIFO buffer, the moving average buffer, that used to display the actual saturation value.

Routines to communicate on the s erial bus are GETA or SENDA. Thes e are modified by routines called GET8 which will get 8 bits off the serial bus, and other routines that will send 8 bits on the serial bus. The routines first send out the address of the channel to look at and then bring that value back in by reading the values put on the serial bus.

INIT_BOB and INIT_DAVE erase and start over the displays and alarm check system to the default values.

MAIN routine gives a further definition of IRQ, DACR, BRI and ACTION. IRQ gets the data and sets the proper flags; DACR updates the DAK values; BRI is in charge of controlling the brightness levels, checking for any limits that are exceeding, updating the display and checking to see if there is a low battery condition. The final routine, ACTION, is used to make sure key pushes, etc are detected.

DIVOX is a routine called once the proper values for computing saturation are present. It prepares for the divide of the difference IR by difference Red, and then it calls a routine called Trend, and also some average routines which make sure that we put the right values are put into average. DIVOX prepares all the proper routines for the divide which is a 16×16 divide.

DIVIDE takes the number placed in the dividend area and in the divis or and gives a 16 bit result in DVDND, which is the same register as us ed for the dividend at the start.

LOWBAT checks to make sure that the battery voltage is checked for. A voltage divider (not s hown) off of the battery is us ed to provide a voltage and allow checking to make sure that the voltage is within range. The program firs t goes into a battery cons ervation mode, but if the battery cons ervation mode can be maintained, a lockup or s hutoff mode is called.

PULSAR checks to see if the proper mode is present to compute saturation. It also turns on the strobes PA6 to get a beep out with each pulse. Then the value TDR in the timer carry routine is taken and this value is divided by 7680. The result should be the pulse rate in a binary format. Once that pulse rate is determined it is put into the Que, which may be 8 or 16 bits.

The BRH and BRL routines are called to either change channels on the gain s elector to s elect the appropriate sized signal or, if within the limit, that is, the gain cannot be any greater to get more brightness; or if at the lowest gain, to decrease the brightness. This is a routine that allow changing the brightness level of the LEDs reflected on by the magnitude of the signal.

MATCH is the routine that checks to make sure that a proper match is achieved.

DEELY counts for a period of time and makes sure the proper delay after a gain change is provided to avoid looking at invalid AC signals which happens after a gain change.

TREND is the routine that takes either 8, 16 or 32 values and puts them into a FIFO. It als o lets them change by a value of plus or minus 3. This allows bris k enough movement, but als o throws out the spurious readings due to noise, etc.

The AVE routine takes all the values in the FIFO, adds them together, looks up the appropriate number and displays it on the display board.

While the invention has been dis clos ed with reference to a limited number of embodiments, it will be apparent that many variations may be made therein, and it is therefore intended in the following claims to cover each such variation and modification as falls within the true spirit of the invention.

What is claimed is:

1. In a reflectance oximeter comprising a sensor having a red light source, an infrared light source, and a photodetector for receiving light from said sources reflected from tissue, the improvement wherein said sensor comprises a housing having an aperture, a sensor carrier, said light sources and photodetector being mounted to have active light emitting and light receiving surfaces respectively at one side of said carrier, an electrical connection arrangement for said sources and photodetector within said housing, and resilient means for mounting said carrier in said aperture, whereby said carrier floats with respect to said housing.

2. The reflectance oximeter of claim 1 wherein said resilient means comprises means for biasing said carrier to have a uniform linear pressure for dis placements of said carrier through a determined range.

3. The reflectance oximeter of claim 1 wherein s aid resilient means comprises a membrane sealingly holding said darrier in said aperture.

4. The reflectance oximeter of claim 1 further comprising an interconnection cable extending into said housing, said electrical connection arrangement comprising a flexible connection board having electrical leads thereon, said sources and photosensor being mounted on said flexible board, said leads being connected to said cable.

5. The reflectance oximeter of claim 4 wherein said flexible board is mounted to resiliently yield to pressure applied to said carrier.

6. The reflectance oximeter of claim 5 wherein said flexible board is U-shaped.

7. In a non-invasive reflectance oximeter comprising a sensor having a red light source, an infrared light source, and a photodetector for receiving light from said sources reflected from tissue, the improvement wherein said sensor comprises a housing having an aperture and a sensor carrier resiliently mounted within said housing, said light sources and photodetector being mounted on said carrier to have active light emitting and light receiving surfaces respectively at one side of said carrier facing externally of said housing through said aperture, whereby said sensor may yield upon the application of external pressure thereto, and light barrier means coating said sources and photodetector on substantially all surfaces except said active light emitting and receiving surfaces.

8. The reflectance oximeter of claim 7 wherein said light barrier means comprises silver paint.

* * * * *